United States Patent
Bradford et al.

(10) Patent No.: US 12,162,834 B2
(45) Date of Patent: Dec. 10, 2024

(54) REACTIVE MESOGENS

(71) Applicant: Merck Patent GmbH, Darmstadt (DE)

(72) Inventors: Jack Bradford, Southampton (GB);
Kevin Adlem, Bournemouth (GB);
Naomi Weare, Southampton (GB);
Vicki Poole, Southampton (GB); Iain Gardiner, Chandlers Ford (GB)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 17/607,770

(22) PCT Filed: Apr. 27, 2020

(86) PCT No.: PCT/EP2020/061577
§ 371 (c)(1),
(2) Date: Oct. 29, 2021

(87) PCT Pub. No.: WO2020/221677
PCT Pub. Date: Nov. 5, 2020

(65) Prior Publication Data
US 2022/0234988 A1 Jul. 28, 2022

(30) Foreign Application Priority Data

Apr. 30, 2019 (EP) .................................. 19171804

(51) Int. Cl.
| | | |
|---|---|---|
| G02F 1/1333 | (2006.01) | |
| C07C 69/75 | (2006.01) | |
| C09K 19/20 | (2006.01) | |
| C09K 19/30 | (2006.01) | |
| C09K 19/32 | (2006.01) | |
| C09K 19/34 | (2006.01) | |

(52) U.S. Cl.
CPC .......... *C07C 69/75* (2013.01); *C09K 19/2028* (2013.01); *C09K 19/3068* (2013.01); *C09K 19/322* (2013.01); *C09K 19/3447* (2013.01); *C09K 19/3458* (2013.01); *C09K 19/3491* (2013.01); *C09K 2019/2035* (2013.01); *C09K 2019/2042* (2013.01); *C09K 2019/2078* (2013.01); *C09K 2019/3075* (2013.01); *C09K 2019/3077* (2013.01)

(58) Field of Classification Search
CPC .......... C09K 19/2028; C09K 19/3068; C09K 19/322; C09K 19/3447; C09K 19/3458; C09K 19/3491; C09K 19/32; C09K 19/3804; C09K 2019/2035; C09K 2019/2042; C09K 2019/2078; C09K 2019/3075; C09K 2019/3077; C09K 2019/0496; C09K 2019/123; C09K 2019/188; C09K 2019/3071; C09K 2019/3083; C09K 2019/0448; C09K 2019/0444; C09K 2019/3804; C07C 69/75; C07C 69/76; C07C 2601/14; C08F 2/48; C08F 220/22; C08F 220/303; G02F 1/1333

See application file for complete search history.

(56) References Cited

U.S. PATENT DOCUMENTS

| | | | |
|---|---|---|---|
| 5,389,698 A | 2/1995 | Chigrinov et al. | |
| 5,518,652 A * | 5/1996 | Parri ................ | C09K 19/3857 |
| | | | 526/292.3 |
| 5,602,661 A | 2/1997 | Schadt et al. | |
| 6,717,644 B2 | 4/2004 | Schadt et al. | |
| 7,060,200 B1 | 6/2006 | Farrand et al. | |
| 2006/0172090 A1 | 8/2006 | Syundo | |
| 2016/0318845 A1 | 11/2016 | Katoh et al. | |
| 2022/0234988 A1* | 7/2022 | Bradford ............ | C09K 19/3447 |

FOREIGN PATENT DOCUMENTS

| | | |
|---|---|---|
| EP | 0888565 A1 | 1/1999 |
| EP | 0940707 A1 | 9/1999 |
| GB | 2329393 A | 3/1999 |
| JP | 2005265896 A | 9/2005 |
| JP | 2005345982 A | 12/2005 |
| WO | 2008119427 A1 | 10/2008 |
| WO | 2009058396 A1 | 5/2009 |
| WO | 2013117284 A1 | 8/2013 |
| WO | 2015115390 A1 | 8/2015 |
| WO | 2016020035 A1 | 2/2016 |
| WO | WO 2021/259825 A1 * | 12/2021 ............. C09K 19/54 |

OTHER PUBLICATIONS

International Search Report and Written Opinion for International Application No. PCT/EP2020/061577, dated Jun. 24, 2020, 13 pages.

\* cited by examiner

*Primary Examiner* — Geraldina Visconti
(74) *Attorney, Agent, or Firm* — Buchanan Ingersoll & Rooney PC

(57) ABSTRACT

Reactive mesogens (RMs), mixtures and formulations comprising RMs, polymers obtained from such RMs and RM mixtures, and the use of the RMs, RM mixtures and polymers in optical or electrooptical components or devices, like optical films for liquid crystal displays (LCDs).

17 Claims, 2 Drawing Sheets

REACTIVE MESOGENS

CROSS-REFERENCE TO RELATED APPLICATIONS

This application is a U.S. national stage application filed and claiming priority under 35 U.S.C. §§ 120 and 365 (a) of International Application No. PCT/EP2020/061577, filed Apr. 27, 2020, which claims priority under 35 U.S.C. § 119 of European Patent Application No. 19171804.8, filed Apr. 30, 2019, each of which applications is incorporated herein by reference in its entirety and for all purposes.

FIELD OF THE INVENTION

The invention relates to novel reactive mesogens (RMs), to mixtures and formulations comprising them, to polymers obtained from such RMs and RM mixtures, and the use of the RMs, RM mixtures and polymers in optical or electrooptical components or devices, like optical films for liquid crystal displays (LCDs).

BACKGROUND AND PRIOR ART

Polymerisable liquid crystal materials are known in prior art for the preparation of anisotropic polymer films. These films are usually prepared by coating a thin layer of a polymerisable liquid crystal mixture onto a substrate, aligning the mixture into a uniform orientation and finally fixing the orientation of the liquid crystal molecules by polymerizing the polymerizable liquid crystal material. The orientation of the liquid crystal molecules in the polymerized film can thereby be planar, i.e. where the liquid crystal molecules are oriented substantially parallel to the layer, homeotropic (rectangular or perpendicular to the layer) or tilted. Corresponding optical films are described, for example, in EP 0 940 707 B1, EP 0 888 565 B1 and GB 2 329 393 B1.

As commonly known by the expert, optical films based on polymerisable liquid crystal materials typically exhibit a wavelength dependent retardation. In this regard, Three main kind of optical behaviour are known:
i) "Normal" or "Positive" optical dispersion, such as for example described in EP 0 940 707 B1
ii) "Reverse" or "Negative" optical dispersion, such as, for example described in WO 2016/020035 A1, and
iii) "Flat" optical dispersion, such as for example described in WO 2009/058396 A1.

For example, flat or negative dispersion polymerisable liquid crystal materials can be produced by adding at least one component with an ordinary refractive index (no) higher than extraordinary refractive index (ne) in the formulation. Therefore, highly conjugated substituents are required in the orthogonal position with respect to the long-axis of the molecules. The latter materials absorb part of the UV dose when curing optical films which results in poor degree of cure and poor thermal durability of cured films. Besides the latter molecular blocks can easily oxidise under high temperatures in the presence of oxygen. Same applies to high birefringent formulations containing highly conjugated reactive mesogens which reduces the thermal durability of cured films and which are typically prone to yellowing.

For example, WO 2008/119427 A1 describes a birefringent polymer film with negative optical dispersion, which is obtainable from a polymerisable LC material comprising as negative dispersion component compounds having the structure shown below or derivatives thereof:

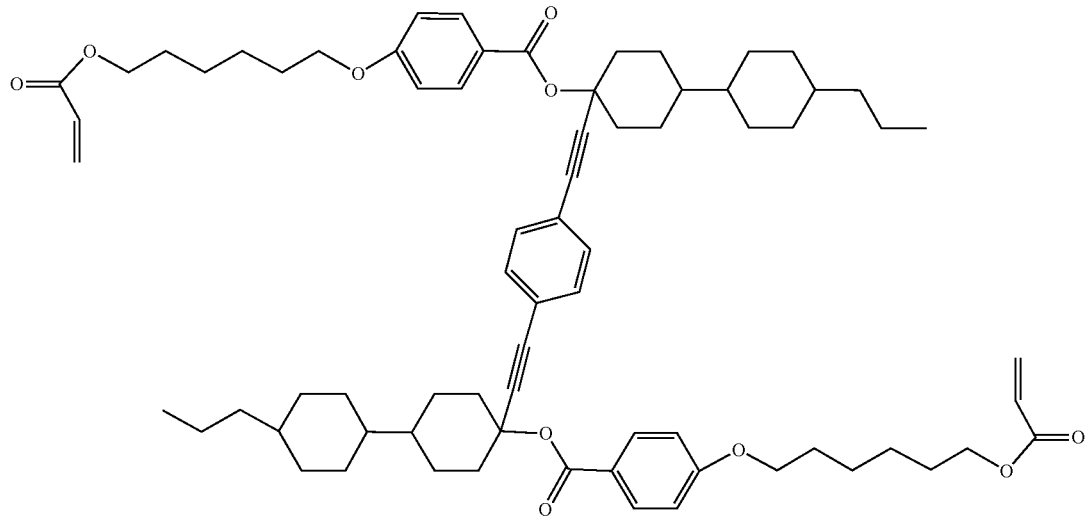 [SMILES: C=CC(=O)OCCCCCCOc1ccc(C(=O)OC2(C#Cc3ccc(C#CC4(OC(=O)c5ccc(OCCCCCCOC(=O)C=C)cc5)CCC(C5CCC(CCC)CC5)CC4)cc3)CCC(C3CCC(CCC)CC3)CC2)cc1]

The ratio of the negative dispersion component in the polymerisable LC material disclosed in WO 2008/119427 A1 is for example 50-60% of the total amount of solids (i.e. without solvents). However, the bulky nature of the negative dispersion compounds according to the prior art are typically hard to align or give formulations with a narrow process window for annealing temperature, which is not convenient for mass production.

Reducing the amount of the above-described materials in the mixture has a significant positive effect on the solubility, durability and process window of the mixture. Currently, this cannot be achieved without detriment to the negative dispersion property of the film.

WO 2015/115390 A1 discloses compounds of the following generic structure:

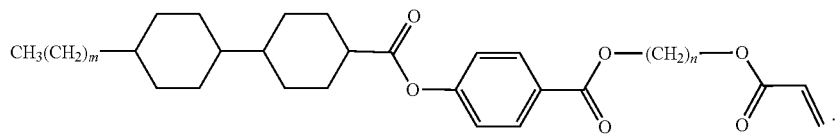

polymerizable compositions comprising these compounds; a film which is formed from this polymerizable composition; and a half mirror for displaying a projected image, which comprises this film and suggest that a film such as a low birefringence retardation film and a reflective film having high selectivity for reflection wavelength range can be produced using this polymerizable composition. However, WO 2015/115390 A1 is silent about the utilization of these compounds in polymer films exhibiting a negative optical dispersion.

It is therefore an aim of the present invention to provide improved RMs, RM mixtures and RM formulations, which do not have the drawbacks of materials known from prior art. In particular it is an aim to provide RMs and RM mixtures and RM formulations, preferably having negative optical dispersion, that are suitable for preparing polymers by in situ UV photopolymerisation, exhibit a good solubility, show an improved broadening potential, and which have favorable transition temperatures.

Other aims of the invention are immediately evident to the expert from the following description.

Surprisingly, the inventors of the present invention have found that the compounds according to claim 1 and their utilization can improve the currently known optical films significantly.

SUMMARY OF THE INVENTION

Thus, the present invention relates to compounds of formula I,

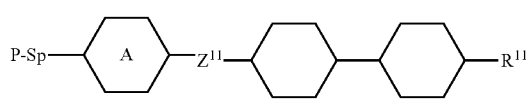

P is a polymerisable group,
Sp is a spacer group or a single bond, preferably Sp denotes
—$(CH_2)_n$— wherein n denotes 1 to 9, such as methylene, ethylene, propylene, butylene, pentylene, hexylene, heptylene, octylene, nonylene, preferably n denotes an integer between 5 and 7, such as methylene, ethylene, propylene, butylene, pentylene, hexylene, heptylene,
$R^{11}$ is alkyl, alkoxy, thioalkyl, alkylcarbonyl, alkoxycarbonyl, alkylcarbonyloxy or alkoxycarbonyloxy preferably with 1 to 15 C atoms which is optionally fluorinated.
A denotes, an aromatic or alicyclic group, which optionally contains one or more heteroatoms selected from N, O and S, and is optionally mono- or polysubstituted by L,
L is F, Cl, Br, I, —CN, —$NO_2$, —NCO, —NCS, —OCN, —SCN, —C(=O)$NR^xR^y$, —C(=O)$OR^x$, —C(=O)$R^x$, —$NR^xR^y$, —OH, —$SF_5$, or straight chain or branched alkyl, alkoxy, alkylcarbonyl, alkoxycarbonyl, alkylcarbonyloxy or alkoxycarbonyloxy with 1 to 12, wherein one or more H atoms are optionally replaced by F or Cl, preferably F, —CN or straight chain or branched alkyl, alkoxy, alkylcarbonyl, alkoxycarbonyl, alkylcarbonyloxy or alkoxycarbonyloxy 1 to 6 C atoms,
$R^{00}$, $R^{000}$,
$R^x$ and $R^y$ independently of each other denote H or alkyl with 1 to 12 C-atoms,
$Z^{11}$ and $Z^{12}$ denotes, in case of multiple occurrence independently of one another, —O—, —S—, —CO—, —COO—, —OCO—, —S—CO—, —CO—S—, —O—COO—, —CO—$NR^{00}$—, —$NR^{00}$—CO—, —$NR^{00}$—CO—$NR^{00}$, —$NR^{00}$—CO—O—, —O—CO—$NR^{00}$—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$(CH_2)_{n1}$—, —$CF_2CH_2$—, —$CH_2CF_2$—, —$CF_2CF_2$—, —CH=N—, —N=CH—, —N=N—, —CH=$CR^{00}$—, —$CY^1$=$CY^2$—, —C≡C—, —CH=CH—COO—, —OCO—CH=CH— or a single bond, preferably —COO—, —OCO— or a single bond, more preferably —COO— or —OCO—.
$Y^1$ and $Y^2$ independently of each other denote H, F, Cl or CN, and
n1 is an integer from 1 to 10, preferably 1, 2, 3 or 4.

The invention further relates to a mixture, which is hereinafter referred to as "RM mixture", comprising two or more RMs, at least one of which is a compound of formula I.

The invention further relates to a formulation, which is hereinafter referred to as "RM formulation", comprising one or more compounds of formula I or an RM mixture as described above and below, and further comprising one or more solvents and/or additives.

The invention further relates to a polymer obtainable by polymerising a compound of formula I or an RM mixture as described above and below, preferably wherein the RMs are aligned, and preferably at a temperature where the RMs or RM mixture exhibit a liquid crystal phase.

The invention further relates to the use of the compounds of formula I, the RM mixture or the polymer as described above and below in optical, electrooptical or electronic components or devices.

The invention further relates to an optical, electrooptical or electronic device or a component thereof, comprising an RM, RM mixture or polymer as described above and below.

Said components include, without limitation, optical retardation films, polarizers, compensators, beam splitters, reflective films, alignment layers, colour filters, antistatic protection sheets, electromagnetic interference protection sheets, polarization controlled lenses for example for autostereoscopic 3D displays, IR reflection films for example for window applications, and lenses for light guides, focusing and optical effects, eg. 3D, holography, telecomms.

Said devices include, without limitation, electrooptical displays, especially LC displays, autostereoscopic 3D displays, organic light emitting diodes (OLEDs), optical data storage devices, and windows.

Definitions of Terms

As used herein, the term "polymer" will be understood to mean a molecule that encompasses a backbone of one or more distinct types of repeating units (the smallest constitutional unit of the molecule) and is inclusive of the commonly known terms "oligomer", "copolymer", "homopolymer" and the like. Further, it will be understood that the term polymer is inclusive of, in addition to the polymer itself, residues from initiators, catalysts, and other elements attendant to the synthesis of such a polymer, where such residues are understood as not being covalently incorporated thereto. Further, such residues and other elements, while normally removed during post polymerisation purification processes, are typically mixed or co-mingled with the polymer such that they generally remain with the polymer when it is transferred between vessels or between solvents or dispersion media.

The term "(meth)acrylic polymer" as used in the present invention includes a polymer obtained from acrylic monomers, a polymer obtainable from methacrylic monomers, and a corresponding co-polymer obtainable from mixtures of such monomers.

The term "polymerisation" means the chemical process to form a polymer by bonding together multiple polymerisable groups or polymer precursors (polymerisable compounds) containing such polymerisable groups.

The terms "film" and "layer" include rigid or flexible, self-supporting or freestanding films with mechanical stability, as well as coatings or layers on a supporting substrate or between two substrates.

The term "liquid crystal or mesogenic compound" means a compound comprising one or more calamitic (rod- or board/lath-shaped) or discotic (disk-shaped) mesogenic groups. The term "mesogenic group" means a group with the ability to induce liquid crystal (LC) phase behaviour. The compounds comprising mesogenic groups do not necessarily have to exhibit an LC phase themselves. It is also possible that they show LC phase behaviour only in mixtures with other compounds, or when the mesogenic compounds or materials, or the mixtures thereof, are polymerised. For the sake of simplicity, the term "liquid crystal" is used hereinafter for both mesogenic and LC materials. For an overview of definitions see C. Tschierske, G. Pelzl and S. Diele, Angew. Chem. 2004, 116, 6340-6368.

A calamitic mesogenic group is usually comprising a mesogenic core consisting of one or more aromatic or non-aromatic cyclic groups connected to each other directly or via linkage groups, optionally comprising terminal groups attached to the ends of the mesogenic core, and optionally comprising one or more lateral groups attached to the long side of the mesogenic core, wherein these terminal and lateral groups are usually selected e.g. from carbyl or hydrocarbyl groups, polar groups like halogen, nitro, hydroxy, etc., or polymerisable groups.

The term "reactive mesogen" (RM) means a polymerisable mesogenic or liquid crystal compound.

Polymerisable compounds with one polymerisable group are also referred to as "monoreactive" compounds, compounds with two polymerisable groups as "direactive" compounds, and compounds with more than two polymerisable groups as "multireactive" compounds. Compounds without a polymerisable group are also referred to as "non-reactive" compounds.

The term "polymerisable LC material" means a material, which comprises of more than 90% by weight, preferably more than 95% by weight, more preferably more than 98% by weight of polymerisable compounds, as described above and below.

The term "non-mesogenic compound or material" means a compound or material that does not contain a mesogenic group as defined above.

Visible light is electromagnetic radiation that has wavelength in a range from about 400 nm to about 740 nm. Ultraviolet (UV) light is electromagnetic radiation with a wavelength in a range from about 200 nm to about 450 nm.

The Irradiance ($E_e$) or radiation power is defined as the power of electromagnetic radiation (dθ) per unit area (dA) incident on a surface:

$$E_e = d\theta/dA.$$

The radiant exposure or radiation dose ($H_e$), is as the irradiance or radiation power ($E_e$) per time (t):

$$H_e = E_e \cdot t.$$

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

The term "clearing point" means the temperature at which the transition between the mesophase with the highest temperature range and the isotropic phase occurs.

The term "director" is known in prior art and means the preferred orientation direction of the long molecular axes (in case of calamitic compounds) or short molecular axes (in case of discotic compounds) of the liquid-crystalline or RM molecules. In case of uniaxial ordering of such anisotropic molecules, the director is the axis of anisotropy.

All physical properties have been and are determined according to "Merck Liquid Crystals, Physical Properties of Liquid Crystals", Status November 1997, Merck KGaA, Germany and are given for a temperature of 20° C., unless explicitly stated otherwise. The optical anisotropy (Δn) is determined at a wavelength of 589.3 nm In case of doubt the definitions as given in C. Tschierske, G. Pelzl and S. Diele, Angew. Chem. 2004, 116, 6340-6368 shall apply.

Unless explicitly stated otherwise in the given generic formulae, the following terms have the following meanings:

"Carbyl group" denotes a mono- or polyvalent organic group containing at least one carbon atom which either contains no further atoms (such as, for example, —C≡C—) or optionally contains one or more further atoms, such as, for example, N, O, S, P, Si, Se, As, Te or Ge (for example carbonyl, etc.). "Hydrocarbyl group" denotes a carbyl group, which additionally contains one or more H atoms and optionally one or more heteroatoms, such as, for example, N, O, S, P, Si, Se, As, Te or Ge.

A carbyl or hydrocarbyl group can be a saturated or unsaturated group. Unsaturated groups are, for example, aryl, alkenyl, or alkinyl groups. A carbyl or hydrocarbyl group having more than 3 C atoms can be straight chain, branched and/or cyclic and may contain spiro links or condensed rings.

Preferred carbyl and hydrocarbyl groups are optionally substituted alkyl, alkenyl, alkinyl, alkoxy, alkylcarbonyl, alkoxycarbonyl, alkylcarbonyloxy and alkoxycarbonyloxy having 1 to 40, preferably 1 to 25, particularly preferably 1 to 18 C atoms, optionally substituted aryl or aryloxy having 6 to 40, preferably 6 to 25 C atoms, or optionally substituted alkylaryl, arylalkyl, alkylaryloxy, arylalkyloxy, arylcarbonyl, aryloxycarbonyl, arylcarbonyloxy and aryloxycarbonyloxy having 6 to 40, preferably 6 to 25 C atoms. Further preferred carbyl and hydrocarbyl groups are $C_1$-$C_{40}$ alkyl, $C_2$-$C_{40}$ alkenyl, $C_2$-$C_{40}$ alkinyl, $C_3$-$C_{40}$ allyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_2$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkinyl, $C_3$-$C_{22}$ allyl, $C_4$-$C_{22}$ alkyldienyl, $C_6$-$C_{12}$ aryl, $C_6$-$C_{20}$ arylalkyl, and $C_2$-$C_{20}$ heteroaryl.

Further preferred carbyl and hydrocarbyl groups are straight-chain, branched or cyclic alkyl radicals having 1 to 40, preferably 1 to 25 C atoms, more preferably 1 to 12 C atoms, which are unsubstituted or mono- or polysubstituted by F, Cl, Br, I or CN and in which one or more non-adjacent $CH_2$ groups may each be replaced, independently of one another, by —C($R^x$)=C($R^x$)—, —C≡C—, —N($R^x$)—, —O—, —S—, —CO—, —CO—O—, —O—CO—, —O—CO—O— in such a way that O and/or S atoms are not linked directly to one another.

Above, $R^x$ preferably denotes H, halogen, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O—, and in which one or more H atoms may be replaced by fluorine, an optionally substituted aryl or aryloxy group having 6 to 40 C atoms or an optionally substituted heteroaryl or heteroaryloxy group having 2 to 40 C atoms.

Preferred alkyl groups are, for example, methyl, ethyl, n-propyl, isopropyl, n-butyl, isobutyl, s-butyl, t-butyl, 2-methylbutyl, n-pentyl, s-pentyl, n-hexyl, 2-ethylhexyl, n-heptyl, n-octyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkinyl groups are, for example, ethynyl, propynyl, butynyl, pentynyl, hexynyl, octynyl, etc.

Preferred alkoxy groups are, for example, methoxy, ethoxy, 2-methoxy-ethoxy, n-propoxy, i-propoxy, n-butoxy, i-butoxy, s-butoxy, t-butoxy, 2-methylbutoxy, n-pentoxy, n-hexoxy, n-heptyloxy, n-octyloxy, n-nonyloxy, n-decyloxy, n-undecyloxy, n-dodecyloxy, etc.

Preferred amino groups are, for example, dimethylamino, methylamino, methylphenylamino, phenylamino, etc.

Aryl and heteroaryl groups can be monocyclic or polycyclic, i.e. they can have one ring (such as, for example, phenyl) or two or more rings, which may also be fused (such as, for example, naphthyl) or covalently linked (such as, for example, biphenyl), or contain a combination of fused and linked rings. Heteroaryl groups contain one or more heteroatoms, preferably selected from O, N, S and Se.

Particular preference is given to mono-, bi-, or tricyclic aryl groups having 6 to 25 C atoms and mono-, bi- or tricyclic heteroaryl groups having 2 to 25 C atoms, which optionally contain fused rings and which are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1"]terphenyl-2'-yl, naphthyl, anthracene, binaphthyl, phenanthrene, pyrene, dihydropyrene, chrysene, perylene, tetracene, pentacene, benzo-pyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, iso-indole, indolizine, indazole, benzimidazole, benzotriazole, purine, naphth-imidazole, phenanthrimidazole, pyridimidazole, pyrazinimidazole, quinoxa-linimidazole, benzoxazole, naphthoxazole, anthroxazole, phenanthroxa-zole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenan-throline, thieno[2,3b]thiophene, thieno[3,2b]thiophene, dithienothiophene, isobenzothiophene, dibenzothiophene, benzothiadiazothiophene, or combinations of these groups. The heteroaryl groups may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e. those that contain exclusively single bonds, and partially unsaturated rings, i.e. those that may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi-, or tricyclic groups having 3 to 25 C atoms, which optionally contain fused rings and which are optionally substituted. Preference is furthermore given to 5-, 6-, 7- or 8-membered carbocyclic groups in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

The aryl, heteroaryl, (non-aromatic) alicyclic and heterocyclic groups optionally have one or more substituents, which are preferably selected from the group comprising silyl, sulfo, sulfonyl, formyl, amine, imine, nitrile, mercapto, nitro, halogen, $C_1$-$C_{12}$ alkyl, $C_6$-$C_{12}$ aryl, $C_1$-$C_{12}$ alkoxy, hydroxyl, or combinations of these groups.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents, also referred to as "L" below, are, for example, F, Cl, Br, I, —OH, —CN, —NO$_2$, —NCO, —NCS, —OCN, —SCN, —C(=O)N(R$^x$)$_2$, —C(=O)Y$^x$, —C(=O)R$^x$, —C(=O)OR$^x$, —N(R$^x$)$_2$, in which R$^x$ has the above-mentioned meaning, and above Y$^x$ denotes halogen, optionally substituted silyl, optionally substituted aryl or heteroaryl having 4 to 40, preferably 4 to 20 ring atoms, and straight-chain or branched alkyl, alkenyl, alkinyl, alkoxy, alkylcarbonyl, alkoxycarbonyl, alkylcarbonyloxy or alkoxycarbonyloxy having 1 to 25 C atoms, in which one or more H atoms may optionally be replaced by F or C.

"Substituted silyl or aryl" preferably means substituted by halogen, —CN, R$^y$, —OR$^y$, —CO—R$^y$, —CO—O—R$^y$, —O—CO—R$^y$ or —O—CO—O—R$^y$, in which R$^y$ denotes H, a straight-chain, branched or cyclic alkyl chain having 1 to 12 C atoms.

In the formula shown above and below, a substituted phenylene ring

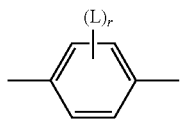

is preferably

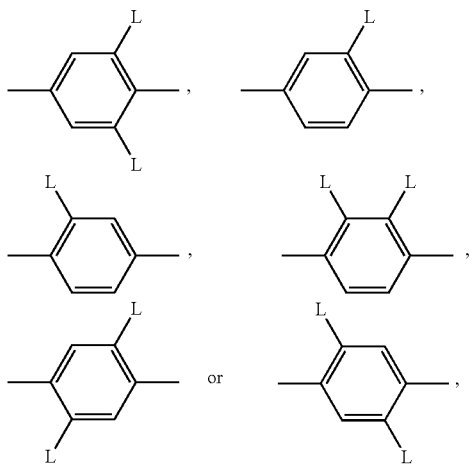

in which L has, on each occurrence identically or differently, one of the meanings given above and below, and is preferably F, Cl, CN, NO$_2$, CH$_3$, C$_2$H$_5$, C(CH$_3$)$_3$, CH(CH$_3$)$_2$, CH$_2$CH(CH$_3$)C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$ or P-Sp-, very preferably F, Cl, CN, CH$_3$, C$_2$H$_5$, OCH$_3$, COCH$_3$, OCF$_3$ or P-Sp-, most preferably F, Cl, CH$_3$, OCH$_3$, COCH$_3$ or OCF$_3$.

"Halogen" denotes F, Cl, Br or I, preferably F or Cl, more preferably F.

"Polymerisable groups" (P) are preferably selected from groups containing a C=C double bond or C≡C triple bond, and groups which are suitable for polymerisation with ring opening, such as, for example, oxetane or epoxide groups.

Preferably, polymerisable groups (P) are selected from the group consisting of CH$_2$=CW$^1$—COO—, CH$_2$=CW$^1$—CO—,

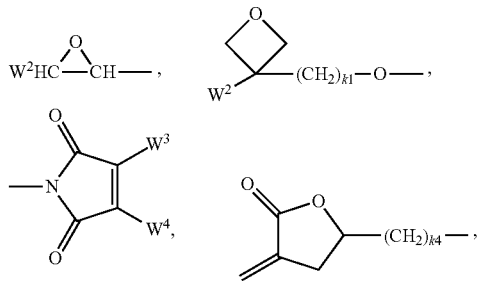

CH$_2$=CW$^2$—(O)$_{k3}$—, CW$^1$=CH—CO—(O)$_{k3}$—, CW$^1$=CH—CO—NH—, CH$_2$=CW$^1$—CO—NH—, CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, CH$_2$=CW$^1$—CO—NH—, CH$_2$=CH—(COO)$_{k1}$-Phe-(O)$_{k2}$—, CH$_2$=CH—(CO)$_{k1}$-Phe-(O)$_{k2}$—, Phe-CH=CH—, in which
W$^1$ denotes H, F, Cl, CN, CF$_3$, phenyl or alkyl having 1 to 5 C atoms, in particular H, F, Cl or CH$_3$,
W$^2$ denotes H or alkyl having 1 to 5 C atoms, in particular H, methyl, ethyl or n-propyl,
W$^3$ and W$^4$ each, independently of one another, denote H, Cl or alkyl having 1 to 5 C atoms, Phe denotes 1,4-phenylene, which is optionally substituted by one or more radicals L as being defined above but being different from P-Sp, preferably preferred substituents L are F, Cl, CN, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$, furthermore phenyl, and
$k_1$, $k_2$ and $k_3$ each, independently of one another, denote 0 or 1, $k_3$ preferably denotes 1, and $k_4$ is an integer from 1 to 10.

Particularly preferred polymerizable groups P are CH$_2$=CH—COO—, CH$_2$=C(CH$_3$)—COO—, CH$_2$=CF—COO—, CH$_2$=CH—, CH$_2$=CH—O—, (CH$_2$=CH)$_2$CH—OCO—, (CH$_2$=CH)$_2$CH—O—,

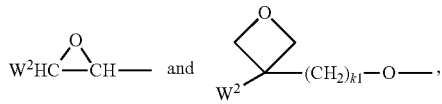

in which W$^2$ denotes H or alkyl having 1 to 5 C atoms, in particular H, methyl, ethyl or n-propyl, Further preferred polymerizable groups (P) are vinyloxy, acrylate, methacrylate, fluoroacrylate, chloroacrylate, oxetane and epoxide, most preferably acrylate or methacrylate, in particular acrylate.

All multireactive polymerisable compounds and sub-formulae thereof can optionally contain instead of one or more radicals P-Sp-, one or more branched radicals containing two or more polymerisable groups P (multireactive polymerisable radicals).

Suitable radicals of this type, and polymerisable compounds containing them, are described, for example, in U.S. Pat. No. 7,060,200 B1 or US 2006/0172090 A1.

Particular preference is given to multireactive polymerisable radicals selected from the following formulae:

| | |
|---|---|
| —X-alkyl-CHP$^x$—CH$_2$—CH$_2$P$^y$ | I*a |
| —X-alkyl-C(CH$_2$P$^x$)(CH$_2$P$^y$)—CH$_2$P$^z$ | I*b |
| —X-alkyl-CHP$^x$CHP$^y$—CH$_2$P$^z$ | I*c |
| —X-alkyl-C(CH$_2$P$^x$)(CH$_2$P$^y$)—C$_{aa}$H$_{2aa+1}$ | I*d |
| —X-alkyl-CHP$^x$—CH$_2$P$^y$ | I*e |
| —X-alkyl-CHP$^x$P$^y$ | I*f |
| —X-alkyl-CP$^x$P$^y$—C$_{aa}$H$_{2aa+1}$ | I*g |
| —X-alkyl-C(CH$_2$P$^y$)(CH$_2$P$^w$)—CH$_2$OCH$_2$—C(CH$_2$P$^x$)(CH$_2$Py)CH$_2$P$^z$ | I*h |
| —X-alkyl-CH((CH$_2$)$_{aa}$P$^x$)((CH$_2$)$_{bb}$P$^y$) | I*i |
| —X-alkyl-CHP$^x$CHP$^y$—C$_{aa}$H$_{2aa+1}$ | I*k | in which
alkyl denotes a single bond or straight-chain or branched alkylene having 1 to 12 C atoms, in which one or more non-adjacent CH$_2$ groups may each be replaced, independently of one another, by —C(R$^x$)=C(R$^x$)—, —C≡C—, —N(R$^x$)—, —O—, —S—, —CO—, —CO—O—, —O—CO—, —O—CO—O— in such a way that O and/or S atoms are not linked directly to one another, and in which, in addition, one or more H atoms may be replaced by F, Cl or CN, where R$^x$ has one the above-mentioned meaning,
$_{aa}$ and $_{bb}$ each, independently of one another, denote 0, 1, 2, 3, 4, 5 or 6,
X has one of the meanings indicated for X', and
P$^y$ to P$^z$ each, independently of one another, have one of the meanings indicated above for P.

Unless stated explicitly otherwise, preferred spacer groups Sp are selected from the formula Sp'—X', so that the radical "P-Sp-" conforms to the formula "P-Sp'—X'-", where
Sp' denotes alkylene having 1 to 20, preferably 1 to 12 C atoms, which is optionally mono- or polysubstituted by F, Cl, Br, I or CN and in which, in addition, one or more non-adjacent CH$_2$ groups may each be replaced, independently of one another, by —O—, —S—, —NH—, —NR$^{xx}$—, —SiR$^{xx}$R$^{yy}$—, —CO—, —COO—, —OCO—, —OCO—O—, —S—CO—, —CO—S—, —NR$^{xx}$—CO—O—, —O—CO—NR$^{Oxx}$—, —NR$^{xx}$—CO—NR$^{yy}$—, —CH=CH— or —C≡C— in such a way that 0 and/or S atoms are not linked directly to one another,
X' denotes —O—, —S—, —CO—, —COO—, —OCO—, —O—COO—, —CO—NR$^{xx}$—, —NR$^{xx}$—CO—, —NR$^{xx}$—CO—NR$^{yy}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^x$—, —CY$^{xx}$=CY$^{xx}$—, —C≡C—, —CH=CH—COO—, —OCO—CH=CH— or a single bond, R$^{xx}$ and R$^{yy}$ each, independently of one another, denote H or alkyl having 1 to 12 C atoms, and
Y$^{xx}$ and Y$^{yy}$ each, independently of one another, denote H, F, Cl or CN.

X' is preferably —O—, —S— —CO—, —COO—, —OCO—, —O—COO—, —CO—NR$^{xx}$—, —NR$^{xx}$—CO—, —NR$^{xx}$—CO—NR$^{yy}$— or a single bond.

Typical spacer groups Sp' are, for example, —(CH$_2$)$_{p1}$—, —(CH$_2$CH$_2$O)$_{q1}$—CH$_2$CH$_2$—, —CH$_2$CH$_2$—S—CH$_2$CH$_2$—, —CH$_2$CH$_2$—NH—CH$_2$CH$_2$— or —(SiR$^{xx}$R$^{yy}$—O)$_{p1}$—, in which p1 is an integer from 1 to 12, q1 is an integer from 1 to 3, and R$^{xx}$ and R$^{yy}$ have the above-mentioned meanings.

Particularly preferred groups —X'-Sp'- are —(CH$_2$)$_{p1}$—, —O—(CH$_2$)$_{p1}$—, —OCO—(CH$_2$)$_{p1}$—, —OCOO—(CH$_2$)$_{p1}$—, in which p1 is an integer from 1 to 12.

Particularly preferred groups Sp' are, for example, in each case straight-chain, methylene, ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

For the present invention,

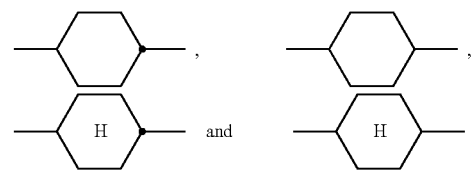

denote trans-1,4-cyclohexylene, and

denote 1,4-phenylene.

For the present invention the groups —COO— —C(=O)O— or —CO$_2$— denote an ester group of formula

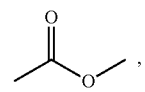

and the groups —OCO—, —OC(=O)—, —O$_2$C— or —OOC— denote an ester group of formula

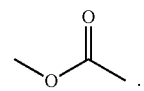

On the molecular level, the birefringence of a liquid crystal depends on the anisotropy of the polarizability ($\Delta\alpha=\alpha_\parallel-\alpha_\perp$). "Polarizability" means the ease with which the electron distribution in the atom or molecule can be distorted. The polarizability increases with greater number of electrons and a more diffuse electron cloud. The polarizability can be calculated using a method described in e.g. Jap. J. Appl. Phys. 42, (2003) p. 3463.

The "optical retardation" at a given wavelength R(λ) (in nm) of a layer of liquid crystalline or birefringent material is defined as the product of birefringence at that wavelength Δn(λ) and layer thickness d (in nm) according to the equation $$R(\lambda) = \Delta n(\lambda) \cdot d$$

The optical retardation R represents the difference in the optical path lengths in nanometres travelled by S-polarised and P-polarised light whilst passing through the birefringent material. "On-axis" retardation means the retardation at normal incidence to the sample surface.

The term "negative (optical) dispersion" refers to a birefringent or liquid crystalline material or layer that exhibits reverse birefringence dispersion where the magnitude of the birefringence (Δn) increases with increasing wavelength (λ). i.e. |Δn(450)|<|Δn(550)|, or Δn(450)/Δn(550)<1, where Δn(450) and Δn(550) are the birefringence of the material measured at wavelengths of 450 nm and 550 nm respectively. In contrast, positive (optical) dispersion" means a material or layer having |Δn(450)|>|Δn(550)| or Δn(450)/Δn(550)>1. See also for example A. Uchiyama, T. Yatabe "Control of Wavelength Dispersion of Birefringence for Oriented Copolycarbonate Films Containing Positive and Negative Birefringent Units". J. Appl. Phys. Vol. 42 pp 6941-6945 (2003). "Flat (optical) dispersion" means a material or layer having |Δn(450)|>|Δn(550)| or Δn(450)/Δn(550) ≈1.

Since the optical retardation at a given wavelength is defined as the product of birefringence and layer thickness as described above [R(λ)=Δn(λ)·d], the optical dispersion can be expressed either as the "birefringence dispersion" by the ratio Δn(450)/Δn(550), or as "retardation dispersion" by the ratio R(450)/R(550), wherein R(450) and R(550) are the retardation of the material measured at wavelengths of 450 nm and 550 nm respectively. Since the layer thickness d does not change with the wavelength, R(450)/R(550) is equal to Δn(450)/Δn(550). Thus, a material or layer with negative or reverse dispersion has R(450)/R(550)<1 or |R(450)|<|R(550)|, a material or layer with positive or normal dispersion has R(450)/R(550)>1 or |R(450)|>|R(550)|, and a material or layer with flat dispersion has R(450)/R(550)≈1 or |R(450)|≈|R(550)|.

In the present invention, unless stated otherwise "optical dispersion" means the retardation dispersion i.e. the ratio R(450)/R(550).

The term "high dispersion" means that the absolute value of the dispersion shows a large deviation from 1, whereas the term "low dispersion" means that the absolute value of the dispersion shows a small deviation from 1. Thus, for example, "high negative dispersion" means that the dispersion value is significantly smaller than 1, and "low negative dispersion" means that the dispersion value is only slightly smaller than 1.

The retardation (R(λ)) of a material can be measured using a spectroscopic ellipsometer, for example the M2000 spectroscopic ellipsometer manufactured by J. A. Woollam Co., This instrument is capable of measuring the optical retardance in nanometres of a birefringent sample e.g. Quartz over a range of wavelengths typically, 370 nm to 2000 nm. From this data it is possible to calculate the dispersion (R(450)/R(550) or Δn(450)/Δn(550)) of a material.

A method for carrying out these measurements was presented at the National Physics Laboratory (London, UK) by N. Singh in October 2006 and entitled "Spectroscopic Ellipsometry, Part1—Theory and Fundamentals, Part 2—Practical Examples and Part 3—measurements". In accordance with the measurement procedures described Retardation Measurement (RetMeas) Manual (2002) and Guide to W/ASE (2002) (Woollam Variable Angle Spectroscopic Ellipsometer) published by J. A. Woollam Co. Inc (Lincoln, NE, USA). Unless stated otherwise, this method is used to determine the retardation of the materials, films and devices described in this invention.

The term "A plate" refers to an optical retarder utilizing a layer of uniaxially birefringent material with its extraordinary axis oriented parallel to the plane of the layer.

The term "C plate" refers to an optical retarder utilizing a layer of uniaxially birefringent material with its extraordinary axis oriented perpendicular to the plane of the layer. In A/C-plates comprising optically uniaxial birefringent liquid crystal material with uniform orientation, the optical axis of the film is given by the direction of the extraordinary axis. An A (or C) plate comprising optically uniaxial birefringent material with positive birefringence is also referred to as "positive A (or C) plate" or "+A (or +C) plate". An A (or C) plate comprising a film of optically uniaxial birefringent material with negative birefringence, such as discotic anisotropic materials is also referred to as "negative A (or C) plate" or "−A (or C) plate" depending on the orientation of the discotic materials. A film made from a cholesteric calamitic material with a reflection band in the UV part of the spectrum also has the optics of a negative C plate.

The birefringence Δn is defined as follows $$\Delta n = n_e - n_o$$

wherein $n_e$ is the extraordinary refractive index and $n_o$ is the ordinary refractive index, and the effective average refractive index $n_{av.}$ is given by the following equation:

$$n_{av.} = ((2n_o^2 + n_e^2)/3)^{1/2}$$

The average refractive index $n_{av.}$ and the ordinary refractive index $n_o$ can be measured using an Abbe refractometer. Δn can then be calculated from the above equations.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components. On the other hand, the word "comprise" also encompasses the term "consisting of" but is not limited to it.

Throughout the description and claims of this specification, the words "obtainable" and "obtained" and variations of the words, mean "including but not limited to", and are not intended to (and do not) exclude other components. On the other hand, the word "obtainable" also encompasses the term "obtained" but is not limited to it.

All concentrations are quoted in percent by weight and relate to the respective mixture as a whole, all temperatures are quoted in degrees Celsius and all temperature differences are quoted in differential degrees.

BRIEF DESCRIPTION OF THE DRAWING FIGURES

DETAILED DESCRIPTION

Figure 1:
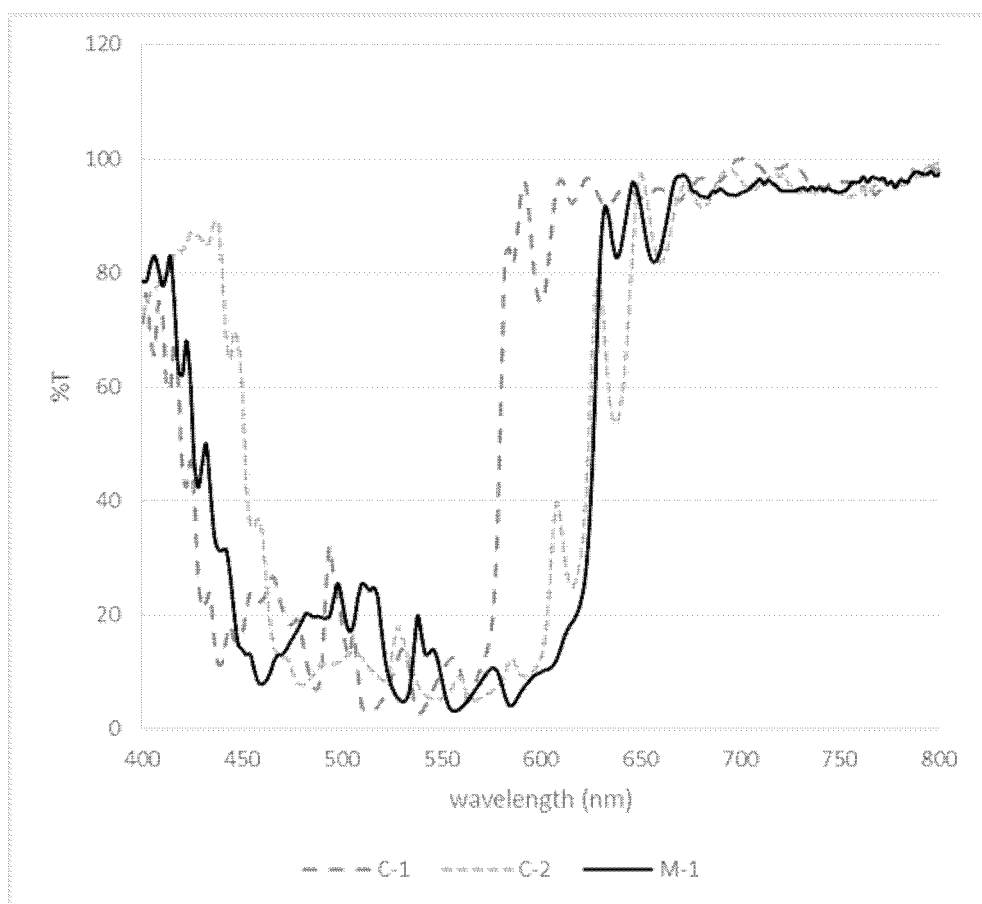
FIG. 1 is a plot of % T versus wavelength for Compound Example 1 (RM-1) according to the invention and comparative compounds C1 and C2.
Figure 2:
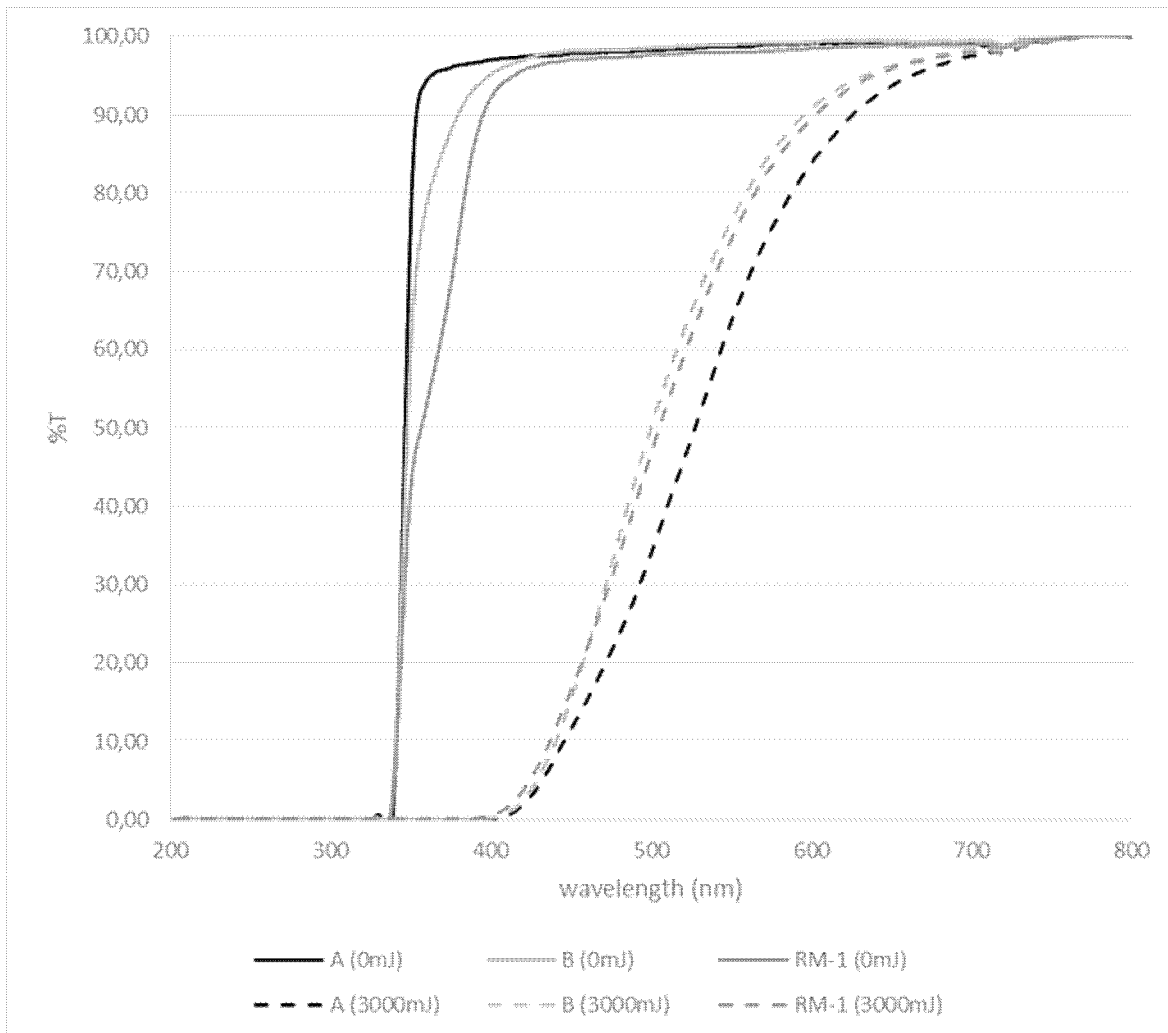
FIG. 2 is a plot of % T versus wavelength at 0 mJ and 3000 mJ for Compound Example 1 (RM-1) according to the invention and comparative compound A and B.

Preferred compounds of formula I are those wherein

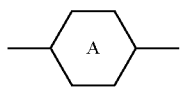

denotes a radical selected from the following groups:
a) a group consisting of 1,4-phenylene and 1,3-phenylene, wherein, in addition, one or two CH groups may be replaced by N and wherein, in addition, one or more H atoms may be replaced by L,
b) a group selected from the group consisting of

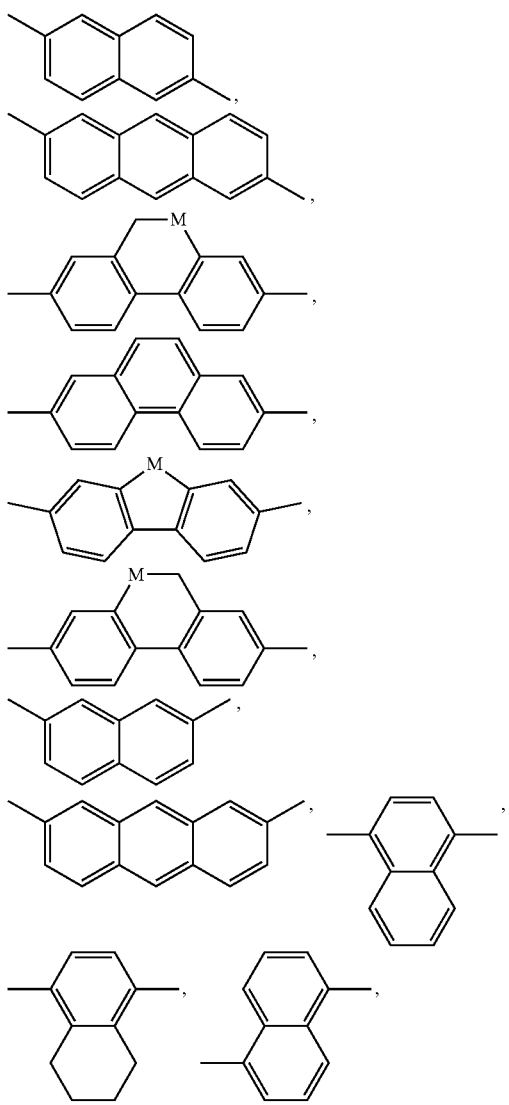

where, in addition, one or more H atoms in these radicals may be replaced by L, and/or one or more double bonds may be replaced by single bonds, and/or one or more CH groups may be replaced by N, c) group consisting of trans-1,4-cyclohexylene, 1,4-cyclohexenylene, wherein, in addition, one or more non-adjacent $CH_2$ groups may be replaced by —O— and/or —S— and wherein, in addition, one or more H atoms may be replaced by F, or
d) a group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may also be mono- or polysubstituted by L, and wherein
L on each occurrence, identically or differently, denotes —OH, —F, —Cl, —Br, —I, —CN, —$NO_2$, $SF_5$, —NCO, —NCS, —OCN, —SCN, —C(=O)N($R^z$)$_2$, —C(=O)$R^z$, —N($R^z$)$_2$, optionally substituted silyl, optionally substituted aryl having 6 to 20 C atoms, or straight-chain or branched or cyclic alkyl, alkoxy, alkylcarbonyl, alkoxycarbonyl, alkylcarbonyloxy or alkoxycarbonyloxy having 1 to 25 C atoms, preferably 1 to 12 C atoms, more preferably 1 to 6 C atoms, in which, in addition, one or more H atoms may be replaced by F or C.

Further preferred compounds of formula I are those wherein

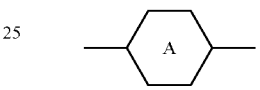

denotes a radical selected from a group consisting of 1,4-phenylene, wherein, in addition, one or two CH groups may be replaced by N and wherein, in addition, one or more H atoms may be replaced by L, wherein
L on each occurrence, identically or differently, denotes —OH, —F, —Cl, or straight-chain, branched or cyclic alkyl, alkoxy, alkylcarbonyl, alkoxycarbonyl, alkylcarbonyloxy or alkoxycarbonyloxy having 1 to 25 C atoms, preferably 1 to 12 C atoms, more preferably 1 to 6 C atoms, in which, in addition, one or more H atoms may be replaced by F or C.

Further preferred compounds of formula I are those of the following table:

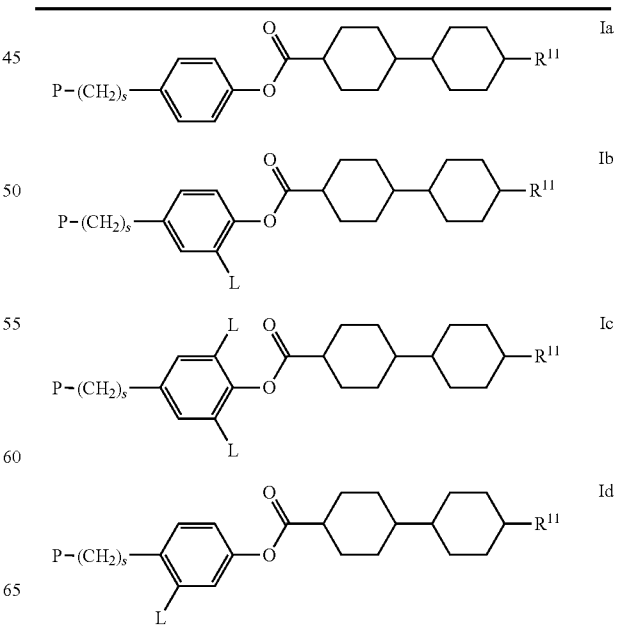

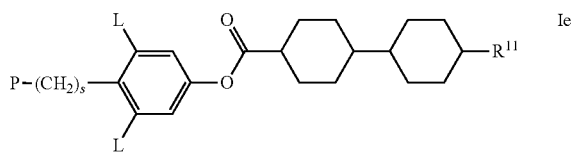

wherein
P is a polymerisable group,
  preferably a methacrylic or acrylic group,
s denotes an integer between 0 and 9, preferably an integer between 1 and 7, such as methylene, ethylene, propylene, butylene, pentylene, hexylene, heptylene, $R^{11}$ is alkyl, alkoxy, thioalkyl, alkylcarbonyl, alkoxycarbonyl, alkylcarbonyloxy or alkoxycarbonyloxy preferably with 1 to 15 C atoms which is more preferably optionally fluorinated,
  preferably alkyl with 1 to 12 C atoms,
L on each occurrence, identically or differently, denotes —OH, —F, —Cl, or straight-chain, branched or cyclic alkyl, alkoxy, alkylcarbonyl, alkoxycarbonyl, alkylcarbonyloxy or alkoxycarbonyloxy having 1 to 12 C atoms, more preferably 1 to 6 C atoms, in which, in addition, one or more H atoms may be replaced by F or Cl,
  preferably F, Cl, methyl, ethyl, propyl, methoxy, ethoxy, propoxy, or OH.

Further preferred compounds of formula I are those of the following table:

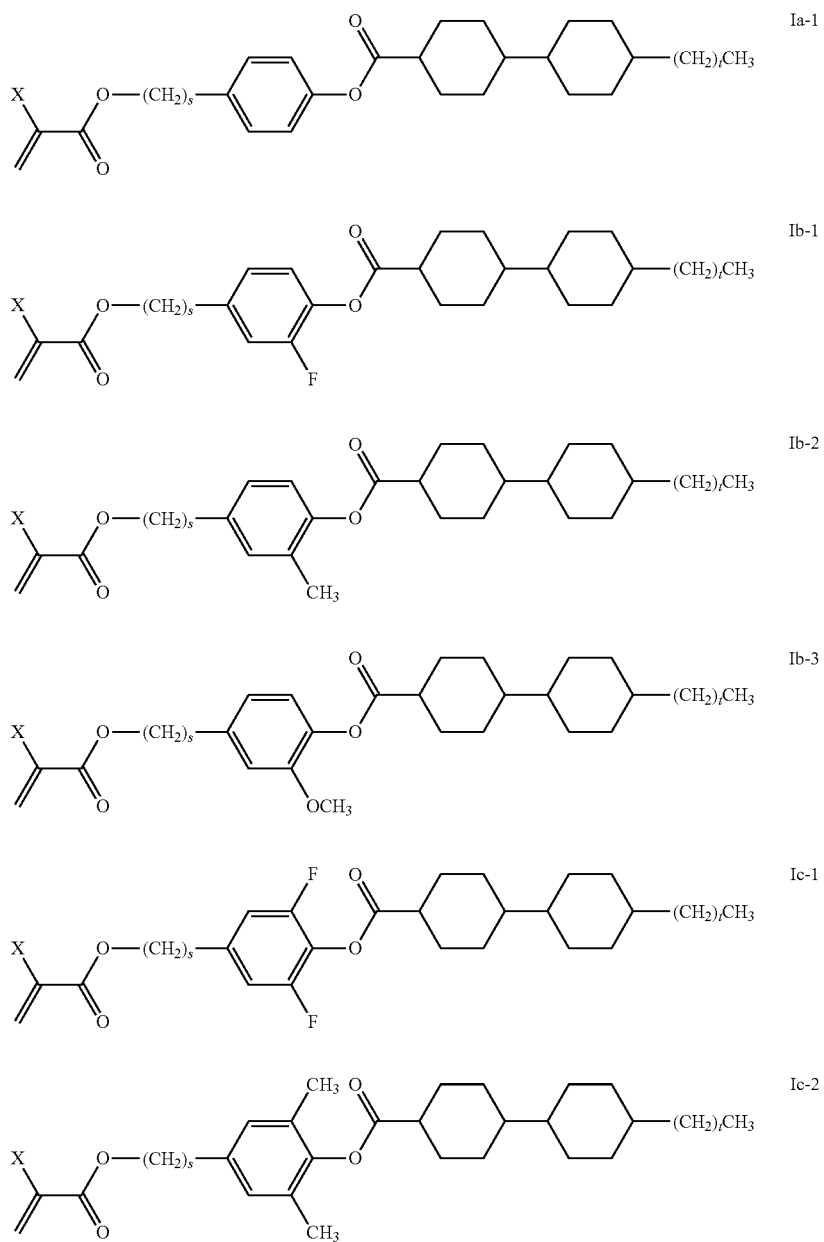

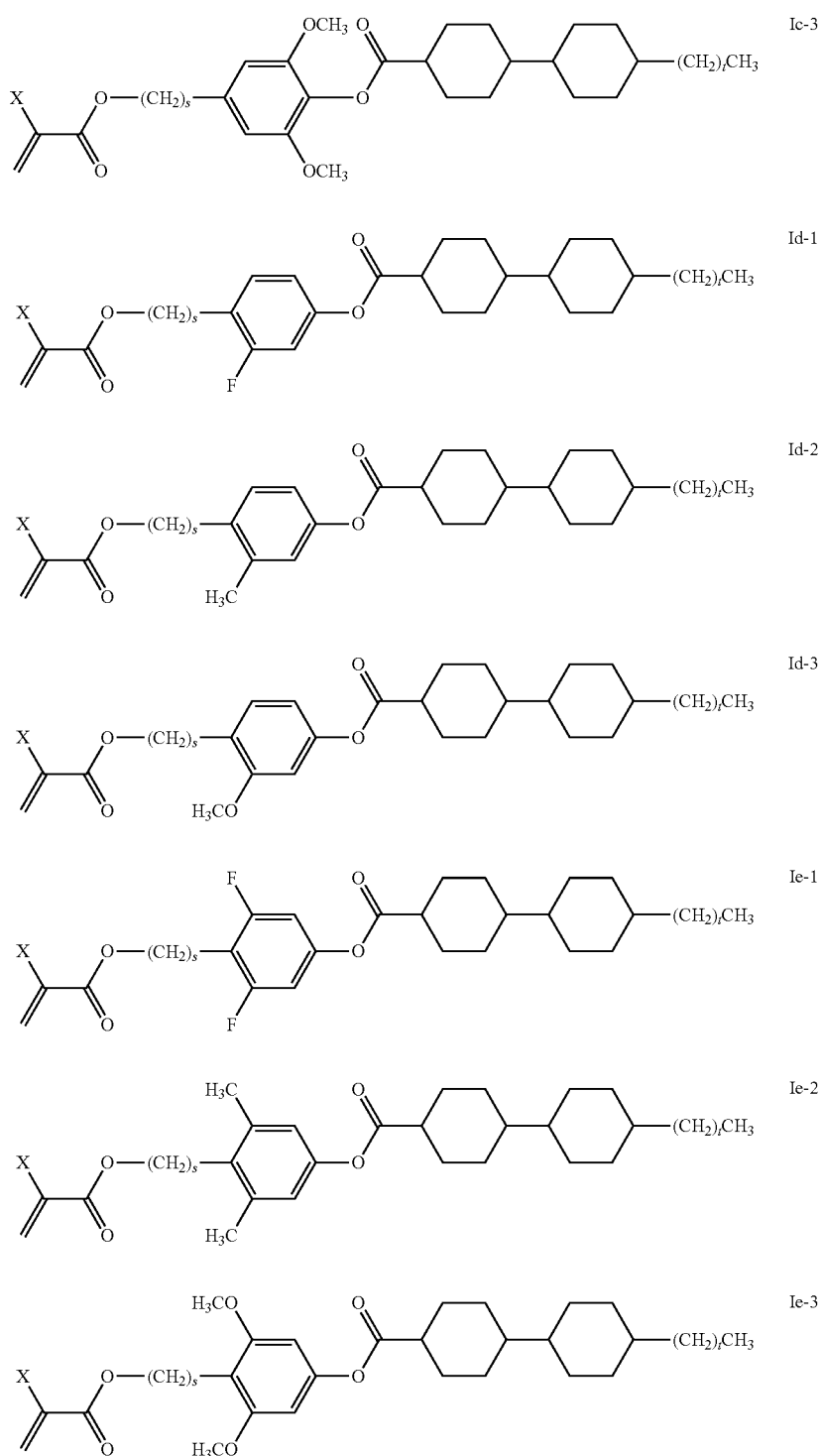
wherein
X denotes H or —CH₃,
s denotes 0, 1, 2, 3, 4, 5, 6 or 7, preferably 5, 6 or 7, and
t denotes 0, 1, 2, 3, 4 or 5, preferably 2, 3, 4 or 5.

The synthesis of the compounds of formula I and its subformulae can be carried out analogously to the illustrative reactions shown below or in the examples. The preparation of further compounds according to the invention can also be carried out by other methods known per se to the person skilled in the art from the literature.

Exemplarily, the compounds of formula I can be synthesized according to or in analogy to the methods as illustrated in Scheme 1.

Scheme 1

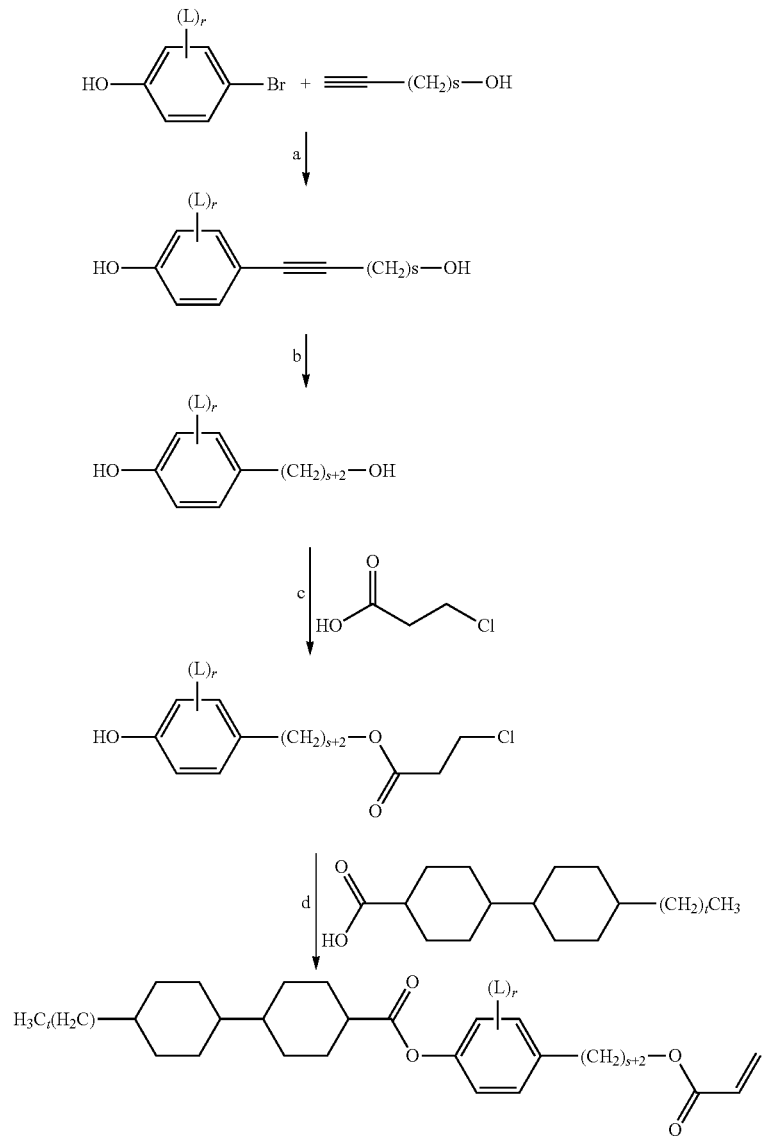

Conditions:
Step a.1: Diisopropylamine, CuI, Pd(OAc)$_2$, [(t-Bu)$_3$PH] BF$_4$, 40° C., 4 h.
Step a.2: HCl(aq), Ice.
Step b: H$_2$, Pd(0) on carbon (10%), THF, rt, 7 h.
Step c: p-toluenesulphonic acid, toluene, reflux, 3 h,
Step d.1: DMAP, DCC, DCM, rt, 12 h.
Step d.2: Et$_3$N, 40° C., 8 h.
Step d.3: HCl, 0° C., 30 min.

and wherein the parameter s, t and L have one of the meanings as given in formula I and r denotes 0, 1, or 2.

Another object of the invention is an polymerizable LC or RM mixture comprising two or more RMs, at least one of which is a compound of formula I.

Preferably the RM mixture comprises one or more RMs having only one polymerisable functional group (monoreactive RMs), at least one of which is a compound of formula I, and one or more RMs having two or more polymerisable functional groups (di- or multireactive RMs).

The di- or multireactive RMs are preferably selected of formula DRM

P¹-Sp¹-MG-Sp²-P²  DRM wherein
P¹ and P² independently of each other denote a polymerisable group,
Sp¹ and Sp² independently of each other are a spacer group or a single bond, and
MG is a rod-shaped mesogenic group, which is preferably selected of formula MG -(A¹-Z¹)$_n$-A²-  MG wherein
A¹ and A² denote, in case of multiple occurrence independently of one another, an aromatic or alicyclic group, which optionally contains one or more heteroatoms selected from N, O and S, and is optionally mono- or polysubstituted by L,
L is P-Sp-, F, Cl, Br, I, —CN, —NO$_2$, —NCO, —NCS, —OCN, —SCN, —C(=O)NR$^x$R$^y$, —C(=O)OR$^x$, —C(=O)R$^x$, —NR$^x$R$^y$, —OH, —SF$_5$, optionally substituted silyl, aryl or heteroaryl with 1 to 12, preferably 1 to 6 C atoms, and straight chain or branched alkyl, alkoxy, alkylcarbonyl, alkoxycarbonyl, alkylcarbonyloxy or alkoxycarbonyloxy with 1 to 12, preferably 1 to 6 C atoms, wherein one or more H atoms are optionally replaced by F or Cl,
R$^x$ and R$^y$ independently of each other denote H or alkyl with 1 to 12 C-atoms,
Z¹ denotes, in case of multiple occurrence independently of one another, —O—, —S—, —CO—, —COO—, —OCO—, —S—CO—, —CO—S—, —O—COO—, —CO—NR$^{00}$—, —NR$^{00}$—CO—, —NR$^{00}$—CO—NR$^{00}$, —NR$^{00}$—CO—O—, —O—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_{n1}$—, —CF$_2$CH$_2$—, —CH$_2$CF$_2$—, —CF$_2$CF$_2$—, —CH=N—, —N=CH—, —N=N—, —CH=CR$^0$—, —CY¹=CY²—, —C≡C—, —CH=CH—COO—, —OCO—CH=CH— or a single bond, preferably —COO—, —OCO— or a single bond,
Y¹ and Y² independently of each other denote H, F, Cl or CN,
n is 1, 2, 3 or 4, preferably 1 or 2, most preferably 2,
n1 is an integer from 1 to 10, preferably 1, 2, 3 or 4.

Preferred groups A¹ and A² include, without limitation, furan, pyrrol, thiophene, oxazole, thiazole, thiadiazole, imidazole, phenylene, cyclohexylene, bicyclooctylene, cyclohexenylene, pyridine, pyrimidine, pyrazine, azulene, indane, fluorene, naphthalene, tetrahydronaphthalene, anthracene, phenanthrene and dithienothiophene, all of which are unsubstituted or substituted by 1, 2, 3 or 4 groups L as defined above.

Particular preferred groups A¹ and A² are selected from 1,4-phenylene, pyridine-2,5-diyl, pyrimidine-2,5-diyl, thiophene-2,5-diyl, naphthalene-2,6-diyl, 1,2,3,4-tetrahydronaphthalene-2,6-diyl, indane-2,5-diyl, bicyclooctylene or 1,4-cyclohexylene wherein one or two non-adjacent CH$_2$ groups are optionally replaced by O and/or S, wherein these groups are unsubstituted or substituted by 1, 2, 3 or 4 groups L as defined above.

Preferred RMs of formula DRM are selected of formula DRMa

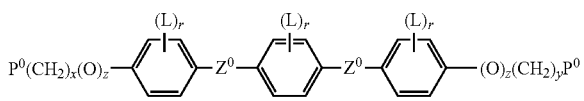

DRMa wherein
P⁰ is, in case of multiple occurrence independently of one another, a polymerisable group, preferably an acryl, methacryl, oxetane, epoxy, vinyl, heptadiene, vinyloxy, propenyl ether or styrene group,
Z⁰ is —COO—, —OCO—, —CH$_2$CH$_2$—, —CF$_2$O—, —OCF$_2$—, —C≡C—, —CH=CH—, —OCO—CH=CH—, —CH=CH—COO—, or a single bond,
L has on each occurrence identically or differently one of the meanings given for L¹ in formula I, and is preferably, in case of multiple occurrence independently of one another, selected from F, Cl, CN or optionally halogenated alkyl, alkoxy, alkylcarbonyl, alkoxycarbonyl, alkylcarbonyloxy or alkoxycarbonyloxy with 1 to 5 C atoms,
r is 0, 1, 2, 3 or 4,
x and y are independently of each other 0 or identical or different integers from 1 to 12,
z is 0 or 1, with z being 0 if the adjacent x or y is 0.

Very preferred RMs of formula DRM are selected from the following formulae:

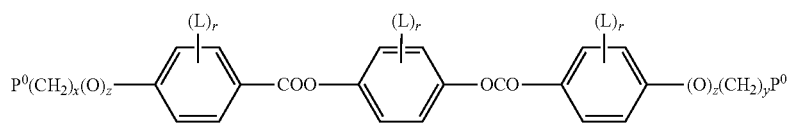

DRMa1

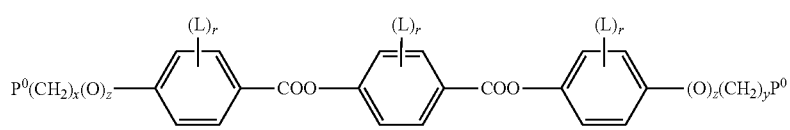

DRMa2

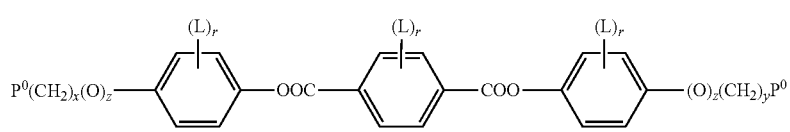

DRMa3

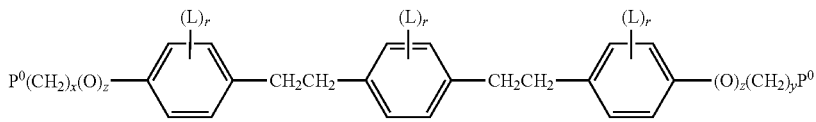
DRMa4

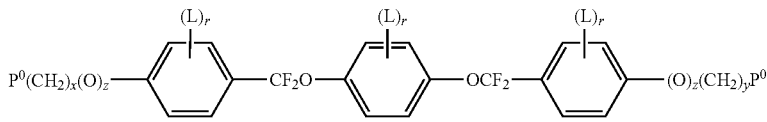
DRMa5

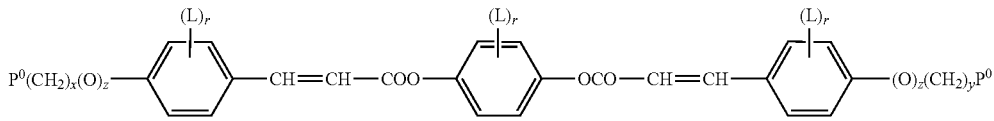
DRMa6

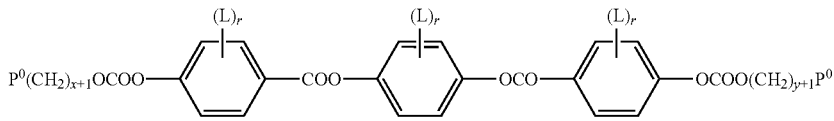
DRMa7

DRMb

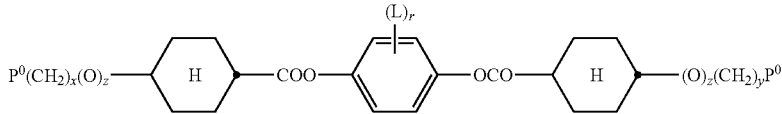
DRMc

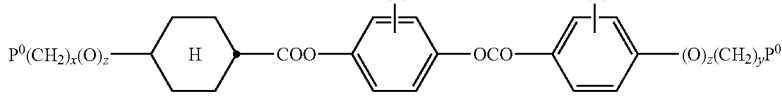
DRMd

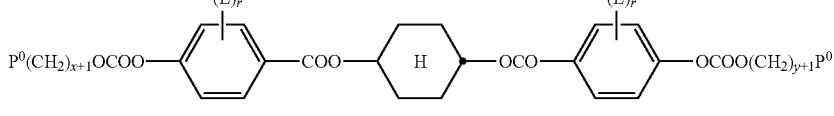
DRMe wherein $P^0$, L, r, x, y and z are as defined in formula DRMa.

Especially preferred are compounds of formula DRMa1, DRMa2 and DRMa3, in particular those of formula DRMa1.

The concentration of di- or multireactive RMs, preferably those of formula DRM and its subformulae, in the RM mixture is preferably from 1% to 60%, very preferably from 5 to 50%.

In another preferred embodiment the RM mixture comprises, in addition to the compounds of formula I, one or more monoreactive RMs. These additional monoreactive RMs are preferably selected from formula MRM:

$P^1$—Sp$^1$-MG-R      MRM wherein $P^1$, Sp$^1$ and MG have the meanings given in formula DRM, R denotes P-Sp-, F, Cl, Br, I, —CN, —NO$_2$, —NCO, —NCS, —OCN, —SCN, —C(=O)NR$^x$R$^y$, —C(=O)X, —C(=O)OR$^x$, —C(=O)R$^y$, —NR$^x$R$^y$, —OH, —SF$_5$, optionally substituted silyl, straight chain or branched alkyl, alkoxy, alkylcarbonyl, alkoxycarbonyl, alkylcarbonyloxy or alkoxycarbonyloxy with 1 to 12, preferably 1 to 6 C atoms, wherein one or more H atoms are optionally replaced by F or Cl, X is halogen, preferably F or Cl, and R$^x$ and R$^y$ are independently of each other H or alkyl with 1 to 12 C-atoms.

Preferably the RMs of formula MRM are selected from the following formulae.

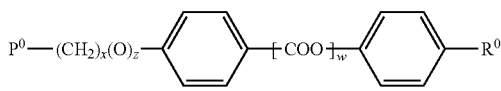
MRM1

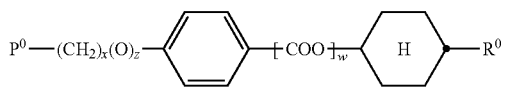
MRM2

-continued
MRM3
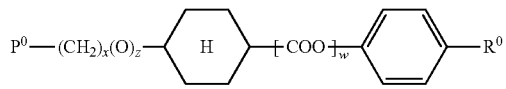
MRM4
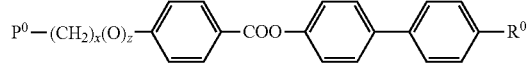
MRM5
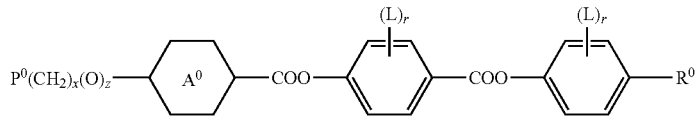
MRM6
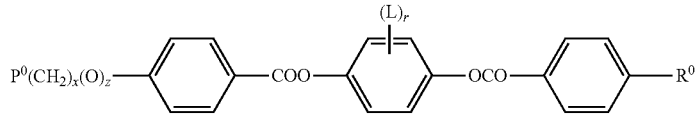
MRM7
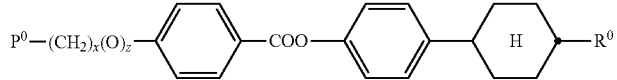
MRM8
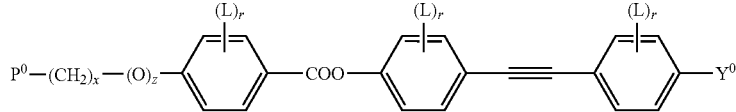
MRM9
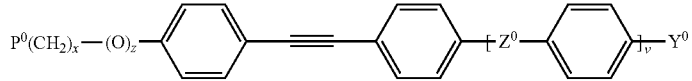
MRM10
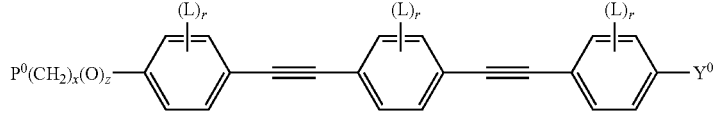
MRM11
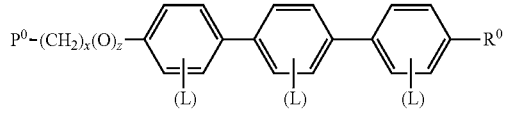
MRM12
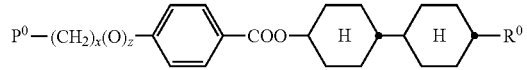
MRM13
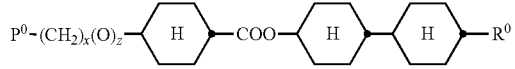
MRM14
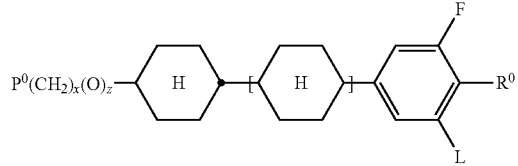
MRM15
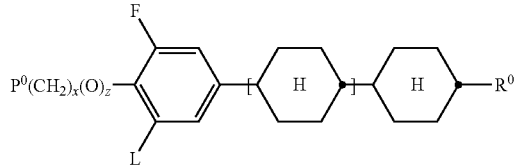
MRM16
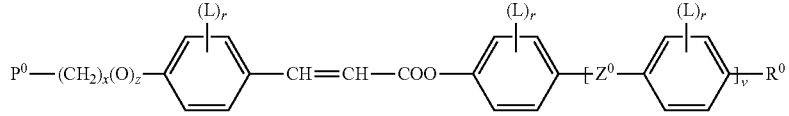
MRM17
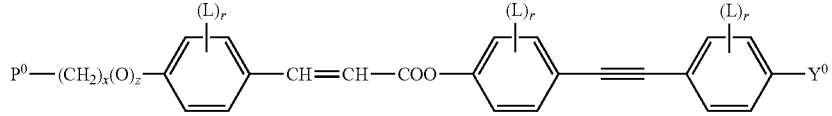

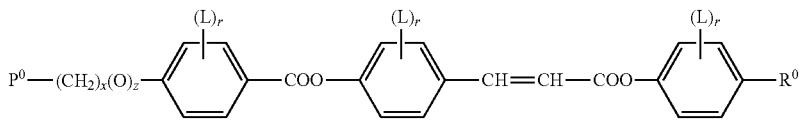
MRM18

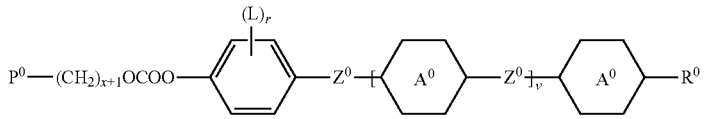
MRM19

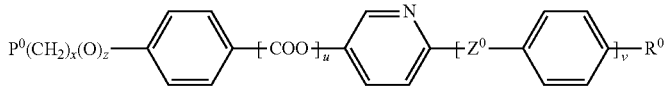
MRM20

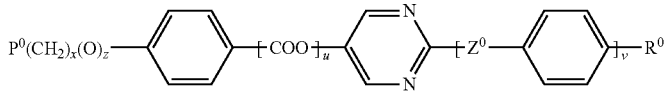
MRM21

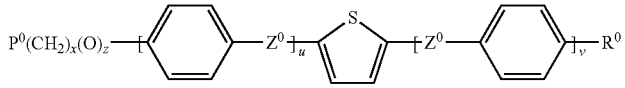
MRM22

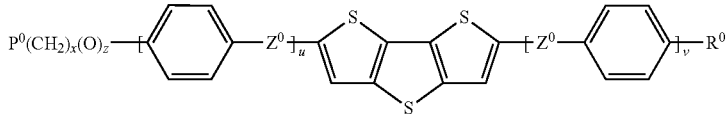
MRM23

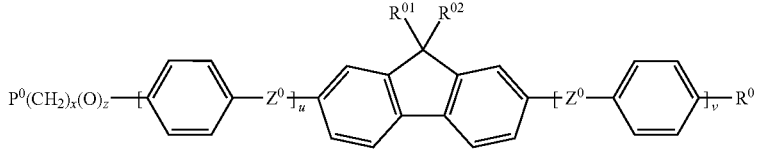
MRM24

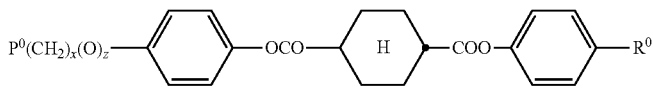
MRM25

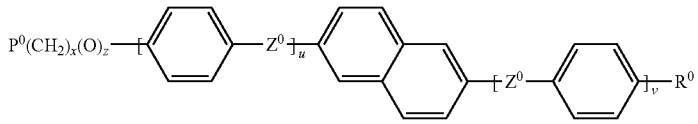
MRM26

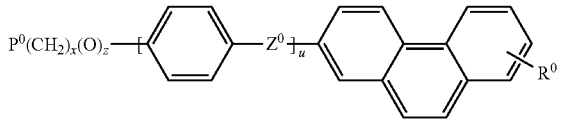
MRM27 wherein $P^0$, L, r, x, y and z are as defined in formula DRMa,
$R^0$ is alkyl, alkoxy, thioalkyl, alkylcarbonyl, alkoxycarbonyl, alkylcarbonyloxy or alkoxycarbonyloxy with 1 or more, preferably 1 to 15 C atoms or denotes $Y^0$ or $P-(CH_2)_y-(O)_z-$,
$X^0$ is $-O-$, $-S-$, $-CO-$, $-COO-$, $-OCO-$, $-O-COO-$, $-CO-NR^{01}-$, $-NR^{01}-CO-$, $-NR^{01}-CO-NR^{01}-$, $-OCH_2-$, $-CH_2O-$, $-SCH_2-$, $-CH_2S-$, $-CF_2O-$, $-OCF_2-$, $-CF_2S-$, $-SCF_2-$, $-CF_2CH_2-$, $-CH_2CF_2-$, $-CF_2CF_2-$, $-CH=N-$, $-N=CH-$, $-N=N-$, $-CH=CR^{01}-$, $-CF=CF-$, $-C\equiv C-$, $-CH=CH-COO-$, $-OCO-CH=CH-$ or a single bond $Y^0$ is F, Cl, CN, $NO_2$, $OCH_3$, OCN, SCN, $SF_5$, or mono- oligo- or polyfluorinated alkyl or alkoxy with 1 to 4 C atoms,
$Z^0$ is $-COO-$, $-OCO-$, $-CH_2CH_2-$, $-CF_2O-$, $-OCF_2-$, $-CH=CH-$, $-OCO-CH=CH-$, $-CH=CH-COO-$, or a single bond,
$A^0$ is, in case of multiple occurrence independently of one another, 1,4-phenylene that is unsubstituted or substituted with 1, 2, 3 or 4 groups L, or trans-1,4-cyclohexylene,
$R^{01,02}$ are independently of each other H, $R^0$ or $Y^0$,
u and v are independently of each other 0, 1 or 2,
w is 0 or 1,
and wherein the benzene and naphthalene rings can additionally be substituted with one or more identical or different groups L, and z in formula MRM15 denotes 1.

Especially preferred are compounds of formula MRM1, MRM2, MRM3, MRM4, MRM5, MRM6, MRM7, MRM9 and MRM10, in particular those of formula MRM1, MRM4, MRM6, and MRM7.

The concentration of all monoreactive RMs, including those of formula I, in the RM mixture is preferably from 1 to 80%, very preferably from 5 to 20%.

In formulae DRM, MRM and their preferred subformulae, L is preferably selected from F, Cl, CN, $NO_2$ or straight chain or branched alkyl, alkoxy, alkylcarbonyl, alkoxycarbonyl, alkylcarbonlyoxy or alkoxycarbonyloxy with 1 to 12 C atoms, wherein the alkyl groups are optionally perfluorinated, or P-Sp-.

Very preferably L is selected from F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F5$ or P-Sp-, in particular F, Cl, CN, $CH_3$, $C_2H_5$, $C(CH_3)_3$, $CH(CH_3)_2$, $OCH_3$, $COCH_3$ or $OCF_3$, most preferably F, Cl, $CH_3$, $C(CH_3)_3$, $OCH_3$ or $COCH_3$, or P-Sp-.

A substituted benzene ring of the formula

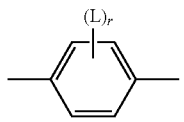

is preferably

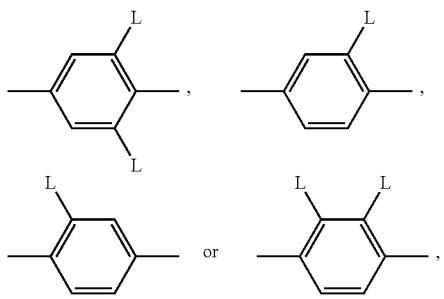

with L having each independently one of the meanings given above.

In formulae I, DRM, MRM and their preferred subformulae, an alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

An alkyl group wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1 E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1 E-alkenyl, $C_4$-$C_7$-3E-alkenyl and $C_5$-$C_7$-4-alkenyl. Examples for particularly preferred alkenyl groups are vinyl, 1 E-propenyl, 1 E-butenyl, 1 E-pentenyl, 1 E-hexenyl, 1 E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

In an alkyl group wherein one $CH_2$ group is replaced by —O— and one by —CO—, these radicals are preferably neighboured. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

An alkyl or alkenyl group that is monosubstituted by CN or $CF_3$ is preferably straight-chain. The substitution by CN or $CF_3$ can be in any desired position.

An alkyl or alkenyl group that is at least monosubstituted by halogen is preferably straight-chain. Halogen is preferably F or Cl, in case of multiple substitution preferably F. The resulting groups include also perfluorinated groups. In case of monosubstitution the F or $C_1$ substituent can be in any desired position, but is preferably in co-position. Examples for especially preferred straight-chain groups with a terminal F substituent are fluoromethyl, 2-fluoroethyl, 3-fluoropropyl, 4-fluorobutyl, 5-fluoropentyl, 6-fluorohexyl and 7-fluoroheptyl. Other positions of F are, however, not excluded.

$R^x$ and $R^y$ are preferably selected from H, straight-chain or branched alkyl with 1 to 12 C atoms.

—$CY^1$=$CY^2$— is preferably —CH=CH—, —CF=CF— or —CH=C(CN)—.

Halogen is F, Cl, Br or I, preferably F or Cl.

R, $R^0$, $R^1$, $R^2$ and $R^{11}$ can be an achiral or a chiral group. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), isopropoxy, 2-methyl-propoxy and 3-methylbutoxy.

In a further preferred embodiment, especially for negative optical dispersion applications, the polymerisable LC material as described above comprises additionally one or more compounds of formula ND,

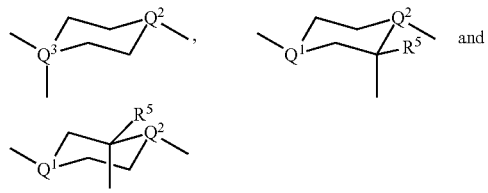

ND wherein
$U^{1,2}$ are independently of each other selected from

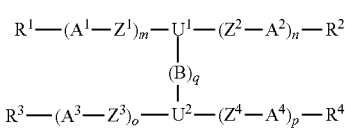

including their mirror images, wherein the rings $U^1$ and $U^2$ are each bonded to the group $-(B)_q-$ via the axial bond, and one or two non-adjacent $CH_2$ groups in these rings are optionally replaced by O and/or S,
$Q^{1,2}$ are independently of each other CH or SiH,
$Q^3$ is C or Si,
B is in each occurrence independently of one another $-C\equiv C-$, $-CY^1=CY^2-$ or an optionally substituted aromatic or heteroaromatic group,
$Y^{1,2}$ are independently of each other H, F, Cl, CN or $R^0$,
q is an integer from 1 to 10, preferably 1, 2, 3, 4, 5, 6 or 7,
$A^{1-4}$ are independently of each other selected from non-aromatic, aromatic or heteroaromatic carbocyclic or heterocyclic groups, which are optionally substituted by one or more groups $R^5$, and wherein each of $-(A^1-Z^1)_m-U^1-(Z^2-A^2)_n-$ and $-(A^3-Z^3)_o-U^2-(Z^4-A^4)_p-$ does not contain more aromatic groups than non-aromatic groups and preferably does not contain more than one aromatic group,
$Z^{1-4}$ are independently of each other $-O-$, $-S-$, $-CO-$, $-COO-$, $-OCO-$, $-O-COO-$, $-CO-NR^0-$, $-NR^0-CO-$, $-NR^0-CO-NR^0-$, $-OCH_2-$, $-CH_2O-$, $-SCH_2-$, $-CH_2S-$, $-CF_2O-$, $-OCF_2-$, $-CF_2S-$, $-SCF_2-$, $-CH_2CH_2-$, $-(CH_2)_3-$, $-(CH_2)_4-$, $-CF_2CH_2-$, $-CH_2CF_2-$, $-CF_2CF_2-$, $-CH=CH-$, $-CY^1=CY^2-$, $-CH=N-$, $-N=CH-$, $-N=N-$, $-CH=CR^0-$, $-C\equiv C-$, $-CH=CH-COO-$, $-OCO-CH=CH-$, $CR^0R^{00}$ or a single bond,
$R^0$ and $R^{00}$ are independently of each other H or alkyl with 1 to 12 C-atoms,
m and n are independently of each other 0, 1, 2, 3 or 4,
and p are independently of each other 0, 1, 2, 3 or 4,
$R^{1-5}$ are independently of each other identical or different groups selected from H, halogen, $-CN$, $-NC$, $-NCO$, $-NCS$, $-OCN$, $-SCN$, $-C(=O)NR^0R^{00}$, $-C(=O)X^0$, $-C(=O)R^0$, $-NH_2$, $-NR^0R^{00}$, $-SH$, $-SR^0$, $-SO_3H$, $-SO_2R^0$, $-OH$, $-NO_2$, $-CF_3$, $-SF_5$, P-Sp-, optionally substituted silyl, or carbyl or hydrocarbyl with 1 to 40 C atoms that is optionally substituted and optionally comprises one or more hetero atoms, or denote P or P-Sp-, or are substituted by P or P-Sp-, wherein the compounds comprise at least one group $R^{1-5}$ denoting or being substituted by P or P-Sp-,
P is a polymerisable group,
Sp is a spacer group or a single bond.

Preferably, the subgroups forming the bridging group B in formula ND are preferably selected from groups having a bonding angle of 120° or more, preferably in the range of 180°. Very preferred are $-C\equiv C-$ groups or divalent aromatic groups connected to their adjacent groups in para-position, like e.g. 1,4-phenylene, naphthalene-2,6-diyl, indane-2,6-diyl or thieno[3,2-b]thiophene-2,5-diyl.

Further possible subgroups include $-CH=CH-$, $-CY^1=CY^2-$, $-CH=N-$, $-N=CH-$, $-N=N-$ and $-CH=CR^0-$ wherein $Y^1$, $Y^2$, $R^0$ have the meanings given above.

Preferably the bridging group, or $-(B)_q-$ in formula ND, comprises one or more groups selected from the group consisting of $-C\equiv C-$, optionally substituted 1,4-phenylene and optionally substituted 9H-fluorene-2,7-diyl. The subgroups, or B in formula ND, are preferably selected from the group consisting of $-C\equiv C-$, optionally substituted 1,4-phenylene and optionally substituted 9H-fluorene-2,7-diyl, wherein in the fluorene group the H-atom in 9-position is optionally replaced by a carbyl or hydrocarbyl group.

Very preferably the bridging group, or $-(B)_q-$ in formula ND, are selected from $-C\equiv C-$, $-C\equiv C-C\equiv C-$, $-C\equiv C-C\equiv C-C\equiv C-$, $-C\equiv C-C\equiv C-C\equiv C-C\equiv C-$,

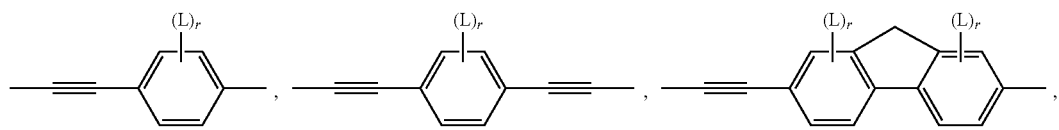

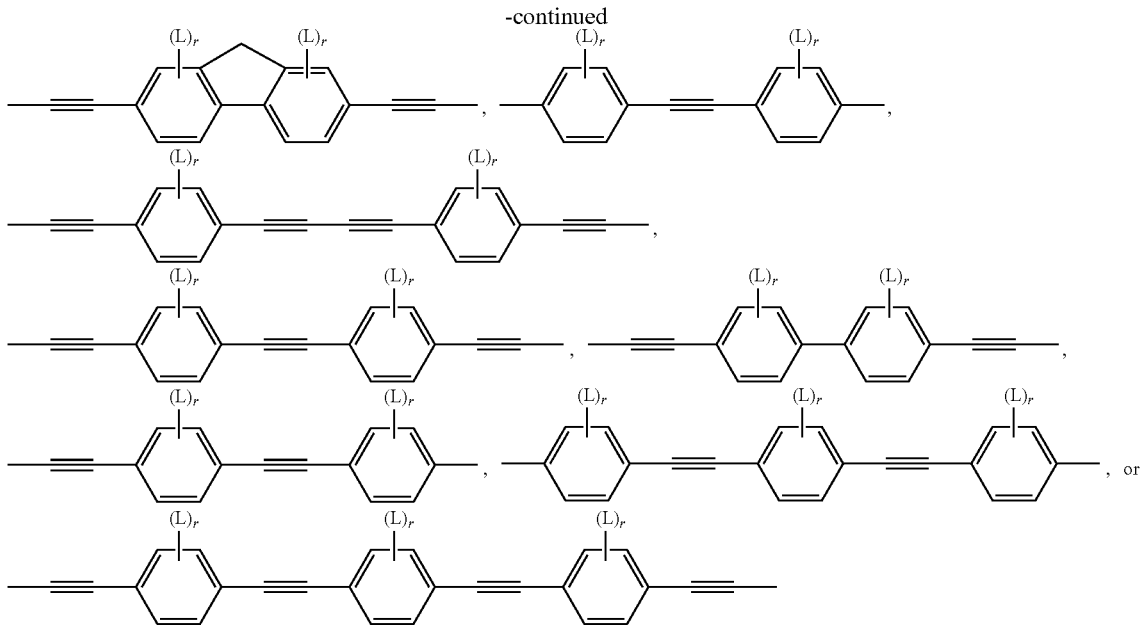

wherein r is 0, 1, 2, 3 or 4 and L has the meaning as described below.

Preferably, the non-aromatic rings of the mesogenic groups where the bridging group is attached, like $U^1$ and $U^2$ in formula ND, are preferably selected from

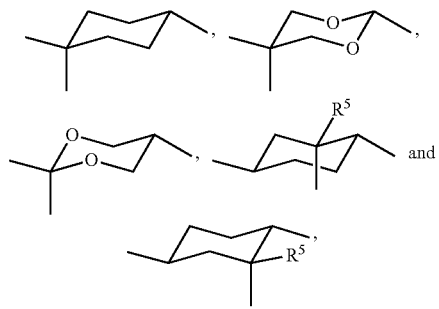

wherein $R^5$ is as defined in formula ND.

Preferably, the aromatic groups $A^{1-4}$ in formula ND, may be mononuclear, i.e. having only one aromatic ring (like for example phenyl or phenylene), or polynuclear, i.e. having two or more fused rings (like for example napthyl or naphthylene). Especially preferred are mono-, bi- or tricyclic aromatic or heteroaromatic groups with up to 25 C atoms that may also comprise fused rings and that are optionally substituted.

Preferably, the non-aromatic carbocyclic and heterocyclic rings $A^{1-4}$ in the compounds of formula ND, include those which are saturated (also referred to as "fully saturated"), i.e. they do only contain C-atoms or hetero atoms connected by single bonds, and those which are unsaturated (also referred to as "partially saturated"), i.e. they also comprise C-atoms or hetero atoms connected by double bonds. The non-aromatic rings may also comprise one or more hetero atoms, preferably selected from Si, O, N and S.

Preferably the non-aromatic and aromatic rings, or $A^{1-4}$ in formula ND, are selected from trans-1,4-cyclohexylene and 1,4-phenylene that is optionally substituted with one or more groups L.

Very preferred are compounds of formula ND, wherein m and p are 1 and n and o are 1 or 2. Further preferred are compounds of formula ND, wherein m and p are 1 or 2 and n and o are 0. Further preferred are compounds wherein m, n, o and p are 2.

In the compounds of formula ND, the linkage groups connecting the aromatic and non-aromatic cyclic groups in the mesogenic groups, or $Z^{1-4}$, are preferably selected from —O—, —S—, —CO—, —COO—, —OCO—, —O—COO—, —CO—NR$^0$—, —NR$^0$—CO—, —NR$^0$—CO—NR$^0$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_3$—, —(CH$_2$)$_4$—, —CF$_2$CH$_2$—, —CH$_2$CF$_2$—, —CF$_2$CF$_2$—, —CH=CH—, —CY$^1$=CY$^2$—, —CH=N—, —N=CH—, —N=N—, —CH=CR$^0$—, —C≡C—, —CH=CH—COO—, —OCO—CH=CH—, CR$^0$R$^{00}$ or a single bond, very preferably from —COO—, —OCO— and a single bond.

Preferably, in the compounds of formula ND, the substituents on the rings, such as L, are preferably selected from P-Sp-, F, Cl, Br, I, —CN, —NO$_2$, —NCO, —NCS, —OCN, —SCN, —C(=O)NR$^0$R$^{00}$, —C(=O)X, —C(=O)OR$^0$, —C(=O)R$^0$, —NR$^0$R$^{00}$, —OH, —SF$_5$, optionally substituted silyl, aryl or heteroaryl with 1 to 12, preferably 1 to 6 C atoms, and straight chain or branched alkyl, alkoxy, alkylcarbonyl, alkoxycarbonyl, alkylcarbonyloxy or alkoxycarbonyloxy with 1 to 12, preferably 1 to 6 C atoms, wherein one or more H atoms are optionally replaced by F or Cl, wherein $R^0$ and $R^{00}$ are as defined in formula ND and X is halogen.

Preferably, the compounds of formula ND comprise one or more terminal groups, like $R^{1-4}$, or substituents, like $R^5$, that are substituted by two or more polymerisable groups P or P-Sp- (multifunctional polymerisable groups). Suitable multifunctional polymerisable groups of this type are disclosed for example in U.S. Pat. No. 7,060,200 B1 or US 2006/0172090 A1.

Very preferred compounds of formula ND are those of the following sub formulae:
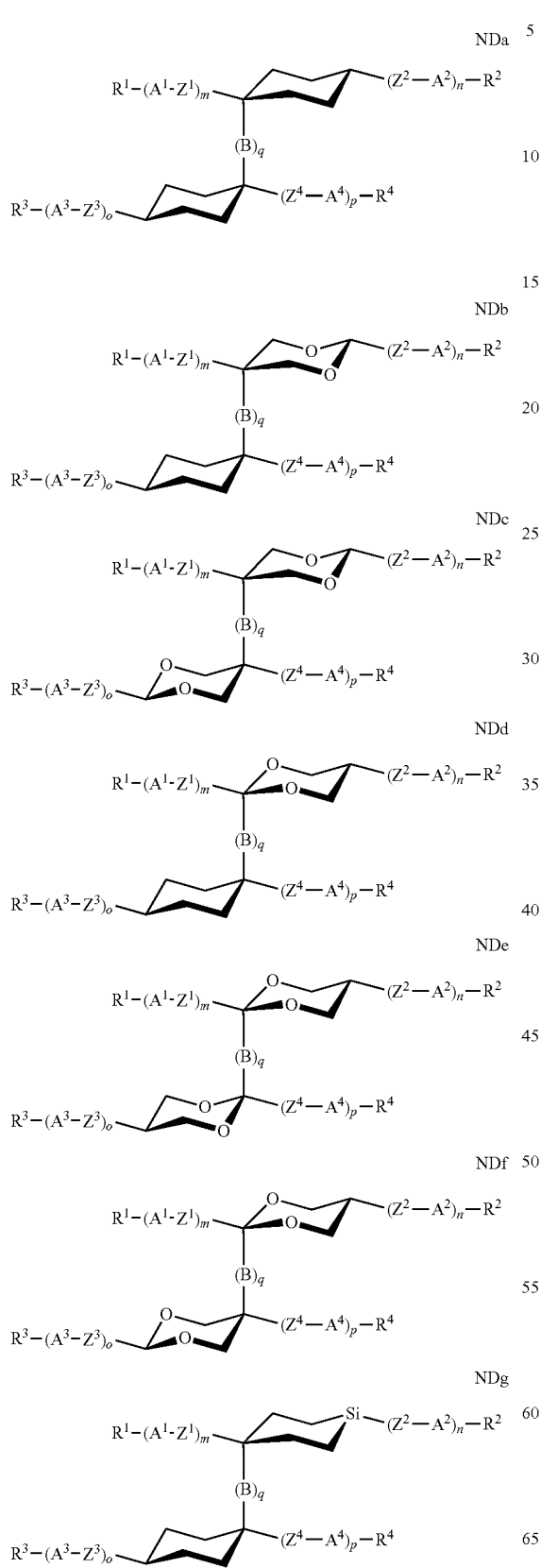
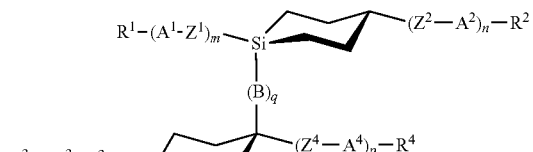
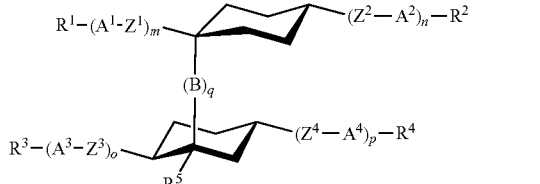
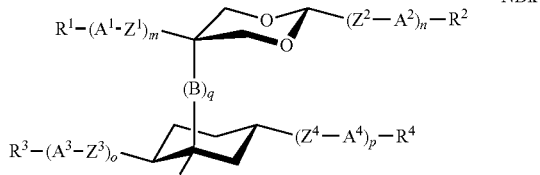
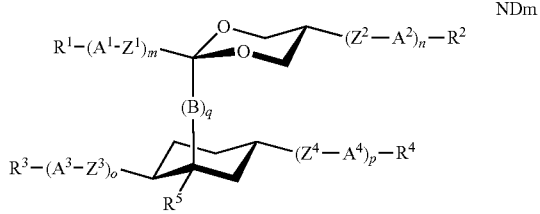
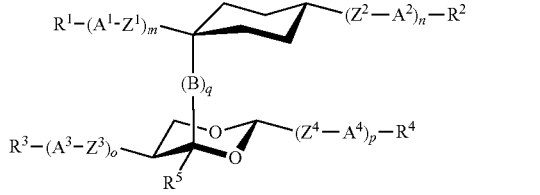
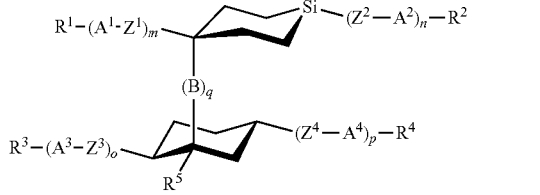
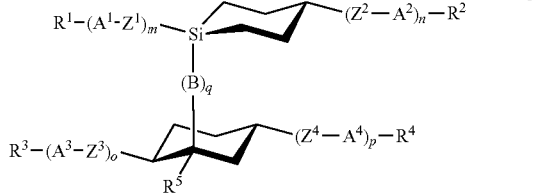

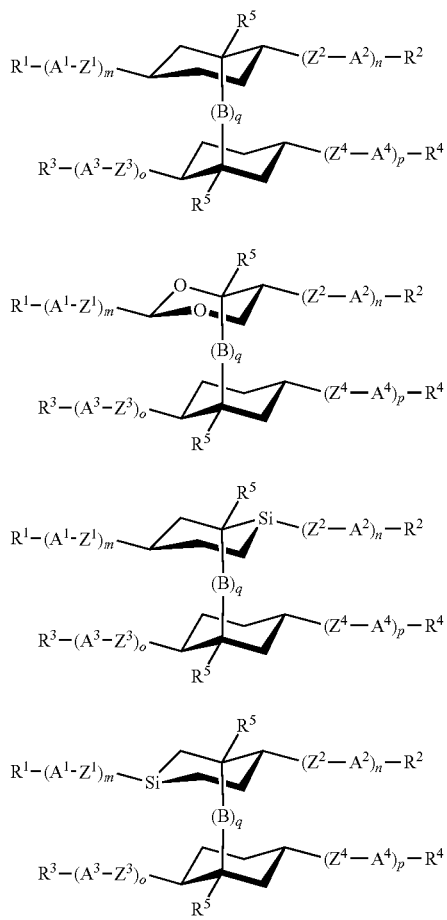
NDq
NDr
NDs
NDt
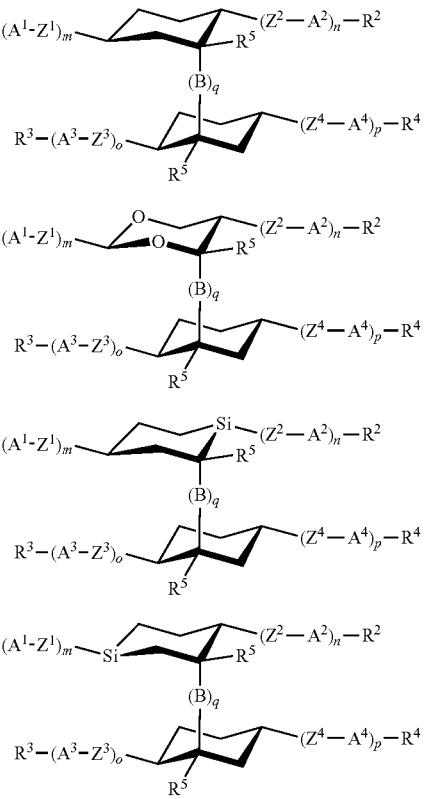
NDu
NDv
NDw
NDx
wherein $R^{1-5}$, $A^{1-4}$, $Z^{1-4}$, B, m, n, o, p and q have one the meanings given above.
Especially preferred are compounds of the following sub formulae:
ND1
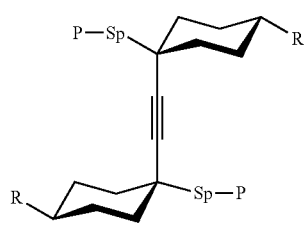
ND2
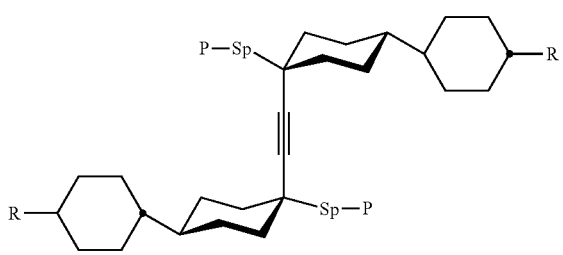
ND3
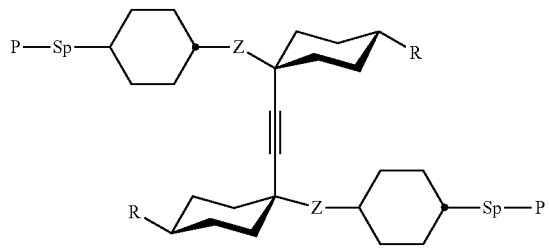
ND4
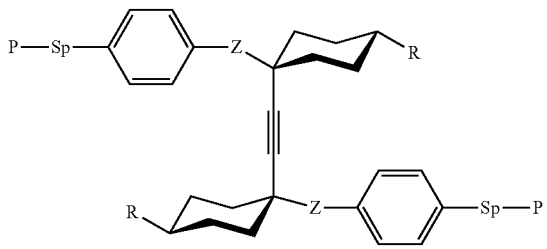

-continued
ND5
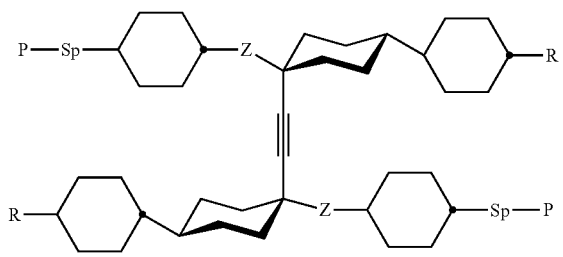
ND6
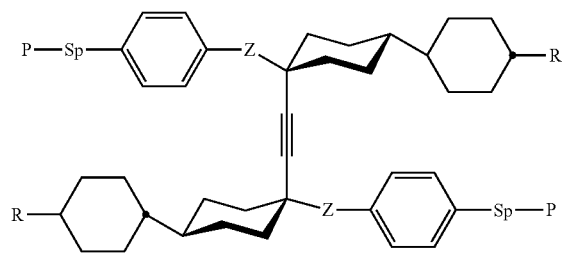
ND7
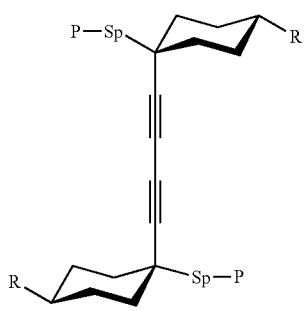
ND8
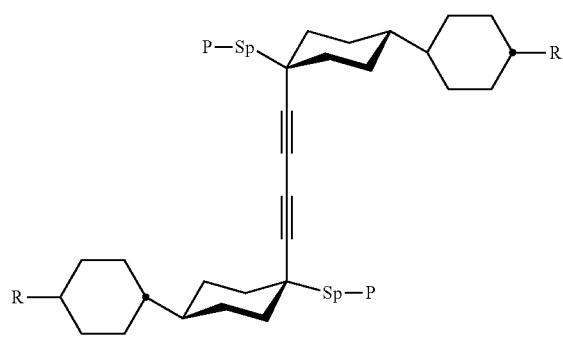
ND9
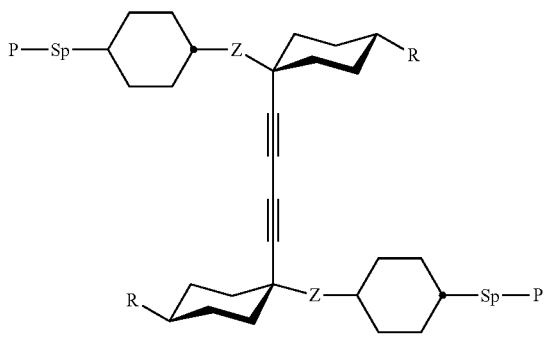
ND10
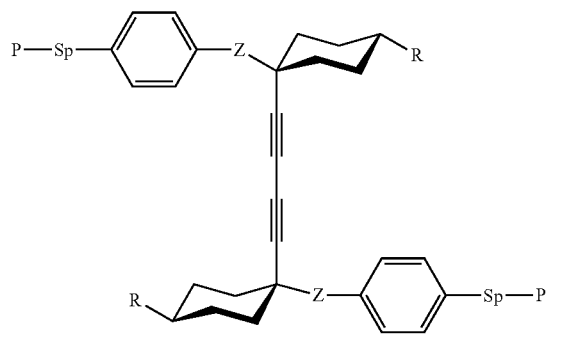
ND11
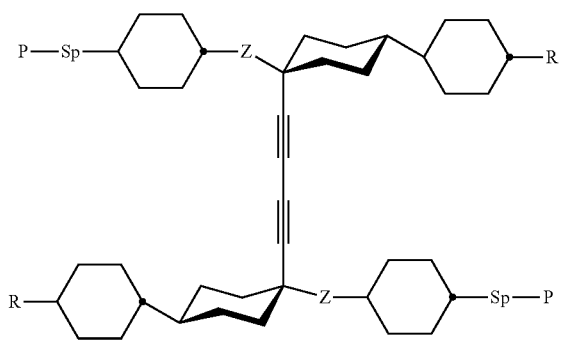
ND12
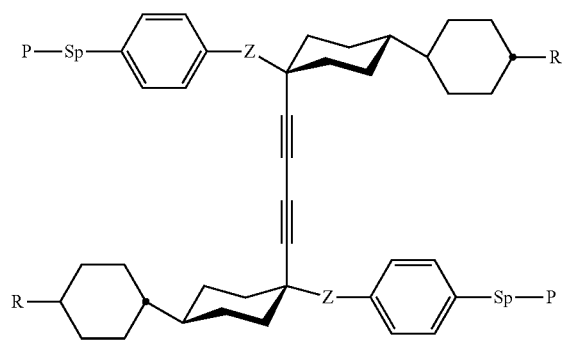

-continued
ND13
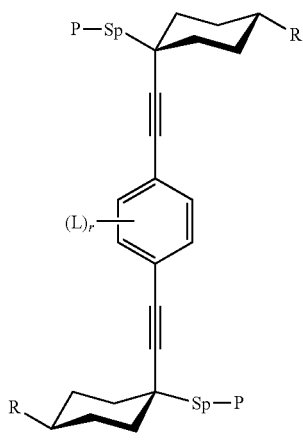
ND14
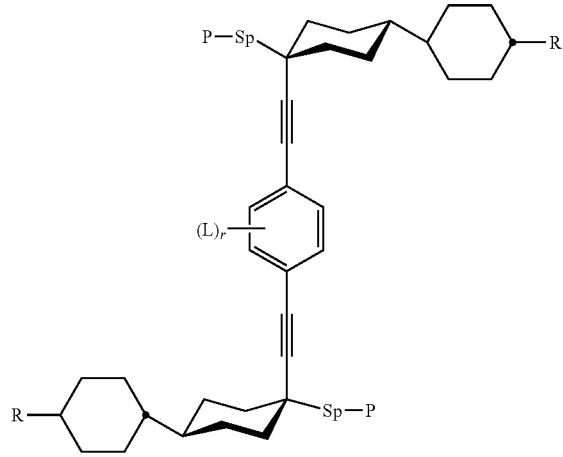
ND15
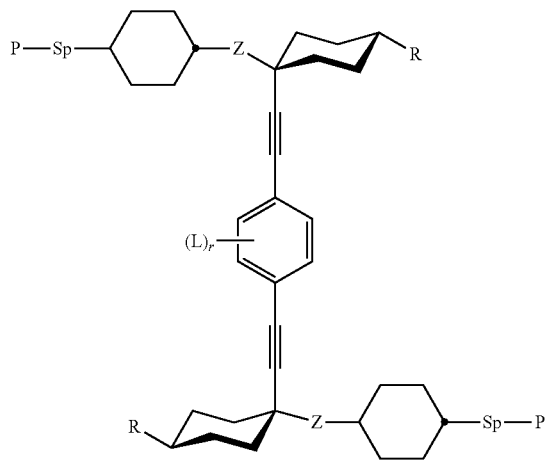
ND16
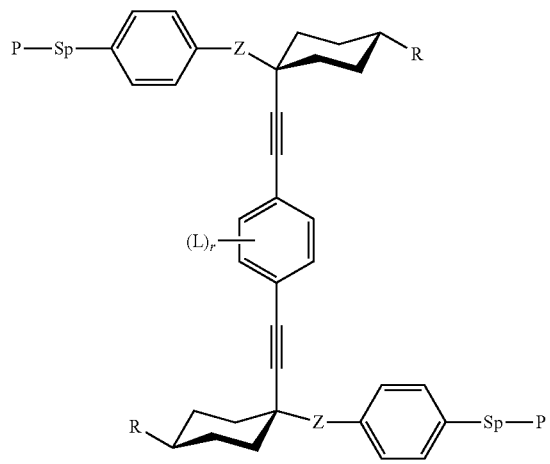
ND17
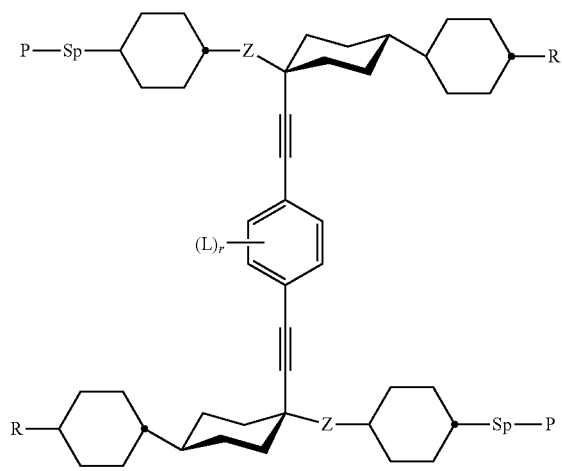
ND18
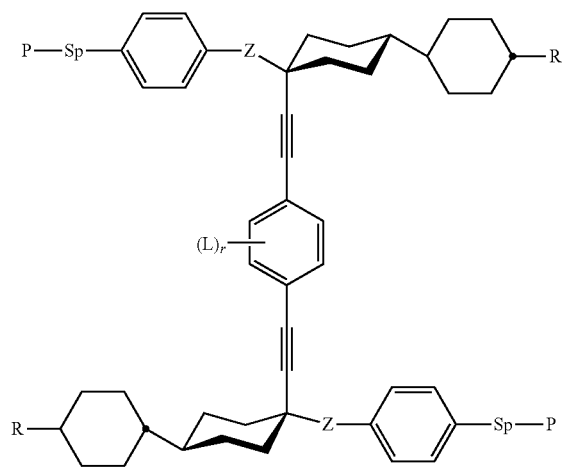

-continued
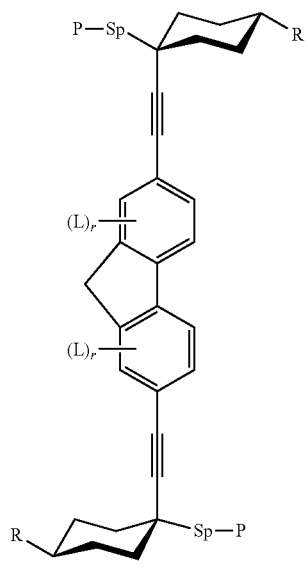
ND19
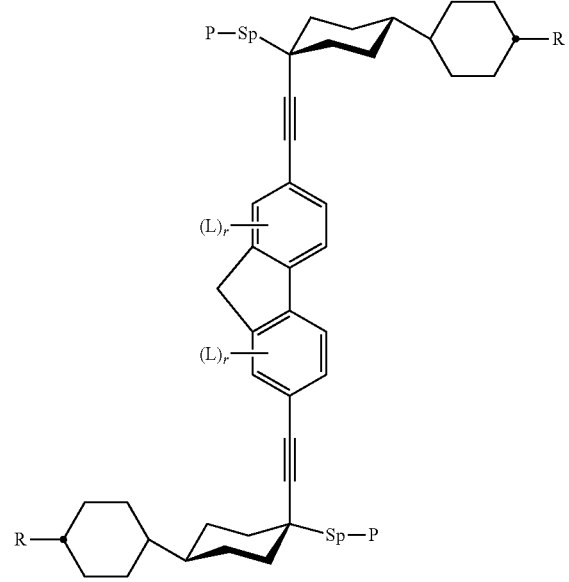
ND20
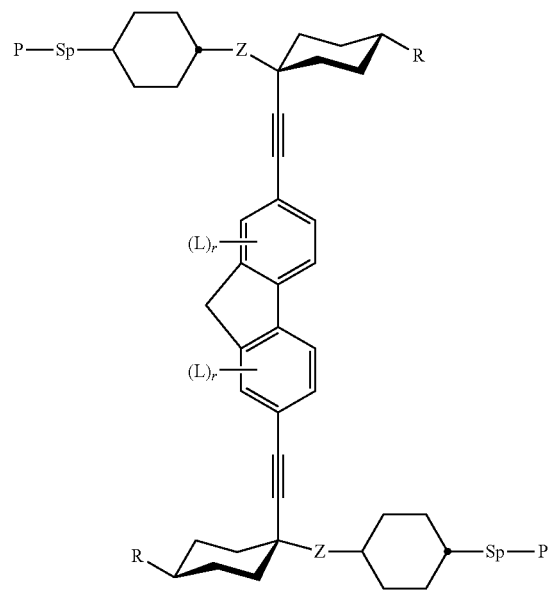
ND21
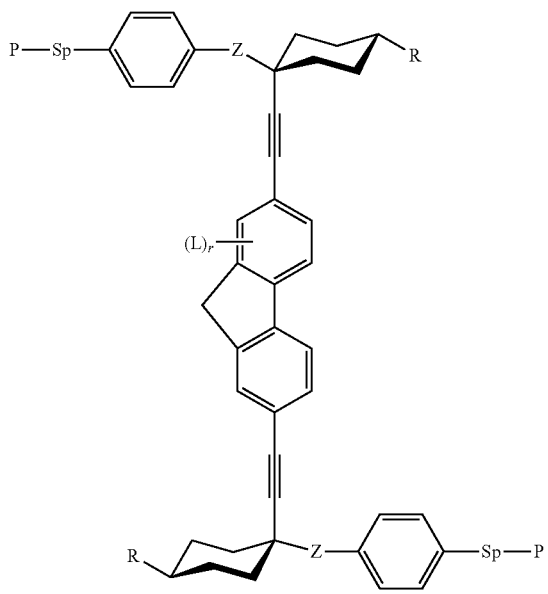
ND22

-continued
ND23
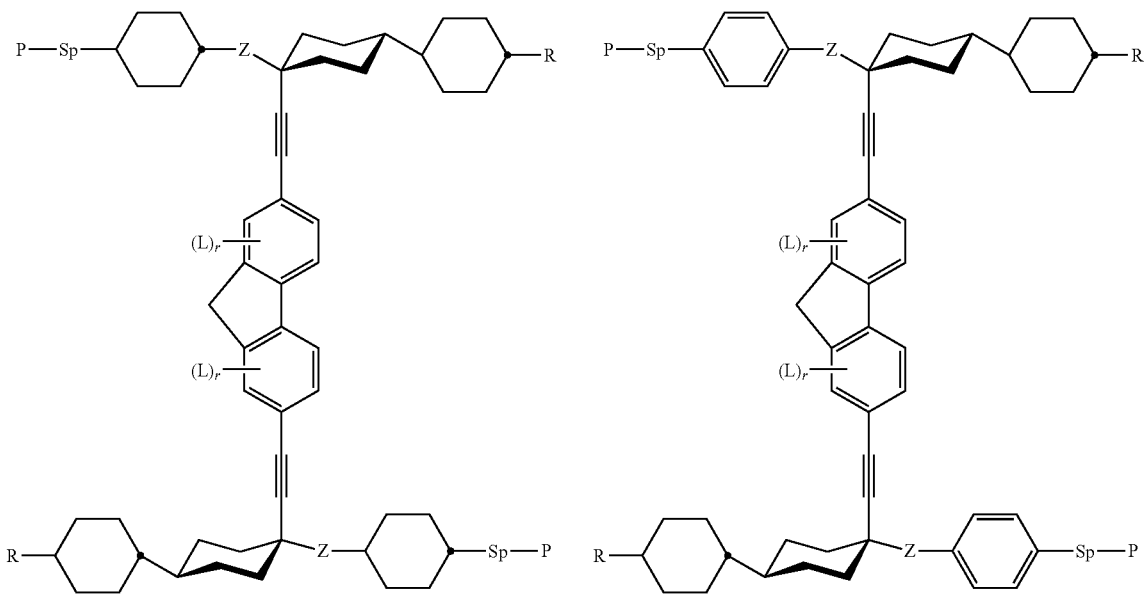
ND24
ND25
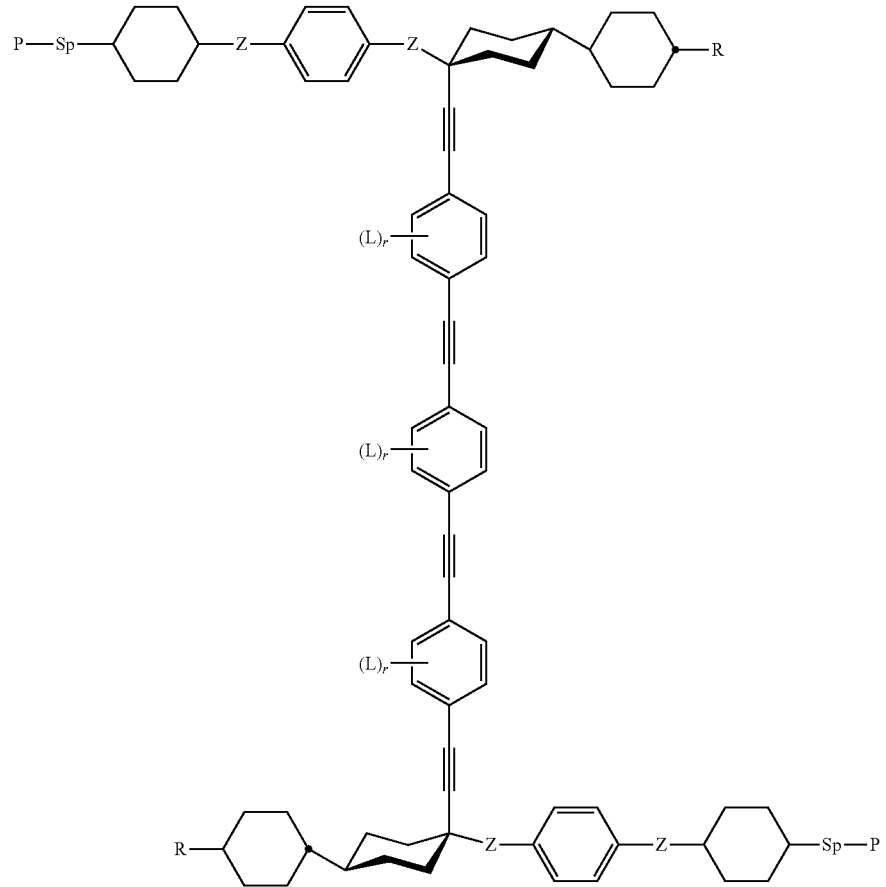

ND26

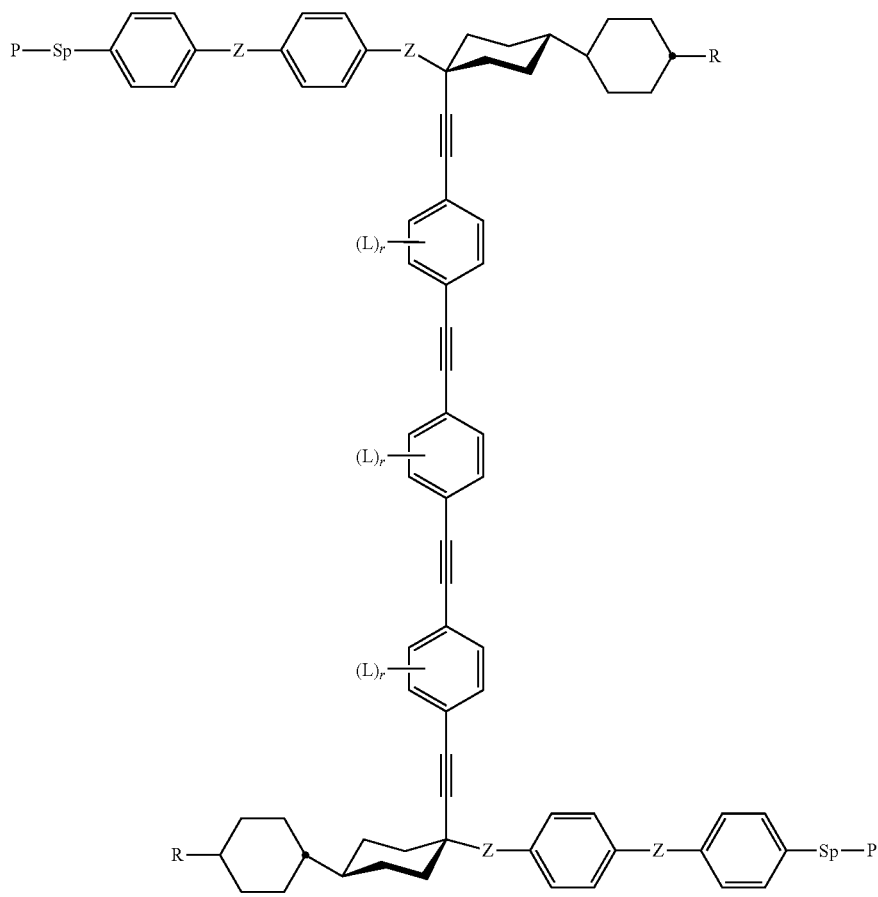

wherein Z has one of the meanings of $Z^1$ given above, R has one of the meanings of $R^1$ as given above that is different from P-Sp-, and P, Sp, L and r are as defined above, and the benzene rings in the mesogenic groups are optionally substituted by one or more groups L as defined above.

Preference is furthermore given to a polymerisable liquid crystalline medium wherein the compounds of formula ND are selected from the group of compounds of formula ND 25 or ND 26, in particular wherein Z denotes —COO—, r is in each occurrence 0, and P, Sp are as defined above.

P-Sp- in these preferred compounds is preferably P-Sp'—X', with X' preferably being —O—, —COO— or —OCOO—.

The compounds of formula ND, its subformulae and suitable methods for their synthesis are disclosed in WO 2008/119427 A1.

The amount of compounds of formula ND in the polymerisable LC material is preferably from 1 to 50%, very preferably from 1 to 40%.

Especially the combination of compound or formula I with compounds of formula ND leads to a beneficial decrease of the optical dispersion in comparison to polymerisable LC materials utilizing not that specific combination and leads to a beneficial thermal durability of the optical dispersion and/or retardation.

Another object of the invention is an RM formulation comprising one or more compounds of formula I, or comprising an RM mixture, as described above and below, and further comprising one or more solvents and/or additives.

In a preferred embodiment the RM formulation comprises optionally one or more additives selected from the group consisting of polymerisation initiators, surfactants, stabilisers, catalysts, sensitizers, inhibitors, chain-transfer agents, co-reacting monomers, reactive thinners, surface-active compounds, lubricating agents, wetting agents, dispersing agents, hydrophobing agents, adhesive agents, flow improvers, degassing or defoaming agents, deaerators, diluents, reactive diluents, auxiliaries, colourants, dyes, pigments and nanoparticles.

In another preferred embodiment the RM formulation optionally comprises one or more additives selected from polymerisable non-mesogenic compounds (reactive thinners). The amount of these additives in the RM formulation is preferably from 0 to 30%, very preferably from 0 to 25%.

The reactive thinners used are not only substances which are referred to in the actual sense as reactive thinners, but also auxiliary compounds already mentioned above which contain one or more complementary reactive units, for example hydroxyl, thiol-, or amino groups, via which a reaction with the polymerizable units of the liquid-crystalline compounds can take place.

The substances which are usually capable of photopolymerization include, for example, mono-, bi- and polyfunctional compounds containing at least one olefinic double bond. Examples thereof are vinyl esters of carboxylic acids, for example of lauric, myristic, palmitic and stearic acid, and of dicarboxylic acids, for example of succinic acid, adipic acid, allyl and vinyl ethers and methacrylic and acrylic esters of monofunctional alcohols, for example of lauryl, myristyl, palmityl and stearyl alcohol, and diallyl and divinyl ethers of bifunctional alcohols, for example ethylene glycol and 1,4-butanediol.

Also suitable are, for example, methacrylic and acrylic esters of polyfunctional alcohols, in particular those which contain no further functional groups, or at most ether groups, besides the hydroxyl groups. Examples of such alcohols are bifunctional alcohols, such as ethylene glycol, propylene glycol and their more highly condensed representatives, for example diethylene glycol, triethylene glycol, dipropylene glycol, tripropylene glycol etc., butanediol, pentanediol, hexanediol, neopentyl glycol, alkoxylated phenolic compounds, such as ethoxylated and propoxylated bisphenols, cyclohexanedimethanol, trifunctional and polyfunctional alcohols, such as glycerol, trimethylolpropane, butanetriol, trimethylolethane, pentaerythritol, ditrimethylolpropane, dipentaerythritol, sorbitol, mannitol, and the corresponding alkoxylated, in particular ethoxylated and propoxylated alcohols.

Other suitable reactive thinners are polyester (meth)acrylates, which are the (meth)acrylic ester of polyesterols.

Examples of suitable polyesterols are those which can be prepared by esterification of polycarboxylic acids, preferably dicarboxylic acids, using polyols, preferably diols. The starting materials for such hydroxyl-containing polyesters are known to the person skilled in the art. Dicarboxylic acids which can be employed are succinic, glutaric acid, adipic acid, sebacic acid, o-phthalic acid and isomers and hydrogenation products thereof, and esterifiable and transesterifiable derivatives of said acids, for example anhydrides and dialkyl esters. Suitable polyols are the abovementioned alcohols, preferably ethyleneglycol, 1,2- and 1,3-propylene glycol, 1,4-butanediol, 1,6-hexanediol, neopentyl glycol, cyclohexanedimethanol and polyglycols of the ethylene glycol and propylene glycol type.

Suitable reactive thinners are furthermore 1,4-divinylbenzene, triallyl cyanurate, acrylic esters of tricyclodecenyl alcohol of the following formula

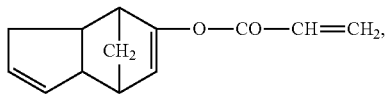 [SMILES: C=CC(=O)OC1=CC2CC1C1CC=CC21]

also known under the name dihydrodicyclopentadienyl acrylate, and the allyl esters of acrylic acid, methacrylic acid and cyanoacrylic acid.

Of the reactive thinners which are mentioned by way of example, those containing photopolymerizable groups are used in particular and in view of the abovementioned preferred compositions.

This group includes, for example, dihydric and polyhydric alcohols, for example ethylene glycol, propylene glycol and more highly condensed representatives thereof, for example diethylene glycol, triethylene glycol, dipropylene glycol, tripropylene glycol etc., butanediol, pentanediol, hexanediol, neopentyl glycol, cyclohexanedimethanol, glycerol, trimethylolpropane, butanetriol, trimethylolethane, pentaerythritol, ditrimethylolpropane, dipentaerythritol, sorbitol, mannitol and the corresponding alkoxylated, in particular ethoxylated and propoxylated alcohols.

The group furthermore also includes, for example, alkoxylated phenolic compounds, for example ethoxylated and propoxylated bisphenols.

These reactive thinners may furthermore be, for example, epoxide or urethane (meth)acrylates.

Epoxide (meth)acrylates are, for example, those as obtainable by the reaction, known to the person skilled in the art, of epoxidized olefins or poly- or diglycidyl ether, such as bisphenol A diglycidyl ether, with (meth)acrylic acid.

Urethane (meth)acrylates are, in particular, the products of a reaction, likewise known to the person skilled in the art, of hydroxylalkyl (meth)acrylates with poly- or diisocyanates.

Such epoxide and urethane (meth)acrylates are included amongst the compounds listed above as "mixed forms".

If reactive thinners are used, their amount and properties must be matched to the respective conditions in such a way that, on the one hand, a satisfactory desired effect, for example the desired colour of the composition according to the invention, is achieved, but, on the other hand, the phase behaviour of the liquid-crystalline composition is not excessively impaired. The low-crosslinking (high-crosslinking) liquid-crystalline compositions can be prepared, for example, using corresponding reactive thinners which have a relatively low (high) number of reactive units per molecule.

The group of diluents include, for example:

C1-C4-alcohols, for example methanol, ethanol, n-propanol, isopropanol, butanol, isobutanol, sec-butanol and, in particular, the C5-C12-alcohols n-pentanol, n-hexanol, n-heptanol, n-octanol, n-nonanol, n-decanol, n-undecanol and n-dodecanol, and isomers thereof, glycols, for example 1,2-ethylene glycol, 1,2- and 1,3-propylene glycol, 1,2-, 2,3- and 1,4-butylene glycol, di- and triethylene glycol and di- and tripropylene glycol, ethers, for example methyl tert-butyl ether, 1,2-ethylene glycol mono- and dimethyl ether, 1,2-ethylene glycol mono- and -diethylether, 3-methoxypropanol, 3-isopropoxypropanol, tetrahydrofuran and dioxane, ketones, for example acetone, methyl ethyl ketone, methyl isobutyl ketone and diacetone alcohol (4-hydroxy-4-methyl-2-pentanone), C1-C5-alkyl esters, for example methyl acetate, ethyl acetate, propyl acetate, butyl acetate and amyl acetate, aliphatic and aromatic hydrocarbons, for example pentane, hexane, heptane, octane, isooctane, petroleum ether, toluene, xylene, ethylbenzene, tetralin, decalin, dimethylnaphthalene, white spirit, Shellsol® and Solvesso® mineral oils, for example gasoline, kerosine, diesel oil and heating oil, but also natural oils, for example olive oil, soya oil, rapeseed oil, linseed oil and sunflower oil.

It is of course also possible to use mixtures of these diluents in the compositions according to the invention.

So long as there is at least partial miscibility, these diluents can also be mixed with water. Examples of suitable diluents here are C1-C4-alcohols, for example methanol, ethanol, n-propanol, isopropanol, butanol, isobutanol and sec-butanol, glycols, for example 1,2-ethylene glycol, 1,2- and 1,3-propylene glycol, 1,2-, 2,3- and 1,4-butylene glycol, di- and triethylene glycol, and di- and tripropylene glycol, ethers, for example tetrahydrofuran and dioxane, ketones, for example acetone, methyl ethyl ketone and diacetone alcohol (4-hydroxy-4-methyl-2-pentanone), and C1-C4-alkyl esters, for example methyl, ethyl, propyl and butyl acetate.

The diluents are optionally employed in a proportion of from about 0 to 10.0% by weight, preferably from about 0 to 5.0% by weight, based on the total weight of the RM formulation.

The antifoams and deaerators (c1)), lubricants and flow auxiliaries (c2)), thermally curing or radiation-curing auxiliaries (c3)), substrate wetting auxiliaries (c4)), wetting and dispersion auxiliaries (c5)), hydrophobicizing agents (c6)), adhesion promoters (c7)) and auxiliaries for promoting scratch resistance (c8)) cannot strictly be delimited from one another in their action.

For example, lubricants and flow auxiliaries often also act as antifoams and/or deaerators and/or as auxiliaries for improving scratch resistance.

Radiation-curing auxiliaries can also act as lubricants and flow auxiliaries and/or deaerators and/or as substrate wetting auxiliaries. In individual cases, some of these auxiliaries can also fulfil the function of an adhesion promoter (c8)).

Corresponding to the above-said, a certain additive can therefore be classified in a number of the groups c1) to c8) described below.

The antifoams in group c1) include silicon-free and silicon-containing polymers. The silicon-containing polymers are, for example, unmodified or modified polydialkylsiloxanes or branched copolymers, comb or block copolymers comprising polydialkylsiloxane and polyether units, the latter being obtainable from ethylene oxide or propylene oxide.

The deaerators in group c1) include, for example, organic polymers, for example polyethers and polyacrylates, dialkylpolysiloxanes, in particular dimethylpolysiloxanes, organically modified polysiloxanes, for example arylalkyl-modified polysiloxanes, and fluorosilicones.

The action of the antifoams is essentially based on preventing foam formation or destroying foam that has already formed. Antifoams essentially work by promoting coalescence of finely divided gas or air bubbles to give larger bubbles in the medium to be deaerated, for example the compositions according to the invention, and thus accelerate escape of the gas (of the air). Since antifoams can frequently also be employed as deaerators and vice versa, these additives have been included together under group c1).

Such auxiliaries are, for example, commercially available from Tego as TEGO® Foamex 800, TEGO® Foamex 805, TEGO® Foamex 810, TEGO® Foamex 815, TEGO® Foamex 825, TEGO® Foamex 835, TEGO® Foamex 840, TEGO® Foamex 842, TEGO® Foamex 1435, TEGO® Foamex 1488, TEGO® Foamex 1495, TEGO® Foamex 3062, TEGO® Foamex 7447, TEGO® Foamex 8020, Tego® Foamex N, TEGO® Foamex K 3, TEGO® Antifoam 2-18, TEGO® Antifoam 2-18, TEGO® Antifoam 2-57, TEGO® Antifoam 2-80, TEGO® Antifoam 2-82, TEGO® Antifoam 2-89, TEGO® Antifoam 2-92, TEGO® Antifoam 14, TEGO® Antifoam 28, TEGO® Antifoam 81, TEGO® Antifoam D 90, TEGO® Antifoam 93, TEGO® Antifoam 200, TEGO® Antifoam 201, TEGO® Antifoam 202, TEGO® Antifoam 793, TEGO® Antifoam 1488, TEGO® Antifoam 3062, TEGOPREN® 5803, TEGOPREN® 5852, TEGOPREN® 5863, TEGOPREN® 7008, TEGO® Antifoam 1-60, TEGO® Antifoam 1-62, TEGO® Antifoam 1-85, TEGO® Antifoam 2-67, TEGO® Antifoam WM 20, TEGO® Antifoam 50, TEGO® Antifoam 105, TEGO® Antifoam 730, TEGO® Antifoam MR 1015, TEGO® Antifoam MR 1016, TEGO® Antifoam 1435, TEGO® Antifoam N, TEGO® Antifoam KS 6, TEGO® Antifoam KS 10, TEGO® Antifoam KS 53, TEGO® Antifoam KS 95, TEGO® Antifoam KS 100, TEGO® Antifoam KE 600, TEGO® Antifoam KS 911, TEGO® Antifoam MR 1000, TEGO® Antifoam KS 1100, Tego® Airex 900, Tego® Airex 910, Tego® Airex 931, Tego® Airex 935, Tego® Airex 936, Tego® Airex 960, Tego® Airex 970, Tego® Airex 980 and Tego® Airex 985 and from BYK as BYK®-011, BYK®-019, BYK®-020, BYK®-021, BYK®-022, BYK®-023, BYK®-024, BYK®-025, BYK®-027, BYK®-031, BYK®-032, BYK®-033, BYK®-034, BYK®-035, BYK®-036, BYK®-037, BYK®-045, BYK®-051, BYK®-052, BYK®-053, BYK®-055, BYK®-057, BYK®-065, BYK®-066, BYK®-070, BYK®-080, BYK®-088, BYK®-141 and BYK®-A 530.

The auxiliaries in group c1) are optionally employed in a proportion of from about 0 to 3.0% by weight, preferably from about 0 to 2.0% by weight, based on the total weight of the RM formulation.

In group c2), the lubricants and flow auxiliaries typically include silicon-free, but also silicon-containing polymers, for example polyacrylates or modifiers, low-molecular-weight polydialkylsiloxanes. The modification consists in some of the alkyl groups having been replaced by a wide variety of organic radicals. These organic radicals are, for example, polyethers, polyesters or even long-chain alkyl radicals, the former being used the most frequently.

The polyether radicals in the correspondingly modified polysiloxanes are usually built up from ethylene oxide and/or propylene oxide units. Generally, the higher the proportion of these alkylene oxide units in the modified polysiloxane, the more hydrophilic is the resultant product.

Such auxiliaries are, for example, commercially available from Tego as TEGO® Glide 100, TEGO® Glide ZG 400, TEGO® Glide 406, TEGO® Glide 410, TEGO® Glide 411, TEGO® Glide 415, TEGO® Glide 420, TEGO® Glide 435, TEGO® Glide 440, TEGO® Glide 450, TEGO® Glide A 115, TEGO® Glide B 1484 (can also be used as antifoam and deaerator), TEGO® Flow ATF, TEGO® Flow 300, TEGO® Flow 460, TEGO® Flow 425 and TEGO® Flow ZFS 460. Suitable radiation-curable lubricants and flow auxiliaries, which can also be used to improve the scratch resistance, are the products TEGO® Rad 2100, TEGO® Rad 2200, TEGO® Rad 2500, TEGO® Rad 2600 and TEGO® Rad 2700, which are likewise obtainable from TEGO.

Such-auxiliaries are available, for example, from BYK as BYK®-300 BYK®-306, BYK®-307, BYK®-310, BYK®-320, BYK®-333, BYK®-341, Byk® 354, Byk®361, Byk®361N, BYK®388.

The auxiliaries in group c2) are optionally employed in a proportion of from about 0 to 3.0% by weight, preferably from about 0 to 2.0% by weight, based on the total weight of the RM formulation.

In group c3), the radiation-curing auxiliaries include, in particular, polysiloxanes having terminal double bonds which are, for example, a constituent of an acrylate group. Such auxiliaries can be crosslinked by actinic or, for example, electron radiation. These auxiliaries generally combine a number of properties together. In the uncrosslinked state, they can act as antifoams, deaerators, lubricants and flow auxiliaries and/or substrate wetting auxiliaries, while, in the crosslinked state, they increase, in particular, the scratch resistance, for example of coatings or films which can be produced using the compositions according to the invention. The improvement in the gloss properties, for example of precisely those coatings or films, is regarded essentially as a consequence of the action of these auxiliaries as antifoams, deaerators and/or lubricants and flow auxiliaries (in the uncrosslinked state).

Examples of suitable radiation-curing auxiliaries are the products TEGO® Rad 2100, TEGO® Rad 2200, TEGO® Rad 2500, TEGO® Rad 2600 and TEGO® Rad 2700 available from TEGO and the product BYK®-371 available from BYK.

Thermally curing auxiliaries in group c3) contain, for example, primary OH groups which are able to react with isocyanate groups, for example of the binder.

Examples of thermally curing auxiliaries which can be used are the products BYK®-370, BYK®-373 and BYK®-375 available from BYK.

The auxiliaries in group c3) are optionally employed in a proportion of from about 0 to 5.0% by weight, preferably from about 0 to 3.0% by weight, based on the total weight of the RM formulation.

The substrate wetting auxiliaries in group c4) serve, in particular, to increase the wettability of the substrate to be printed or coated, for example, by printing inks or coating compositions, for example compositions according to the invention. The generally attendant improvement in the lubricant and flow behaviour of such printing inks or coating compositions has an effect on the appearance of the finished (for example crosslinked) print or coating.

A wide variety of such auxiliaries are commercially available, for example from Tego as TEGO® Wet KL 245, TEGO® Wet 250, TEGO® Wet 260 and TEGO® Wet ZFS 453 and from BYK as BYK®-306, BYK®-307, BYK®-310, BYK®-333, BYK®-344, BYK®-345, BYK®-346 and Byk®-348.

The auxiliaries in group c4) are optionally employed in a proportion of from about 0 to 3.0% by weight, preferably from about 0 to 1.5% by weight, based on the total weight of the liquid-crystalline composition.

The wetting and dispersion auxiliaries in group c5) serve, in particular, to prevent the flooding and floating and the sedimentation of pigments and are therefore, if necessary, suitable in particular in pigmented compositions according to the invention.

These auxiliaries stabilize pigment dispersions essentially through electrostatic repulsion and/or steric hindrance of the pigment particles containing these additives, where, in the latter case, the interaction of the auxiliary with the ambient medium (for example binder) plays a major role.

Since the use of such wetting and dispersion auxiliaries is common practice, for example in the technical area of printing inks and paints, the selection of a suitable auxiliary of this type generally does not present the person skilled in the art with any difficulties, if they are used.

Such wetting and dispersion auxiliaries are commercially available, for example from Tego, as TEGO® Dispers 610, TEGO® Dispers 610 S, TEGO® Dispers 630, TEGO® Dispers 700, TEGO® Dispers 705, TEGO® Dispers 710, TEGO® Dispers 720 W, TEGO® Dispers 725 W, TEGO® Dispers 730 W, TEGO® Dispers 735 W and TEGO® Dispers 740 W and from BYK as Disperbyk®, Disperbyk®-107, Disperbyk®-108, Disperbyk®-110, Disperbyk®-111, Disperbyk®-115, Disperbyk®-130, Disperbyk®-160, Disperbyk®-161, Disperbyk®-162, Disperbyk®-163, Disperbyk®-164, Disperbyk®-165, Disperbyk®-166, Disperbyk®-167, Disperbyk®-170, Disperbyk®-174, Disperbyk®-180, Disperbyk®-181, Disperbyk®-182, Disperbyk®-183, Disperbyk®-184, Disperbyk®-185, Disperbyk®-190, Anti-Terra®-U, Anti-Terra®-U 80, Anti-Terra®-P, Anti-Terra®-203, Anti-Terra®-204, Anti-Terra®-206, BYK®-151, BYK®-154, BYK®-155, BYK®-P 104 S, BYK®-P 105, Lactimon®, Lactimon®-WS and Bykumen®.

The amount of the auxiliaries in group c5) used on the mean molecular weight of the auxiliary. In any case, a preliminary experiment is therefore advisable, but this can be accomplished simply by the person skilled in the art.

The hydrophobicizing agents in group c6) can be used to give water-repellent properties to prints or coatings produced, for example, using compositions according to the invention. This prevents or at least greatly suppresses swelling due to water absorption and thus a change in, for example, the optical properties of such prints or coatings. In addition, when the composition is used, for example, as a printing ink in offset printing, water absorption can thereby be prevented or at least greatly reduced.

Such hydrophobicizing agents are commercially available, for example, from Tego as Tego® Phobe WF, Tego® Phobe 1000, Tego® Phobe 1000 S, Tego® Phobe 1010, Tego® Phobe 1030, Tego® Phobe 1010, Tego® Phobe 1010, Tego® Phobe 1030, Tego® Phobe 1040, Tego® Phobe 1050, Tego® Phobe 1200, Tego® Phobe 1300, Tego® Phobe 1310 and Tego® Phobe 1400.

The auxiliaries in group c6) are optionally employed in a proportion of from about 0 to 5.0% by weight, preferably from about 0 to 3.0% by weight, based on the total weight of the RM formulation.

Adhesion promoters from group c7) serve to improve the adhesion of two interfaces in contact. It is directly evident from this that essentially the only fraction of the adhesion promoter that is effective is that located at one or the other or at both interfaces. If, for example, it is desired to apply liquid or pasty printing inks, coating compositions or paints to a solid substrate, this generally means that the adhesion promoter must be added directly to the latter or the substrate must be pre-treated with the adhesion promoters (also known as priming), i.e. this substrate is given modified chemical and/or physical surface properties.

If the substrate has previously been primed with a primer, this means that the interfaces in contact are that of the primer on the one hand and of the printing ink or coating composition or paint on the other hand. In this case, not only the adhesion properties between the substrate and the primer, but also between the substrate and the printing ink or coating composition or paint play a part in adhesion of the overall multilayer structure on the substrate.

Adhesion promoters in the broader sense which may be mentioned are also the substrate wetting auxiliaries already listed under group c4), but these generally do not have the same adhesion promotion capacity.

In view of the widely varying physical and chemical natures of substrates and of printing inks, coating compositions and paints intended, for example, for their printing or coating, the multiplicity of adhesion promoter systems is not surprising.

Adhesion promoters based on silanes are, for example, 3-aminopropyltrimethoxysilane, 3-aminopropyltriethoxysilane, 3-aminopropylmethyldiethoxysilane, N-aminoethyl-3-aminopropyltrimethoxysilane, N-aminoethyl-3-aminopropylmethyldimethoxysilane, N-methyl-3-aminopropyltrimethoxysilane, 3-ureidopropyltriethoxysilane, 3-methacryloyloxypropyltrimethoxysilane, 3-glycidyloxypropyltrimethoxysilane, 3-mercaptopropyltrimethoxysilane, 3-chloropropyltrimethoxysilane and vinyltrimethoxysilane. These and other silanes are commercially available from Hüls, for example under the tradename DYNASILAN®.

Corresponding technical information from the manufacturers of such additives should generally be used or the person skilled in the art can obtain this information in a simple manner through corresponding preliminary experiments.

However, if these additives are to be added as auxiliaries from group c7) to the RM formulations according to the invention, their proportion optionally corresponds to from about 0 to 5.0% by weight, based on the total weight of the RM formulation. These concentration data serve merely as guidance, since the amount and identity of the additive are determined in each individual case by the nature of the substrate and of the printing/coating composition. Corresponding technical information is usually available from the manufacturers of such additives for this case or can be determined in a simple manner by the person skilled in the art through corresponding preliminary experiments.

The auxiliaries for improving the scratch resistance in group c8) include, for example, the abovementioned products TEGO® Rad 2100, TEGO® Rad 2200, TEGO® Rad 2500, TEGO® Rad 2600 and TEGO® Rad 2700, which are available from Tego.

For these auxiliaries, the amount data given for group c3) are likewise suitable, i.e. these additives are optionally employed in a proportion of from about 0 to 5.0% by weight, preferably from about 0 to 3.0% by weight, based on the total weight of the liquid-crystalline composition.

Examples which may be mentioned of light, heat and/or oxidation stabilizers are the following:

alkylated monophenols, such as 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-ditert-butyl-4-methoxymethylphenol, nonylphenols which have a linear or branched side chain, for example 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures of these compounds, alkylthiomethylphenols, such as 2,4-dioctylthiomethyl-6-tert-butylphenol, 2,4-dioctylthiomethyl-6-methylphenol, 2,4-dioctylthiomethyl-6-ethylphenol and 2,6-didodecylthiomethyl-4-nonylphenol, Hydroquinones and alkylated hydroquinones, such as 2,6-di-tert-butyl-4-methoxyphenol, 2,5-di-tert-butylhydroquinone, 2,5-di-tert-amylhydrocrainone, 2,6-diphenyl-4-octadecyloxyphenol, 2,6-di-tert-butylhydroquinone, 2,5-ditert-butyl-4-hydroxyanisole, 3,5-di-tert-butyl-4-hydroxyanisole, 3,5-di-tert-butyl-4-hydroxyphenyl stearate and bis(3,5-di-tert-butyl-4-hydroxyphenyl)adipate, Tocopherols, such as α-tocopherol, β-tocopherol, γ-tocopherol, δ-tocopherol and mixtures of these compounds, and tocopherol derivatives, such as tocopheryl acetate, succinate, nicotinate and polyoxyethylenesuccinate ("tocofersolate"), hydroxylated diphenyl thioethers, such as 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol) and 4,4'-bis(2,6-dimethyl-4-hydroxyphenyl)disulfide, Alkylidenebisphenols, such as 2,2'-methylenebis(6-tertbutyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-ditert-butylphenol), 4,4'-methenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecyl-mercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tertbutyl-4-hydroxyphenyl)propane, 2,2-bis(5-tert-butyl-4-hydroxy-2-methylphenyl)-4-n-dodecyl-mercaptobutane and 1,1,5,5-tetrakis(5-tert-butyl-4-hydroxy-2-methylphenyl) pentane, O—, N- and S-benzyl compounds, such as 3,5,3',5'-tetratert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-ditert-butyl-4-hydroxybenzyl)amine, bis(4-tert-butyl-3-hydroxy-2,6-dimethylbenzyl)dithioterephthalate, bis(3,5-ditert-butyl-4-hydroxybenzyl)sulfide and isooctyl-3,5-di-tertbutyl-4-hydroxybenzylmercaptoacetate, aromatic hydroxybenzyl compounds, such as 1,3,5-tris(3, 5-di-tert-butyl-4-hydroxybenzyl)-2,4,6-trimethyl-benzene, 1,4-bis(3,5-di-tert-butyl-4-hydroxybenzyl)-2,3,5,6-tetramethyl-benzene and 2,4,6-tris(3,5-di-tert-butyl-4-hydroxybenzyl)phenol, Triazine compounds, such as 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tertbutyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris-(3,5-di-tert-butyl-4-hydroxyphenylpropionyl) hexahydro-1,3,5-triazine, 1,3,5-tris(3,5-dicyclohexyl-4-hydroxybenzyl)isocyanurate and 1,3,5-tris(2-hydroxyethyl) isocyanurate, Benzylphosphonates, such as dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate and dioctadecyl 5-tert-butyl-4-hydroxy-3-methylbenzylphosphonate, Acylaminophenols, such as 4-hydroxylauroylanilide, 4-hydroxystearoylanilide and octyl N-(3,5-di-tert-butyl-4-hydroxyphenyl)carbamate, Propionic and acetic esters, for example of monohydric or polyhydric alcohols, such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxalamide, 3-thiaundecanol, 3-thiapentadecanol, trimethylhexanediol, trimethyloIpropane and 4-hydroxymethyl-1-phospha-2,6,7-trioxabicyclo [2.2.2]-octane, Propionamides based on amine derivatives, such as N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine and N,N'-bis(3,5-di-tertbutyl-4-hydroxyphenylpropionyl)hydrazine, Ascorbic acid (Vitamin C) and ascorbic acid derivatives, such as ascorbyl palmitate, laurate and stearate, and ascorbyl sulfate and phosphate, Antioxidants based on amine compounds, such as N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octyl-substituted diphenylamine, such as p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis[4-methoxyphenyl]amine, 2,6-di-tert-butyl-4-dimethylaminomethylphenol, 2,4-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octyl-substituted N-phenyl-1-naphthylamine, a mixture of mono- and dialkylated tert-butyl/tert-octyldiphenylamine, a mixture of mono- and dialkylated nonyldiphenylamine, a mixture of mono- and dialkylated dodecyldiphenylamine, a mixture of mono- and dialkylated isopropyl/isohexyldiphenylamine, a mixture of mono- and dialkylated tert-butyldiphenylamine, 2,3-dihydro-3,3-dimethyl-4H-1,4-benzothiazine, phenothiazine, a mixture of mono- and dialkylated tert-butyl/tert-octylphenothiazine, a mixture of mono- and dialkylated tert-octylphenothiazine, N-allylphenothiazine, N,N,N',N'-tetraphenyl-1,4-diaminobut-2-ene, N,N-bis(2,2,6,6-tetramethylpiperidin-4-yl)hexamethylenediamine, bis(2,2,6,6-tetramethylpiperidin-4-yl)sebacate, 2,2,6,6-tetramethylpiperidin-4-one and 2,2,6,6-tetramethylpiperidin-4-ol, Phosphines, Phosphites and phosphonites, such as triphenylphosnine triphenylphosphite, diphenyl alkyl phosphite, phenyl dialkyl phosphite, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)pentaerythritol diphosphite, diisodecyloxy pentaerythritol diphosphite, bis(2,4-di-tert-butyl-6-methylphenyl)pentaerythritol diphosphite, bis(2,4,6-tris(tert-butylphenyl))pentaerythritol diphosphite, tristearyl sorbitol triphosphite, tetrakis(2,4-di-tert-butylphenyl)$_{4,4'}$-biphenylenediphosphonite, 6-isooctyloxy-2,4,8,10-tetra-tert-butyl-12H-dibenz[d,g]-1,3,2-dioxaphosphocine, 6-fluoro-2,4,8,10-tetra-tert-butyl-12-methyl-dibenz[d,g]-1,3,2-dioxaphosphocine, bis(2,4-di-tert-butyl-6-methylphenyl)methyl phosphite and bis(2,4-di-tert-butyl-6-methylphenyl)ethyl phosphite, 2-(2'-Hydroxyphenyl)benzotriazoles, such as 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3,5'-bis-(α,α-dimethylbenzyl)-2'-hydroxyphenyl)benzotriazole, a mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxy phenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxy phenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenyl benzotriazole, 2,2'-methylenebis[4-(1,1,3,3-tetramethylbutyl)-6-benzotriazol-2-ylphenol]; the product of complete esterification of 2-[3'-tert-butyl-5'-(2-methoxycarbonylethyl)-2'-hydroxyphenyl]-2H-benzotriazole with polyethylene glycol 300;

sulfur-containing peroxide scavengers and sulfur-containing antioxidants, such as esters of 3,3'-thiodipropionic acid, for example the lauryl, stearyl, myristyl and tridecyl esters, mercaptobenzimidazole and the zinc salt of 2-mercaptobenzimidazole, dibutylzinc dithiocarbamates, dioctadecyl disulfide and pentaerythritol tetrakis(β-dodecylmercapto)propionate, 2-hydroxybenzophenones, such as the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives, Esters of unsubstituted and substituted benzoic acids, such as 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl-3,5-di-tert-butyl-4-hydroxybenzoate, octadecyl-3,5-di-tert-butyl-4-hydroxybenzoate and 2-methyl-4,6-di-tert-butylphenyl-3,5-di-tert-butyl-4-hydroxybenzoate, Acrylates, such as ethyl α-cyano-β,β-diphenylacrylate, isooctyl α-cyano-β,β-diphenylacrylate, methyl α-methoxycarbonylcinnamate, methyl α-cyano-β-methyl-p-methoxycinnamate, butyl-α-cyano-β-methyl-p-methoxycinnamate and methyl-α-methoxycarbonyl-p-methoxycinnamate, sterically hindered amines, such as bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, bis(1-octyloxy-2,2,6,6-tetramethylpiperidin-4-yl)sebacate, bis(1,2,2,6,6-pentamethylpiperidin-4-yl)-n-butyl-3,5-di-tert-butyl-4-hydroxybenzylmalonate, the condensation product of 1-(2-hydroxyethyl)-2,2,6,6-tetramethyl-4-hydroxypiperidine and succinic acid, the condensation product of N,N'-bis(2,2,6,6-tetramethylpiperidin-4-yl)hexamethylenediamine and 4-tert-octylamino-2,6-dichloro-1,3,5-triazine, tris(2,2,6,6-tetramethylpiperidin-4-yl)nitrilotriacetate, tetrakis(2,2,6,6-tetramethylpiperidin-4-yl)1,2,3,4-butanetetracarboxylate, 1,1'-(1,2-ethylene)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidin-4-yl)$_2$-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidin-4-yl)sebacate, bis(1-octyloxy-2,2,6,6-tetramethylpiperidin-4-yl)succinate, the condensation product of N,N'-bis(2,2,6,6-tetramethylpiperidin-4-yl)hexamethylenediamine and 4-morpholino-2,6-dichloro-1,3,5-triazine, the condensation product of 2-chloro-4,6-bis(4-n-butylamino-2,2,6,6-tetramethylpiperidin-4-yl)-1,3,5-triazine and 1,2-bis(3-aminopropylamino)ethane, the condensation product of 2-chloro-4,6-di(4-n-butylamino-1,2,2,6,6-pentamethylpiperidin-4-yl)-1,3,5-triazine and 1,2-bis(3-aminopropylamino)ethane, 8-acetyl-3-dodecyl-7,7,9,9-tetramethyl-1,3,8-triazaspiro[4.5]-decane-2,4-dione, 3-dodecyl-1-(2,2,6,6-tetramethylpiperidin-4-yl)pyrrolidine-2,5-dione, 3-dodecyl-1-(1,2,2,6,6-pentamethylpiperidin-4- yl)pyrrolidine-2,5-dione, a mixture of 4-hexadecyloxy- and 4-stearyloxy-2,2,6,6-tetramethylpiperidine, the condensation product of N,N'-bis(2,2,6,6-tetramethylpiperidin-4-yl)hexamethylenediamine and 4-cyclohexylamino-2,6-dichloro-1,3,5-triazine, the condensation product of 1,2-bis(3-aminopropylamino)ethane and 2,4,6-trichloro-1,3,5-triazine, 4-butylamino-2,2,6,6-tetramethylpiperidine, N-(2,2,6,6-tetramethylpiperidin-4-yl)-n-dodecylsuccinimide, N-(1,2,2,6,6-pentamethylpiperidin-4-yl)-n-dodecylsuccinimide, 2-undecyl-7,7,9,9-tetramethyl-1-oxa-3,8-diaza-4-oxospiro[4.5]-decane, the condensation product of 7,7,9,9-tetramethyl-2-cycloundecyl-1-oxa-3,8-diaza-4-oxospiro-[4.5]decane and epichlorohydrin, the condensation products of 4-amino-2,2,6,6-tetramethylpiperidine with tetramethylolacetylenediureas and poly(methoxypropyl-3-oxy)-[4(2,2,6,6-tetramethyl)piperidinyl]-siloxane, Oxalamides, such as 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxalamide, 2-ethoxy-5-tert-butyl-2'-ethoxanilide and its mixture with 2-ethoxy-2'-ethyl-5,4'-di-tert-butoxanilide, and mixtures of ortho-, para-methoxy-disubstituted oxanilides and mixtures of ortho- and para-ethoxy-disubstituted oxanilides, and 2-(2-hydroxyphenyl)-1,3,5-triazines, such as 2,4,6-tris-(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropoxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis-(2,4-dimethylphenyl)-1,3,5-triazine, 2-(2-hydroxy-4-hexyloxyphenyl)-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine and 2-(2-hydroxyphenyl)-4-(4-methoxyphenyl)-6-phenyl-1,3,5-triazine.

Further examples which preferably used as mentioned of light, heat and/or oxidation stabilizers are the following:

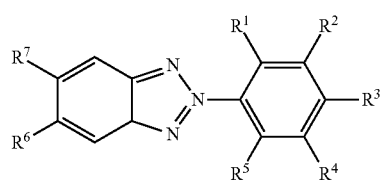

wherein the individual radicals have the following meanings:
$R^1$ to $R^5$ denote each independently selected from the group consisting of H, -alkyl, —OH, -alkylaryl, -alkylheteroaryl, -cycloalkyl, cycloheteroalkyl, alkenyl, aryl and —SO$_3$H, and
$R^6$ and $R^7$ denote each and independently a hydrogen atom, a hydroxy group, or a halogen atom, or $R^5$ and $R^7$ form an optionally substituted cycloalkyl or cycloheteroalkyl ring.

and/or

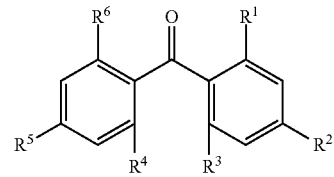

wherein the individual radicals, independently of each other and on each occurrence identically or differently, have the following meanings:
$R^1$, $R^2$, $R^5$ and $R^6$ each and independently from another denote, H, halogen, —OH, —SH, —NR$^{xx}$R$^{yy}$—, —CO—R$^{xx}$—, —COOR$^{xx}$, —OCOR$^{xx}$, —OCO—OR$^{xx}$, —S—COR$^{xx}$, —CO—SR$^{xx}$, —NR$^{xx}$—CO—OR$^{yy}$, —O—CO—NR$^{xx}$R$^{yy}$, —NR$^{xx}$—CO—NR$^{xx}$R$^{yy}$, whereby one of $R^1$ or $R^6$ in formula UVI denotes —OH,
$R^3$ and $R^4$ each represent a hydrogen atom, a hydroxy group, or a halogen atom,
$R^{xx}$ and $R^{yy}$ each, independently of one another, denotes H, alkyl having 1 to 12 C atoms, in which, in addition, one or more non-adjacent CH$_2$ groups may each be replaced, independently of one another, by —O—, —S—, —NH—, —NR$^{xx}$—, —SiR$^{xx}$R$^{yy}$—, —CO—, —COO—, —OCO—, —OCO—O—, —S—CO—, —CO—S—, —NR$^{xx}$—CO—O—, —O—CO—NR$^{xx}$—, —NR$^{xx}$—CO—NR$^{yy}$—, —CH═CH— or —C≡C— in such a way that O and/or S atoms are not linked directly to one another,
and/or

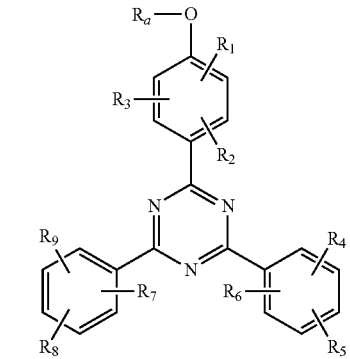

wherein the individual radicals, independently of each other and on each occurrence identically or differently, have the following meanings:
$R^1$ to $R^9$ each represent a hydrogen atom, a hydroxy group, a halogen atom, an alkyl group having 1 to 20 carbon atoms, an alkenyl group having 3 to 20 carbon atoms, an alkoxy group having 1 to 20 carbon atoms, or an aryl group having 6 to 20 carbon atoms,
$R^a$ denotes a straight chain or branched alkyl having 1 to 20, preferably 1 to 12 C atoms, which is optionally mono- or polysubstituted by F, Cl, Br, I or CN and in which, in addition, one or more non-adjacent CH$_2$ groups may each be replaced, independently of one another, by —O—, —S—, —NH—, —NR$^{xx}$—, —SiR$^{xx}$R$^{yy}$—, —CO—, —COO—, —OCO—, —OCO—O—, —S—CO—, —CO—S—, —NR$^{xx}$—

CO—O—, —O—CO—NR$^{xx}$—, —NR$^{xx}$—CO—NR$^{yy}$—, —CH=CH— or —C≡C— in such a way that O and/or S atoms are not linked directly to one another, R$^{xx}$ and R$^{yy}$ each, independently of one another, denote H or alkyl having 1 to 12 C atoms.

and/or

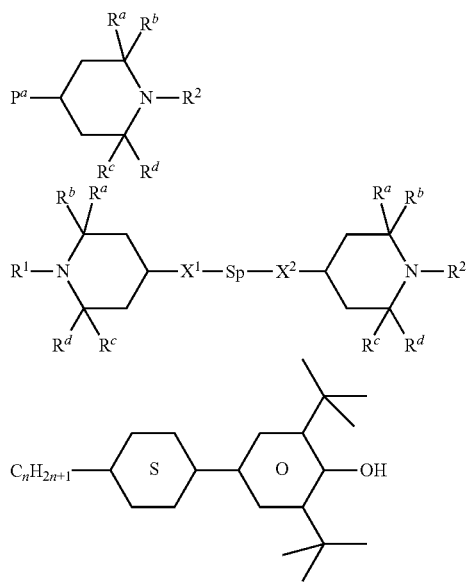

wherein the individual radicals, independently of each other and on each occurrence identically or differently, have the following meanings:

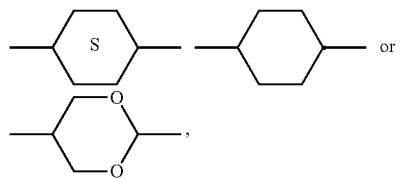

P$^a$ is a polymerizable group, preferably a (meth)acrylate group,

Sp straight chain or branched alkylene having 1 to 12 C atoms, where, in addition, one or two non-adjacent CH$_2$ groups may be replaced by —O—, —CH=CH—, —CO—, —OCO— or —COO— in such a way that O atoms are not linked directly to one another, X$^1$ and X$^2$ denote each and independently —O—, —CH=CH—, —CF$_2$O—, —OCF$_2$—, —CH$_2$O—, —OCH$_2$—, —CO—O—, —O—CO—, —C$_2$F$_4$—, —CF=CF— or a single bond, preferably —O—, —CO—O—, —O—CO—, R$^{a-d}$ denote each and independently straight chain or branched alkyl with 1 to 20 C atoms, preferably with 1 to 15 C atoms, very preferably with 1 to 12 C atoms, R$^1$ and R$^2$ denote each and independently H, CH$_3$, OH, OR$^a$ or O., and n denotes an integer between 1 and 8.

Typical commercially available examples of stabilizers are e.g. HALS type stabilizers such as Tinuvin 770, Uvinul 3049 and/or Tinuvin 970 all available from BASF, Germany, and/or LA-F70 available from Adeka, Japan, preferably in an amount of 0.1 to 5% by weight, very preferably 0.2 to 3% by weight.

In another preferred embodiment the RM formulation comprises one or more solvents, which are preferably selected from organic solvents. The solvents are preferably selected from ketones such as acetone, methyl ethyl ketone, methyl propyl ketone, methyl isobutyl ketone or cyclohexanone; acetates such as methyl, ethyl or butyl acetate or methyl acetoacetate; alcohols such as methanol, ethanol or isopropyl alcohol; aromatic solvents such as toluene or xylene; alicyclic hydrocarbons such as cyclopentane or cyclohexane; halogenated hydrocarbons such as di- or trichloromethane; glycols or their esters such as PGMEA (propyl glycol monomethyl ether acetate), γ-butyrolactone. It is also possible to use binary, ternary or higher mixtures of the above solvents.

In case the RM formulation contains one or more solvents, the total concentration of all solids, including the RMs, in the solvent(s) is preferably from 10 to 60%.

Polymerisation of the RMs is preferably carried out in the presence of an initiator absorbing at the wavelength of the actinic radiation. For this purpose, preferably the RM formulation contains one or more polymerisation initiators. In another preferred embodiment, the polymerisable LC material comprises a one or more, more preferably of one or two photoinitiators, for example, selected from the commercially available Irgacure® or Darocure® (Ciba AG) series, in particular, Irgacure 127, Irgacure 184, Irgacure 369, Irgacure 651, Irgacure 817, Irgacure 907, Irgacure 1300, Irgacure, Irgacure 2022, Irgacure 2100, Irgacure 2959, or Darcure TPO, further selected from the commercially available OXE02 (Ciba AG), NCI 930, N1919T (Adeka), SPI-03 or SPI-04 (Samyang), or preferably combinations thereof, such as SPI-03 and NCI-930.

The concentration of the polymerisation initiator(s) as a whole in the RM formulation is preferably from 0.1 to 10%, very preferably from 0.5 to 8%, more preferably 2 to 6%.

Preferably, the polymerisable LC material comprises besides one or more compounds of formula I,
a) one or more di- or multireactive polymerisable mesogenic compounds,
b) optionally one or more monoreactive polymerisable mesogenic compounds,
c) optionally one or more antioxidative additives,
d) optionally one or more adhesion promotors,
e) optionally one or more surfactants,
f) optionally one or more mono-, di- or multireactive polymerisable non-mesogenic compounds,
g) optionally one or more dyes showing an absorption maximum at the wavelength used to initiate photo polymerisation,
h) optionally one or more chain transfer agents,
i) optionally one or more stabilizers,
j) optionally one or more lubricants and flow auxiliaries, and
k) optionally one or more diluents,
l) optionally a non-polymerisable nematic component.

More preferably, the polymerisable LC material comprises,
a) one or more compounds of formula I, and
b) one or more, preferably two or more, direactive polymerisable mesogenic compounds, preferably in an amount, if present at all, of 10 to 90% by weight, very preferably 15 to 75% by weight, preferably selected from the compounds of formula DRMa-1, and/or c) one or more, preferably two or more, monoreactive polymerisable mesogenic compounds, preferably in an amount of 10 to 95% by weight, very preferably 25 to 85%, preferably selected from compounds of formulae MRM-1 and/or MRM-7, and/or d) one or more compounds of formula ND in the preferably in an amount of 1 to 50%, more preferably from 1 to 40%, and/or e) one or more antioxidative additives, preferably selected from esters of unsubstituted and substituted benzoic acids, in particular Irganox®1076, and if present, preferably in an amount of 0.01 to 2% by weight, very preferably 0.05 to 1% by weight, and/or f) one or more lubricants and flow auxiliaries, preferably selected from BYK®310, BYK®388, FC 4430, Fluor N 561 and/or Fluor N 562, and if present, preferably in an amount of 0.1 to 5% by weight, very preferably 0.2 to 3% by weight, and/or g) optionally one or more photoinitiators, preferably selected from SPI-03 and/or Adeka NCI-930, and if present, preferably in an amount of 0.1 to 5% by weight, very preferably 0.2 to 3% by weight, and/or h) optionally one or more stabilizers, preferably selected from HALS type stabilizers, such as Tinuvin 770, Uvinul 3049 and/or Tinuvin 970, and/or LA-F70, and if present, preferably in an amount of 0.1 to 5% by weight, very preferably 0.2 to 3% by weight.

The preparation of polymers according to this invention can be carried out by methods that are known to the skilled person and described in the literature, for example in D. J. Broer; G. Challa; G. N. Mol, *Macromol. Chem,* 1991, 192, 59.

Typically the RM, RM mixture or RM formulation is coated or otherwise applied onto a substrate, for example by a coating or printing method, where the RMs are aligned into uniform orientation. Preferably the RMs are aligned into planar alignment, i.e. with the long molecular axes of the RM molecules aligned parallel to the substrate. However it is likewise preferred to align the RMs into a homeotropic alignment or into a tilted alignment.

The aligned RMs are then polymerised in situ, preferably at a temperature where they exhibit an LC phase, for example by exposure to heat or actinic radiation. Preferably the RMs are polymerised by photo-polymerisation, very preferably by UV-photopolymerisation, to fix the uniform alignment. If necessary, uniform alignment can be promoted by additional means like shearing or annealing of the RMs, surface treatment of the substrate, or adding surfactants to the RM mixture or the RM formulation.

As substrate for example glass or quartz sheets or plastic films can be used. It is also possible to put a second substrate on top of the coated material prior to and/or during and/or after polymerisation. The substrates can be removed after polymerisation or not. When using two substrates in case of curing by actinic radiation, at least one substrate has to be transmissive for the actinic radiation used for the polymerisation. Isotropic or birefringent substrates can be used. In case the substrate is not removed from the polymerised film after polymerisation, preferably isotropic substrates are used.

Suitable and preferred plastic substrates are for example films of polyester such as polyethyleneterephthalate (PET) or polyethylene-naphthalate (PEN), polyvinylalcohol (PVA), polycarbonate (PC) or triacetylcellulose (TAC), very preferably PET or TAC films. As birefringent substrates for example uniaxially stretched plastics film can be used. PET films are commercially available for example from DuPont Teijin Films under the trade name Melinex®.

Preferably the RMs and the other solid additives are dissolved in a solvent. The solution is then coated or printed onto the substrate, for example by spin-coating or printing or other known techniques, and the solvent is evaporated off before polymerisation. In many cases it is suitable to heat the coated solution in order to facilitate the evaporation of the solvent.

The RM formulation can be applied onto the substrate by conventional coating techniques like spin-coating or blade coating. It can also be applied to the substrate by conventional printing techniques which are known to the expert, like for example screen printing, offset printing, reel-to-reel printing, letter press printing, gravure printing, rotogravure printing, flexographic printing, intaglio printing, pad printing, heat-seal printing, ink-jet printing or printing by means of a stamp or printing plate.

In a preferred embodiment the RM formulation exhibits planar alignment. This can be achieved for example by rubbing treatment of the substrate, by shearing the material during or after coating, by annealing the material before polymerisation, by application of an alignment layer, by applying a magnetic or electric field to the coated material, or by the addition of surface-active compounds to the formulation. Reviews of alignment techniques are given for example by I. Sage in "Thermotropic Liquid Crystals", edited by G. W. Gray, John Wiley & Sons, 1987, pages 75-77; and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

It is also possible to apply an alignment layer onto the substrate and provide the RM mixture or RM formulation onto this alignment layer. Suitable alignment layers are known in the art, like for example rubbed polyimide or alignment layers prepared by photoalignment as described in U.S. Pat. No. 5,602,661, 5,389,698 or 6,717,644.

It is also possible to induce or improve alignment by annealing the RMs at elevated temperature, but below their clearing temperature, prior to polymerisation.

Polymerisation is achieved for example by exposing the polymerisable material to heat or actinic radiation. Actinic radiation means irradiation with light, like UV light, IR light or visible light, irradiation with X-rays or gamma rays or irradiation with high energy particles, such as ions or electrons.

Preferably polymerisation is carried out by UV irradiation. As a source for actinic radiation for example a single UV lamp or a set of UV lamps can be used. When using a high lamp power the curing time can be reduced. Another possible source for actinic radiation is a laser, like for example a UV, IR or visible laser.

The curing time depends, inter alia, on the reactivity of the RMs, the thickness of the coated layer, the type of polymerisation initiator and the power of the UV lamp. The curing time is preferably ≤5 minutes, very preferably ≤3 minutes, most preferably ≤1 minute. For mass production short curing times of ≤30 seconds are preferred.

The polymerisation process is not limited to one curing step. It is also possible to carry out polymerisation by two or more steps, in which the film is exposed to two or more lamps of the same type, or two or more different lamps in sequence. The curing temperature of different curing steps might be the same or different. The lamp power and dose from different lamps might also be the same or different. In addition to the conditions described above, the process steps may also include a heat step between exposure to different lamps, as described for example in JP 2005-345982 A and JP 2005-265896 A.

Preferably polymerisation is carried out in air, but polymerising in an inert gas atmosphere like nitrogen or argon is also possible.

The thickness of a polymer film according to the present invention is preferably less than 15 microns, very preferably less than 12 microns most preferably less than 10 microns.

The RMs, RM mixtures, RM formulations and polymers of the present invention can be used in optical, electro optical or electronic devices or components thereof.

For example, they can be used in optical retardation films, polarizers, compensators, beam splitters, reflective films, alignment layers, color filters, antistatic protection sheets, or electromagnetic interference protection sheets, polarization controlled lenses for autostereoscopic 3D displays, RM lenses and IR reflection films for window applications.

The RMs, RM mixtures, RM formulations, polymers and device components of the present invention can be used for example in devices selected from electro optical displays, especially liquid crystal displays (LCDs), autostereoscopic 3D displays, organic light emitting diodes (OLEDs), optical data storage devices, and window applications.

The RMs, RM mixtures, RM formulations, polymers and device components of the present invention can be used outside the switchable LC cell of an LCD or between the substrates, usually glass substrates, forming the switchable LC cell and containing the switchable LC medium (incell application).

The RMs, RM mixtures, RM formulations, polymers and device components of the present invention can be used in conventional LC displays, for example displays with vertical alignment like the DAP (deformation of aligned phases), ECB (electrically controlled birefringence), CSH (colour super homeotropic), VA (vertically aligned), VAN or VAC (vertically aligned nematic or cholesteric), MVA (multi-domain vertically aligned), PVA (patterned vertically aligned) or PSVA (polymer stabilised vertically aligned) mode; displays with bend or hybrid alignment like the OCB (optically compensated bend cell or optically compensated birefringence), R-OCB (reflective OCB), HAN (hybrid aligned nematic) or pi-cell (π-cell) mode; displays with twisted alignment like the TN (twisted nematic), HTN (highly twisted nematic), STN (super twisted nematic), AMD-TN (active matrix driven TN) mode; displays of the IPS (in plane switching) mode, or displays with switching in an optically isotropic phase.

The RMs, RM mixtures, RM formulations and polymers of the present invention can be used for various types of optical films such as, A-plates, +C plates, O-plates for use in LCD compensation and/or OLED anti-reflection/optical compensation.

Unless stated otherwise, the percentages of solid components in an RM mixture or RM formulation as described above and below refer to the total amount of solids in the mixture or formulation, i.e. without any solvents.

Unless stated otherwise, all optical, electro optical properties and physical parameters like birefringence, permittivity, electrical conductivity, electrical resistivity and sheet resistance, refer to a temperature of 20° C.

Unless the context clearly indicates otherwise, as used herein plural forms of the terms herein are to be construed as including the singular form and vice versa.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The following examples are intended to explain the invention without restricting it. The methods, structures and properties described hereinafter can also be applied or transferred to materials that are claimed in this invention but not explicitly described in the foregoing specification or in the examples.

EXAMPLES

Compound Examples

Compound Example 1

Compound (RM-1) is prepared as described below:

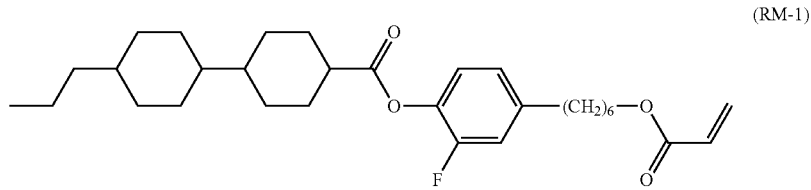

(RM-1)

1.1 Preparation of 2-fluoro-4-(6-hydroxyhex-1-yn-1-yl)phenol

4-Bromo-2-fluorophenol (9.55 g, 50 mmol) and diisopropylamine (75 ml, 536 mmol) are mixed to give a solid. Hexyn-5-ol (4.5 g, 46 mmol) is added and the mixture is ultrasonicated for 30 minutes. Copper(I)iodide (285 mg, 1.5 mmol), palladium(II)acetate (570 mg, 2 mmol) and tri(tert-butylphosphonium)tetrafluoroborate (645 mg, 2.2 mmol) are added and the mixture heated at 40° C. for 4 hours. The mixture is cooled and poured into a mixture of concentrated hydrochloric acid (75 ml) and ice (150 g). The mixture is extracted with ethyl acetate (300 and 2×200 ml). The solvent from the combined organic extracts are removed in vacuo.

The residue is dissolved in DCM (50 ml) and purified by vacuum flash chromatography on silica (120 g) eluting with a gradient of DCM:ethyl acetate:IPA. Product containing fractions are combined and the solvent removed in vacuo. The oil (5.6 g) was dissolved in DCM (50 ml) and purified by vacuum flash chromatography on silica (120 g) eluting a gradient of DCM:ethyl acetate:IPA. Product containing fractions were combined and the solvent removed in vacuo (5.5 g). The oil (5.5 g) was dissolved in DCM (50 ml) and purified by vacuum flash chromatography on basic alumina (120 g) eluting with a gradient of DCM:ethyl acetate:IPA. The column was then eluted with a gradient of DCM/methanol. The fractions containing the product are combined and the solvent removed in vacuo to give the desired product—2-fluoro-4-(6-hydroxyhex-1-yn-1-yl)phenol (3.87 g, 37% yield).

1.2 Preparation of 2-fluoro-4-(6-hydroxyhexyl)phenol (APN M1859)

2-fluoro-4-(6-hydroxyhex-1-yn-1-yl)phenol (APN M1825, 3.87 g, 18.6 mmol), palladium on carbon (10%, 1 g) and THF (100 ml) are hydrogenated at room temperature for 7 hours. The catalyst is filtered off through celite and solvent removed in vacuo. The residue is dissolved in DCM and purified by vacuum flash chromatography on silica (120 g) eluting with a gradient of DCM:ethyl acetate:IPA. Product containing fractions are combined and the solvent is removed in vacuo to give the desired product 2-fluoro-4-(6-hydroxyhexyl)phenol (1.61 g, 41% yield).

1.3 Preparation of 6-(3-fluoro-4-hydroxyphenyl)hexyl 3-chloropropanoate 2-fluoro-4-(6-hydroxyhexyl)phenol (1.61 g, 7.6 mmol), 3-chloropropanoic acid (1 g, 9.2 mmol), p-toluenesulphonic acid (1 g) and toluene (20 ml) are refluxed for 3 hours using a Dean Stark apparatus. The mixture is cooled, washed with water (2×20 ml) and the solvent is removed in vacuo. The residue is dissolved in DCM and purified by vacuum flash chromatography on silica (60 g) eluting with a gradient of DCM:ethyl acetate. Product containing fractions are combined and the solvent removed in vacuo to give the desired product 6-(3-fluoro-4-hydroxyphenyl)hexyl 3-chloropropanoate (1.9 g, 83% yield).

1.4 Preparation of RM-1

6-(3-fluoro-4-hydroxyphenyl)hexyl 3-chloropropanoate (APN M1865, 1.9 g, 6.3 mmol), trans-4-(trans-4'-n-propylcyclohexyl)cyclohexane carboxylic acid (1.7 g, 6.7 mmol), DMAP (0.8 g, 6.6 mmol) and DCM (10 ml) are stirred at room temperature. DCC (10 ml, 1M in DCM, 10 mmol) is added in one portion and the mixture stirred overnight. Triethylamine (10 ml, 72 mmol) is added and the mixture is stirred for 8 hours at 40° C. The mixture is cooled. Concentrated hydrochloric acid (10 ml) and water (50 ml) are mixed and added to the reaction mixture. The mixture is stirred for 30 minutes, filtered, washed with DCM. The two layers from the filtrate are separated and the aqueous layer extracted with DCM (2×50 ml). The organic layers are dried over anhydrous sodium sulphate, filtered and the solvent from the filtrate is removed in vacuo. The residue is dissolved in DCM:petrol 1:1 and purified by vacuum flash chromatography on silica (60 g) eluting with a gradient of Petrol/DCM. Product containing fractions are combined and the solvent removed in vacuo. The product is crystallised from a mixture of DCM (2 ml) and petrol (30 ml). The mixture is cooled in the fridge for 1 hour, filtered off, washed with cold petrol and dried to give the desired product RM-1 as a white solid (2.18 g, 69% yield).

Phase behaviour: K-N(S) 50.9° C. S-N 100.9° C. N-I 165.2° C.

Nematic range 64.3° C.

LC range 114.3° C.

$^1$H NMR (400 MHz, Chloroform-d) δ 7.02-6.87 (m, 1H), 6.39 (dd, J=17.3, 1.4 Hz, OH), 6.12 (dd, J=17.3, 10.4 Hz, OH), 5.81 (dd, J=10.4, 1.5 Hz, OH), 4.14 (t, J=6.6 Hz, 1H), 2.58 (t, J=7.7 Hz, 1H), 2.49 (tt, J=12.2, 3.6 Hz, OH), 2.21-2.11 (m, 1H), 1.88-1.79 (m, 1H), 1.80-1.71 (m, 1H), 1.72-1.47 (m, 2H), 1.46-1.23 (m, 2H), 1.06 (dddd, J=48.2, 24.4, 10.7, 3.1 Hz, 3H), 0.87 (t, J=7.2 Hz, 2H).

$^{13}$C NMR (101 MHz, Chloroform-d) δ 174.07, 166.47, 155.16, 152.69, 142.15, 142.08, 136.24, 136.11, 130.65, 128.73, 124.26, 124.23, 123.40, 123.38, 116.56, 116.38, 64.71, 43.55, 43.36, 42.62, 39.93, 37.73, 35.35, 33.67, 31.14, 30.14, 29.43, 29.25, 28.90, 28.67, 25.93, 20.18, 14.57.

Compound Example 2

Compound (RM-2) is prepared as described below:

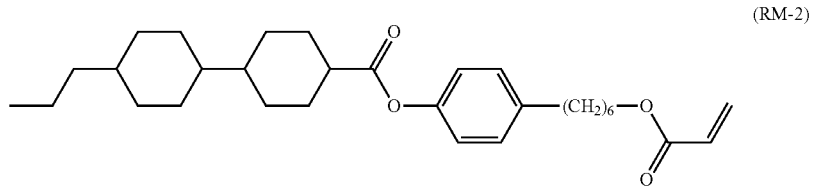
(RM-2)

2.1 Preparation of 6-(4-hydroxyphenyl)hexyl propanoate 4-(6-hydroxyhexyl)phenol (71.7 g, 369 mmol), 3-chloropropanoic acid (44.06 g, 406 mmol), p-toluenesulphonic acid (5 g) and DCM (500 ml) are refluxed for 8 hours using a reverse Dean Stark apparatus. The mixture is cooled, washed with water (500 ml). The organic layer are dried over anhydrous sodium sulphate, filtered and the solvent from the filtrate is removed in vacuo. The oil is dissolved in DCM and passed down a plug of silica eluting with DCM to give the desired product as a colourless oil—6-(4-hydroxyphenyl)hexyl propanoate (89.8 g, 86% yield).

Preparation of RM-2

4'-propyl-[1,1'-bi(cyclohexane)]-4-carboxylic acid ((Merck, 2.79653) 3.78 g, 15 mmol), 6-(4-hydroxyphenyl)hexyl propanoate (4.27 g, 15 mmol), DMAP (1.83 g, 15 mmol) and DCM (50 ml) are stirred at room temperature. DCC (20 ml, 1M in DCM, 20 mmol) is added and the mixture stirred overnight. Triethylamine (25 ml, 179 mmol), Irganox 1076 (few crystals) are added and the mixture stirred at 35° C. overnight. The mixture is cooled. Water (75 ml) and concentrated hydrochloric acid (25 ml) are mixed, added and stirred for 1 hour. The mixture is filtered and washed with DCM. The two layers are separated and the aqueous layer is extracted with DCM (2×50 ml). The combined organic layers are dried over anhydrous sodium sulphate, filtered and the solvent from the filtrate is removed in vacuo. The residue is dissolved in petrol:DCM (50 ml):(50 ml) and purified by vacuum flash chromatography on silica (120 g) eluting with a gradient of Petrol:DCM Fractions containing product are combined and the solvent removed in vacuo.

The product is crystallised from isopropyl alcohol (50 ml), cooled in the fridge for 1 hour, filtered off, washed with cold isopropyl alcohol to give the desired product RM-2 as a white solid (5.56 g, 77% yield).

Phase behaviour: K-N(S) 40.7° C. S-N 120.7° C. N-I 158.1° C.

Nematic range 37.4° C.

LC range 117.4° C.

$^1$H NMR (400 MHz, Chloroform-d) δ 7.18-7.11 (m, 2H), 6.99-6.91 (m, 2H), 6.39 (dd, J=17.3, 1.5 Hz, 1H), 6.11 (dd, J=17.3, 10.4 Hz, 1H), 5.81 (dd, J=10.4, 1.5 Hz, 1H), 4.14 (t, J=6.7 Hz, 2H), 2.59 (t, J=7.7 Hz, 2H), 2.44 (tt, J=12.2, 3.6 Hz, 1H), 2.20-2.10 (m, 2H), 1.86 (s, 1H), 1.84-1.80 (m, 1H), 1.77 (d, J=2.8 Hz, 1H), 1.76-1.58 (m, 6H), 1.55-1.45 (m, 2H), 1.46-1.23 (m, 5H), 1.19-1.07 (m, 5H), 1.07-1.04 (m, 1H), 1.04-0.98 (m, 2H), 0.98-0.91 (m, 1H), 0.87 (t, J=7.3 Hz, 5H).

$^{13}$C NMR (101 MHz, Chloroform-d) δ 175.04, 166.47, 148.95, 140.05, 130.62, 129.32, 128.75, 121.35, 64.76, 43.84, 43.38, 42.66, 39.93, 37.73, 35.36, 33.67, 31.44, 30.15, 29.44, 29.29, 28.97, 28.68, 25.95, 20.18, 14.57.

Compound Example 3

Compound (RM-3) is prepared as described below:

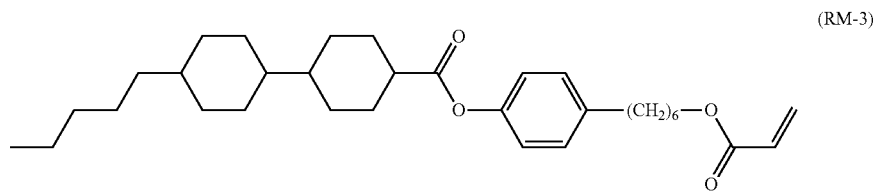

(RM-3)

3.1 Preparation of 6-(4-hydroxyphenyl)hexyl propanoate 4-(6-hydroxyhexyl)phenol (71.7 g, 369 mmol), 3-chloropropanoic acid (44.06 g, 406 mmol), p-toluenesulphonic acid (5 g) and DCM (500 ml) are refluxed for 8 hours using a reverse Dean Stark apparatus. The mixture is cooled, washed with water (500 ml). The organic layer are dried over anhydrous sodium sulphate, filtered and the solvent from the filtrate removed in vacuo. The oil is dissolved in DCM and passed down a plug of silica eluting with DCM to give the desired product as a colourless oil—6-(4-hydroxyphenyl)hexyl propanoate (89.8 g, 86% yield).

3.2 Preparation of RM-3

4'-pentyl-[1,1'-bi(cyclohexane)]-4-carboxylic acid ((Merck, 2.79656) 4.2 g, 15 mmol), 6-(4-hydroxyphenyl)hexyl propanoate (4.27 g, 15 mmol), DMAP (1.83 g, 15 mmol) and DCM (50 ml) are stirred at room temperature. DCC (20 ml, 1M in DCM, 20 mmol) is added and the mixture stirred overnight. Triethylamine (25 ml, 179 mmol), Irganox 1076 (few crystals) are added and the mixture stirred at 35° C. overnight. The mixture is cooled. Water (75 ml) and concentrated hydrochloric acid (25 ml) are mixed, added and stirred for 1 hour. The mixture is filtered and washed with DCM. The two layers are separated and the aqueous layer extracted with DCM (2×50 ml). The combined organic layers are dried over anhydrous sodium sulphate, filtered and the solvent from the filtrate is removed in vacuo. The residue is dissolved in petrol:DCM (50 ml):(50 ml) and purified by vacuum flash chromatography on silica (120 g) eluting with a gradient of petrol:DCM Fractions containing product are combined and the solvent removed in vacuo. The product is crystallised from isopropyl alcohol (50 ml), cooled in the fridge for 1 hour, filtered off, washed with cold isopropyl alcohol to give the desired product RM-3 as a white solid (6.06 g, 79% yield).

Phase behaviour: K-N(S) 45.8° C. S-N 1145° C. N-I 158.1° C.

Nematic range 13.6° C.

LC range 112.3° C.

$^1$H NMR (400 MHz, Chloroform-d) δ 7.15 (d, J=8.3 Hz, 2H), 6.99-6.91 (m, 2H), 6.39 (dd, J=17.3, 1.4 Hz, 1H), 6.11 (dd, J=17.3, 10.4 Hz, 1H), 5.81 (dd, J=10.4, 1.5 Hz, 1H), 4.14 (t, J=6.7 Hz, 2H), 2.59 (t, J=7.7 Hz, 2H), 2.44 (tt, J=12.2, 3.6 Hz, 1H), 2.20-2.09 (m, 2H), 1.88-1.80 (m, 2H), 1.80-1.57 (m, 7H), 1.52 (dd, J=12.5, 3.2 Hz, 2H), 1.48-1.18 (m, 10H), 1.19-1.07 (m, 5H), 1.07-0.91 (m, 4H), 0.88 (t, J=6.9 Hz, 5H).

$^{13}$C NMR (101 MHz, Chloroform-d) δ 175.37, 166.79, 149.27, 140.37, 130.94, 129.64, 129.07, 121.67, 65.08, 44.16, 43.70, 42.97, 38.34, 37.90, 35.67, 34.02, 32.70, 31.76, 30.47, 29.76, 29.61, 29.29, 29.00, 27.13, 26.27, 23.18, 14.59.

Compound Example 4

Compound (RM-4) is prepared as described below:

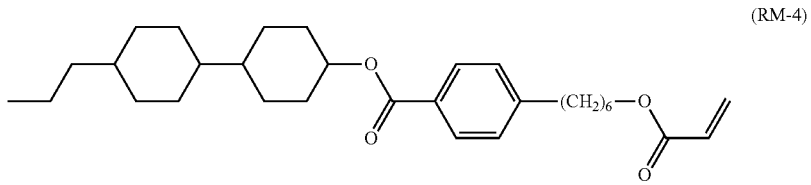

(RM-4)

4.1 Preparation of 4-(6-hydroxyhex-1-yn-1-yl)benzoic acid 4-iodobenzoic acid (100 g, 403 mmol) is dissolved in THF (500 ml) and triethylamine (50 ml, 359 mmol). Copper (I) iodide (1 g, 190 mmol) and Bis(triphenylphosphine) palladium dichloride (10 g, 14 mmol) is added, hex-5-yn-1-ol (40 g, 407 mmol) is added slowly with cooling, then heated to 50° C. overnight. Reaction is cooled and filtered. The solvent is removed in vacuo. DCM and dilute acid are added to wash and remove residual triethylamine. The residue is chromatographed on silica eluting with THF/Petrol. The fractions containing the product are evaporated in vacuo. The residue is chromatographed on silica eluting with Petrol and then ether/petrol. The fractions containing the product are evaporated in vacuo to give the desired product as an off white solid—4-(6-hydroxyhex-1-yn-1-yl) benzoic acid (26 g, 29.5% yield).

4.2 Preparation of 4-(6-hydroxyhexyl)benzoic acid

A solution of 4-(6-hydroxyhex-1-yn-1-yl)benzoic acid (25 g; 0.11 moles) in THF (250 ml) is stirred vigorously under a balloon of hydrogen in the presence of 5% palladium on carbon (3 g) for 24 hours. 3 g of 10% palladium on carbon is added and the reaction stirred for a further 24 hours at 30° C. 3 g of 10% palladium on carbon is added and the mixture stirred again for 24 hours at 30° C. The mixture is filtered through celite, washed through with THF then evaporated in vacuo. The residue is crystallized upon addition of 1:1 DCM:petroleum ether (150 ml) and cooling to −20° C. The mixture is filtered, washed with a small amount of 1:1 DCM:petroleum ether then petroleum ether to afford the desired product as a white solid—4-(6-hydroxyhexyl) benzoic acid (17.1 g; 67%).

4.3 Preparation of 4-{6-[(3-chloropropanoyl)oxy]hexyl}benzoic acid

4-[6-Hydroxyhexyl)benzoic acid (30 g; 0.135 moles), 3-chloropropanoic acid (16.22 g; 0.15 moles) and PTSA monohydrate (1.70 g; 0.0089 moles) in DCM (300 ml) are refluxed (50° C.) in a Reverse Dean-Stark apparatus for 18 hours, by which time the required volume of water had been collected. After cooling, the solution is washed with water, dried over sodium sulphate and evaporated in vacuo. The residue is flash chromatographed on silica (300 g), eluting with 20% ethyl acetate in petroleum ether. Triturated with petroleum ether to yield the desired product as an off-white solid—4-{6-[(3-chloropropanoyl)oxy]hexyl}benzoic acid (42.28 g; 100%).

Preparation of Example 4

To a solution of 4-{6-[(3-chloropropanoyl)oxy]hexyl}benzoic acid (3.5 g; 0.0112 moles), DMAP (1.37 g; 0.011 moles) and 4'-propyl-[1,1'-bi(cyclohexane)]-4-carboxylic acid ((Merck, 2.79653) 2.51 g; 0.0112 moles) in DCM (30 ml) is added DCC (1M in DCM; 13.4 ml; 0.0134 moles). The resulting mixture is stirred for 1.5 hours, then triethylamine (10 ml) and a catalytic amount of Irganox 1076 were added, and the mixture heated to 40° C. for 16 hours. After cooling, petroleum ether (30 ml) is added. The resulting slurry is filtered and washed through with 1:1 DCM:Petroleum ether (2×30 ml). The filtrate is washed with 2M hydrochloric acid, water, dried with sodium sulphate then evaporated in vacuo. The residue is chromatographed on silica (150 g) eluting with DCM. The fractions containing the product are evaporated in vacuo then triturated with petroleum ether (60 ml) and cooled to −20° C. Filtration then drying in vacuo at 40° C. afforded the desired product as a white solid—RM-4 (3.2 g; 59%).

Phase behaviour: K-N(S) 69.5° C. S-N 102.0° C. N-I 145.6° C.

Nematic range 43.6° C.

LC range 76.1° C.

$^{1}$H NMR (400 MHz, Chloroform-d) δ 7.94 (d, J=8.0 Hz, 2H), 7.22 (d, J=8.1 Hz, 2H), 6.39 (dd, J=17.4, 1.4 Hz, 1H), 6.11 (dd, J=17.3, 10.4 Hz, 1H), 5.81 (dd, J=10.4, 1.4 Hz, 1H), 4.87 (tt, J=11.1, 4.4 Hz, 1H), 4.14 (t, J=6.7 Hz, 2H), 2.65 (t, J=7.7 Hz, 2H), 2.15-2.05 (m, 2H), 1.86-1.75 (m, 3H), 1.73 (s, 2H), 1.72-1.60 (m, 5H), 1.51-1.09 (m, 13H), 1.11-0.96 (m, 2H), 0.98-0.90 (m, 1H), 0.87 (t, J=7.3 Hz, 5H).

$^{13}$C NMR (101 MHz, Chloroform-d) δ 166.46, 166.32, 148.01, 130.65, 129.75, 128.72, 128.65, 128.44, 74.22, 64.71, 42.90, 42.44, 39.92, 37.68, 36.00, 33.65, 32.17, 31.17, 30.34, 28.94, 28.66, 28.11, 25.93, 20.18, 14.57.

Compound Examples 5-27
The following compounds are prepared in analogy to the synthesis examples given above:
| No. | Structure |
|---|---|
| RM-5 | 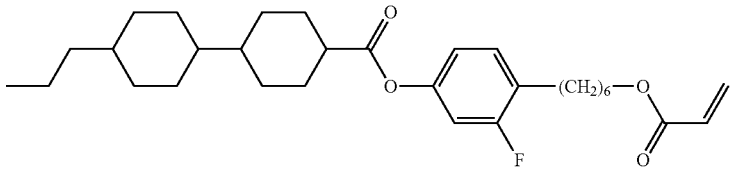 |
| RM-6 | 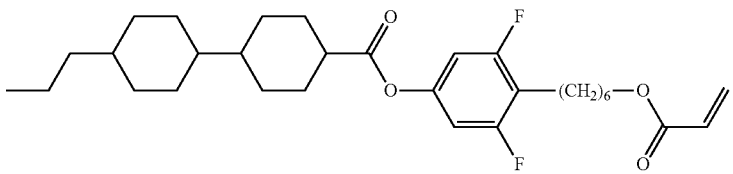 |
| RM-7 | 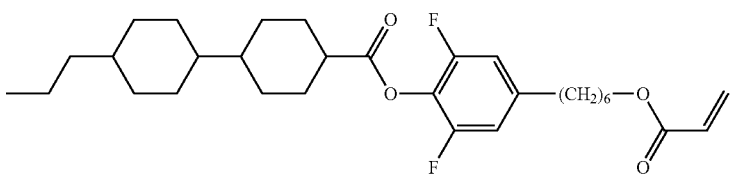 |
| RM-8 | 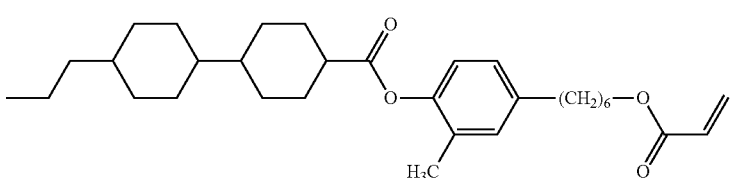 |
| RM-9 | 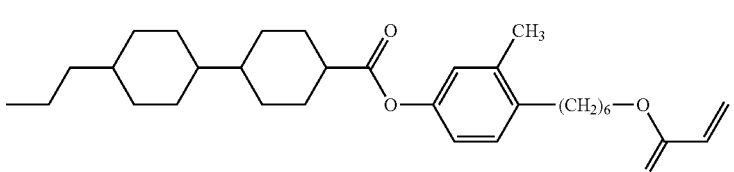 |
| RM-10 | 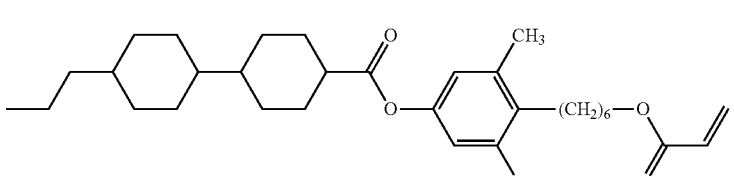 |
| RM-11 | 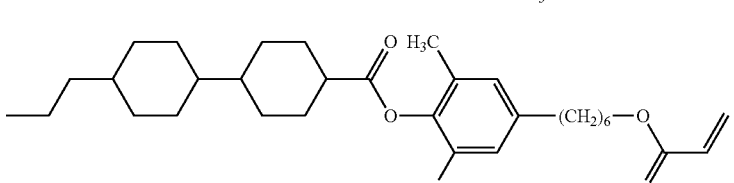 |
| RM-12 | 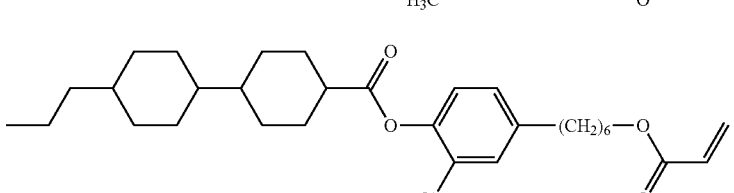 |

| No. | Structure |
|---|---|
| RM-13 | 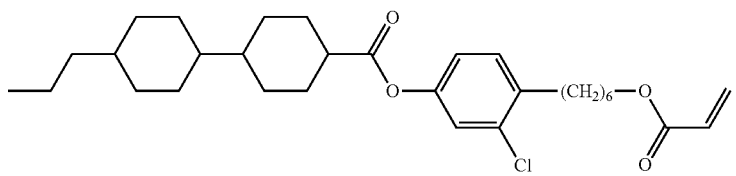 |
| RM-14 | 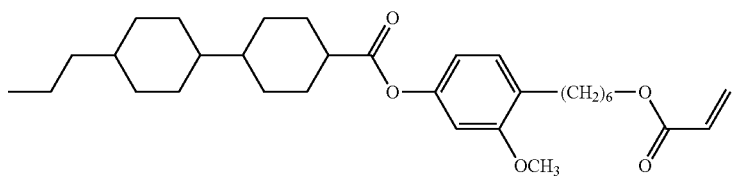 |
| RM-15 | 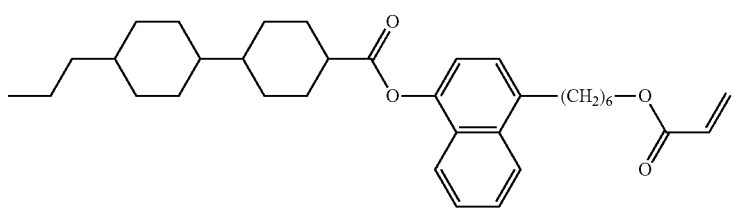 |
| RM-16 | 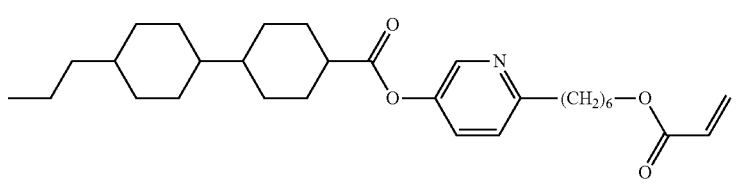 |
| RM-17 | 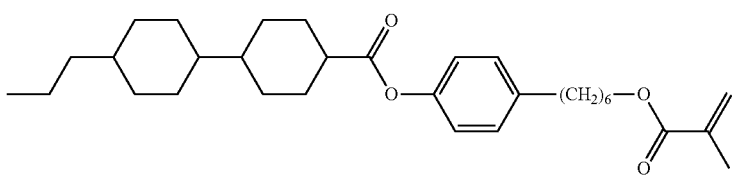 |
| RM-18 | 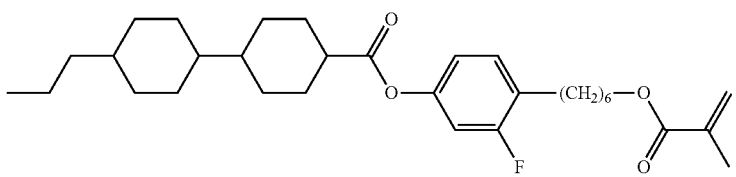 |
| RM-19 | 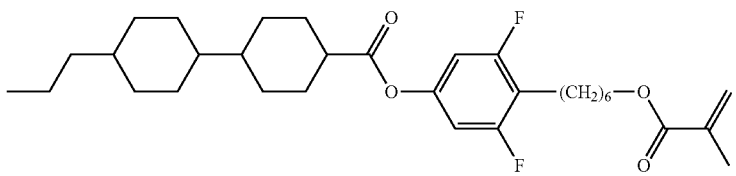 |
| RM-20 | 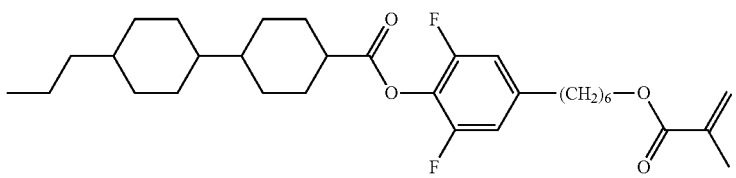 |

-continued
| No. | Structure |
|---|---|
| RM-21 | 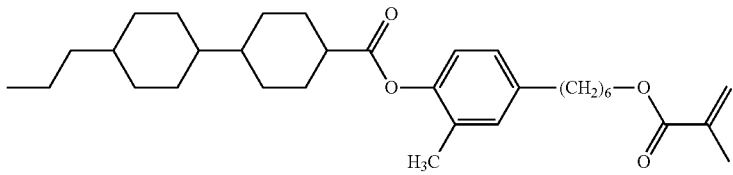 |
| RM-22 | 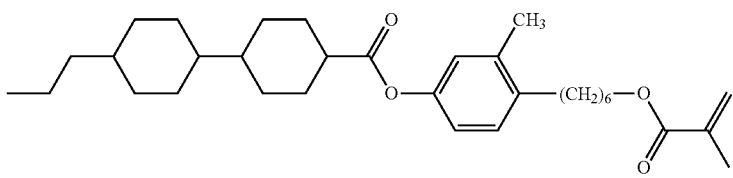 |
| RM-23 | 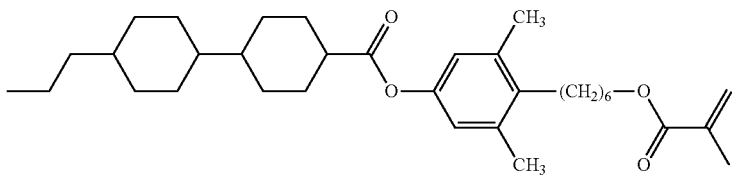 |
| RM-24 | 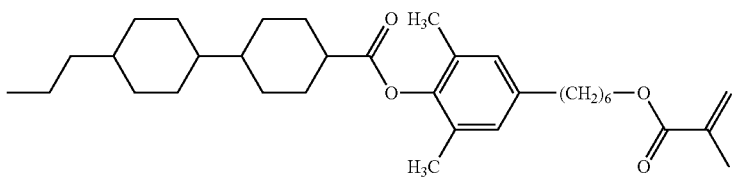 |
| RM-25 | 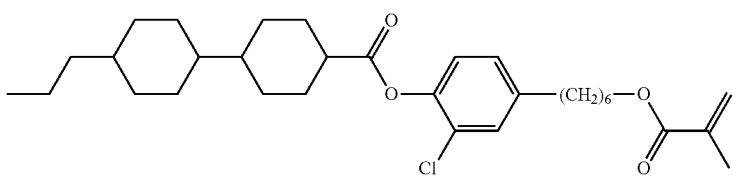 |
| RM-26 | 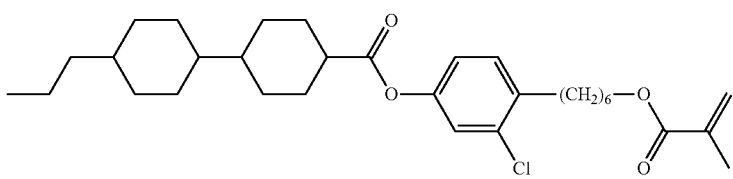 |
| RM-27 | 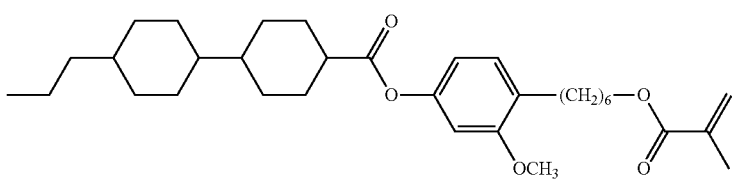 |

Comparison Example 1

Compound (C1) and compound (C3) are prepared in analogy to the synthesis described in Example 1.

| No. | Structure |
|---|---|
| C1 | ethyl-cyclohexyl-phenyl-C(=O)-O-phenyl-(CH$_2$)$_6$-O-C(=O)-CH=CH$_2$ |
| C2 | ethyl-cyclohexyl-cyclohexyl-C(=O)-O-phenyl-(CH$_2$)$_6$-O-C(=O)-CH=CH$_2$ |

Methods

Mixture Preparation

Mixtures were formulated as 33.33% solids in toluene:cyclohexanone (7:3). Heated in oven for 60 mins at 50° C. and left to cool for 10 mins. Filtered using 0.2 μm PTFE syringe filter.

Film Preparation:

For +A films, mixtures were spin coated at 1500 rpm for 30 sec onto rubbed PI glass. Annealed at 66° C. for 60 sec. Cooled for 60 sec at 20° C., under nitrogen 20 L min$^{-1}$. Cured using LED DELO lamp, 365 nm, 80 mW cm$^{-2}$, 60 sec, under nitrogen 20 L min$^{-1}$.

For +C films, mixtures were spin coated at 1000 rpm for 30 sec onto glass. Annealed at 60° C. for 60 sec. Cooled for 60 sec at 20° C., under nitrogen. Cured using Fusion Light Hammer lamp, 800 mW cm$^{-2}$, 600 mJ cm$^{-2}$ under nitrogen.

Analysis of Films

2 or 3 films were made from each mixture. Retardation was measured on the ellipsometer and the film thickness was measured. The dispersion was calculated and the average values are quoted. For ND+C films, the birefringence was also calculated and the average values are quoted.

Mixture Examples—ND+A

The following mixtures for ND+A are prepared in accordance with the following tables, polymerised and the resulting optical characteristics, such as dispersions of the resulting film are measured:

Comparison mixture CM-1: Dispersion (R450/R550)= 0.788

| Compound | %-w/w |
|---|---|
| FluorN 561 | 0.42 |
| Irganox 1076 | 0.12 |
| Darocure ®TPO | 1.00 |
| CH$_2$=CHCO$_2$(CH$_2$)$_4$OOCO-phenyl-COO-(methylphenyl)-OOC-phenyl-OCOO(CH$_2$)$_4$O$_2$CCH=CH$_2$ | 27.95 |
| CH$_2$=CHCOO(CH$_2$)$_6$O-phenyl-COO-phenyl-cyclohexyl-C$_3$H$_7$ | 15.22 |
| CH$_2$=CHCO$_2$(CH$_2$)$_6$O-phenyl-OOC-cyclohexyl-COO-phenyl-O(CH$_2$)$_6$O$_2$CCH=CH$_2$ | 15.30 |

-continued
| Compound | %-w/w |
|---|---|
| 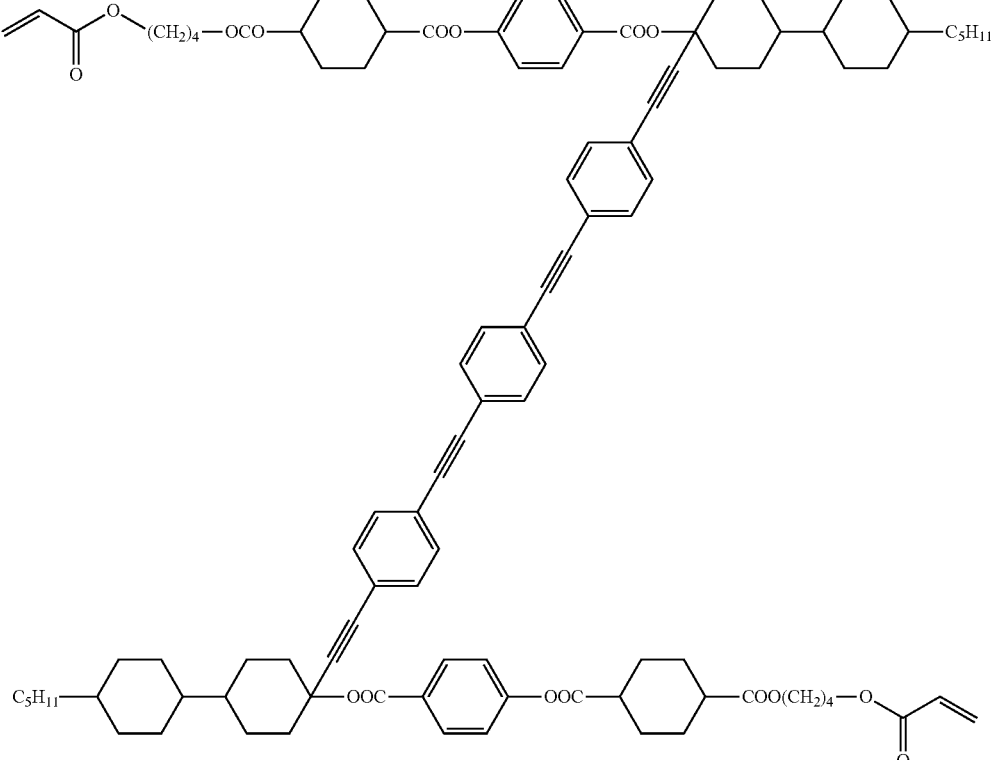 | 40.00 |
Comparison mixture CM-2: Dispersion (R450/R550)= 0.847
| Compound | %-w/w |
|---|---|
| FluorN 561 | 0.42 |
| Irganox 1076 | 0.12 |
| Darocure ®TPO | 1.00 |
| CH₂=CHCOO(CH₂)₆O—⌬—COO—⌬—⌬—C₃H₇ | 16.00 |
| | 29.38 |
| CH₂=CHCO₂(CH₂)₄OOCO—⌬—COO—⌬(CH₃)—OOC—⌬—OCOO(CH₂)₄O₂CCH=CH₂ | 16.08 |
|  | |

-continued
| Compound | %-w/w |
|---|---|
| 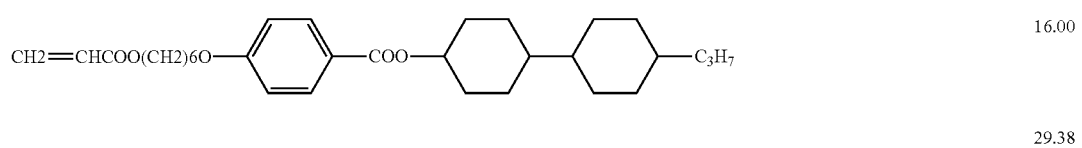 | 37.00 |
Comparison mixture CM-3: Dispersion (R450/R550)= 0.806
| Compound | %-w/w |
|---|---|
| FluorN 561 | 0.42 |
| Irganox 1076 | 0.12 |
| Darocure ®TPO | 1.00 |
| CH2=CHCOO(CH2)6O—⌬—COO—⌬—C3H7 | 16.00 |
|  | 29.38 |
| 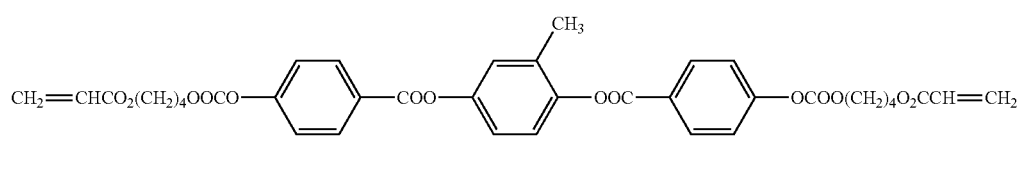 | 16.08 |
| 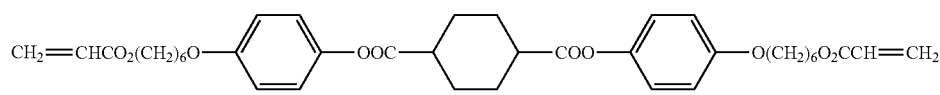 |  |

-continued

| Compound | %-w/w |
|---|---|
| 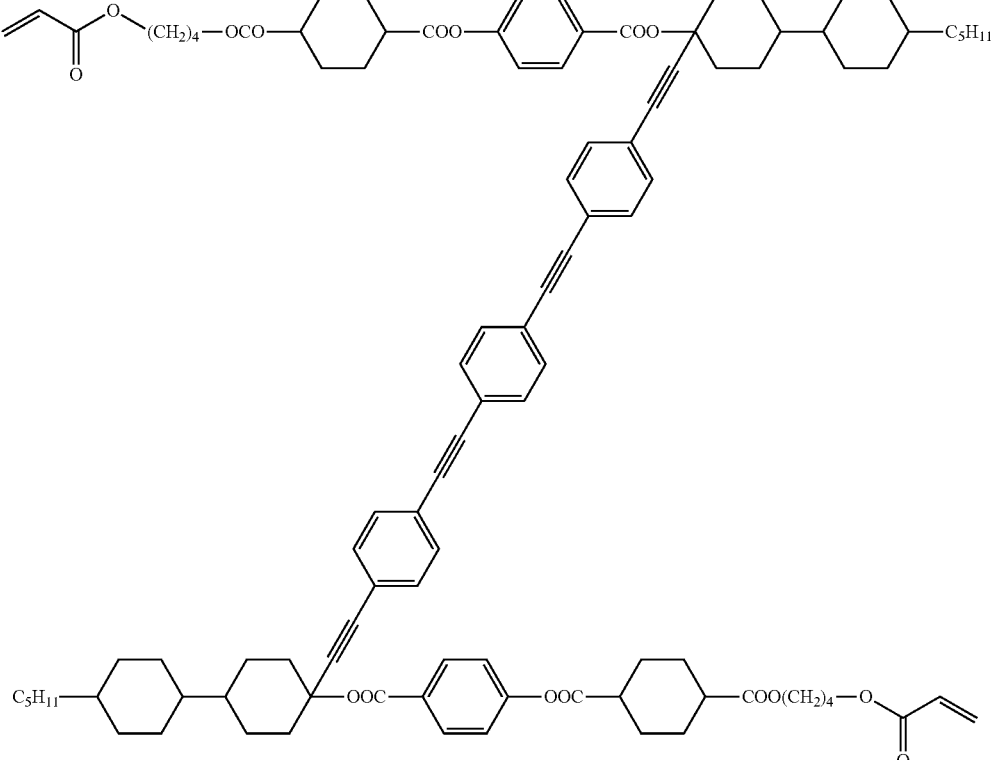 | 37.00 |

35

The difference between comparison mixtures CM-2 and CM-3 is that comparison material C1 was replaced by comparison material C2. Replacing the phenyl with a cyclohexyl results in a lower dispersion after polymerization, but the dispersion is not under 0.79, so further modification of the additive is required.

Mixture M-1: Dispersion (R450/R550)=0.778

| Compound | %-w/w |
|---|---|
| FluorN 561 | 0.42 |
| Irganox 1076 | 0.12 |
| Darocure ®TPO | 1.00 |
| RM-4 | 16.00 |
| 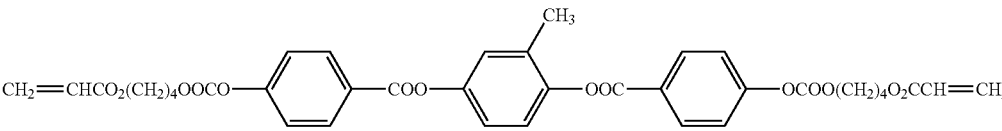 | 29.38 |
| 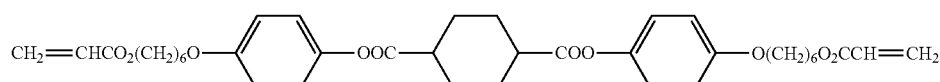 | 16.08 |

-continued
| Compound | %-w/w |
|---|---|
| 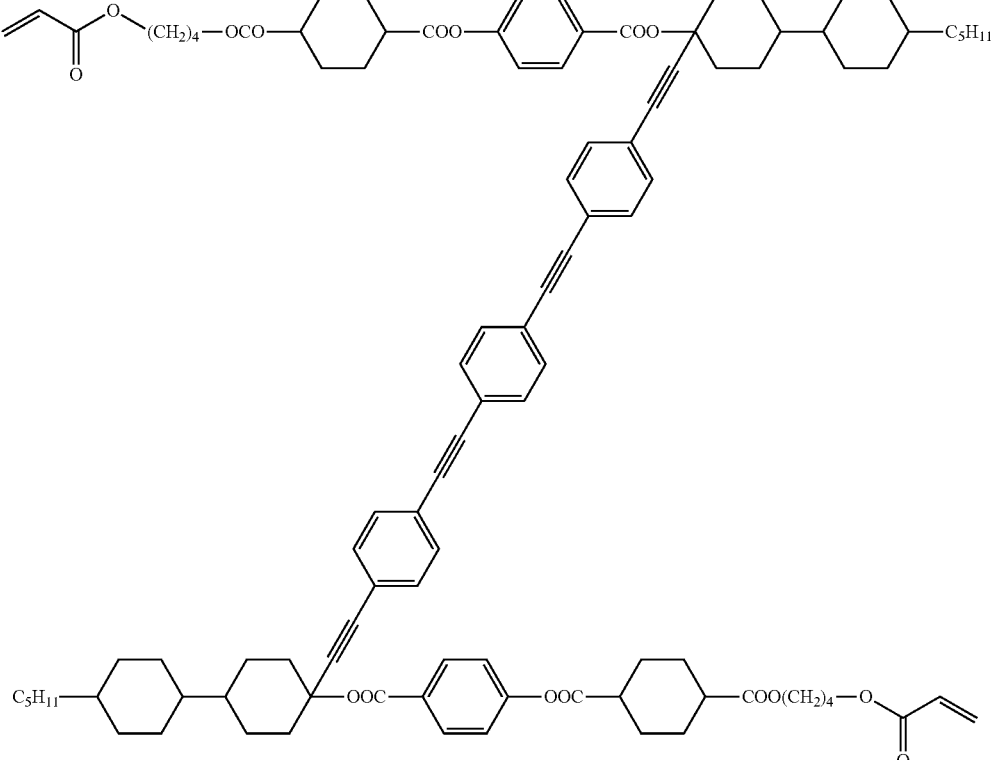 | 37.00 |
The difference between reference mixture CM-3 and example mixture M-1 is that comparison material C2 is replaced by RM-4 in accordance with the present invention. The utilization of RM-4 instead of C2 leads to a significant lower dispersion after polymerization.
Mixture M-2: Dispersion (R450/R550)=0.778
| Compound | %-w/w |
|---|---|
| FluorN 561 | 0.42 |
| Irganox 1076 | 0.12 |
| Darocure ®TPO | 1.00 |
| RM-2 | 16.00 |
| 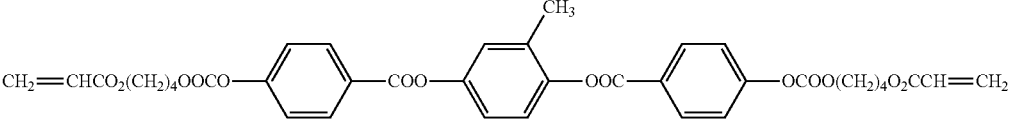 | 29.38 |
| 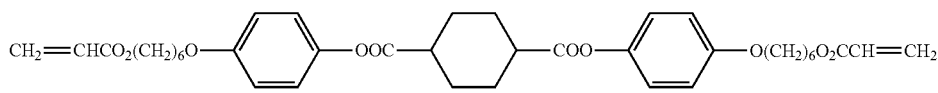 | 16.08 |

| Compound | %-w/w |
|---|---|
| 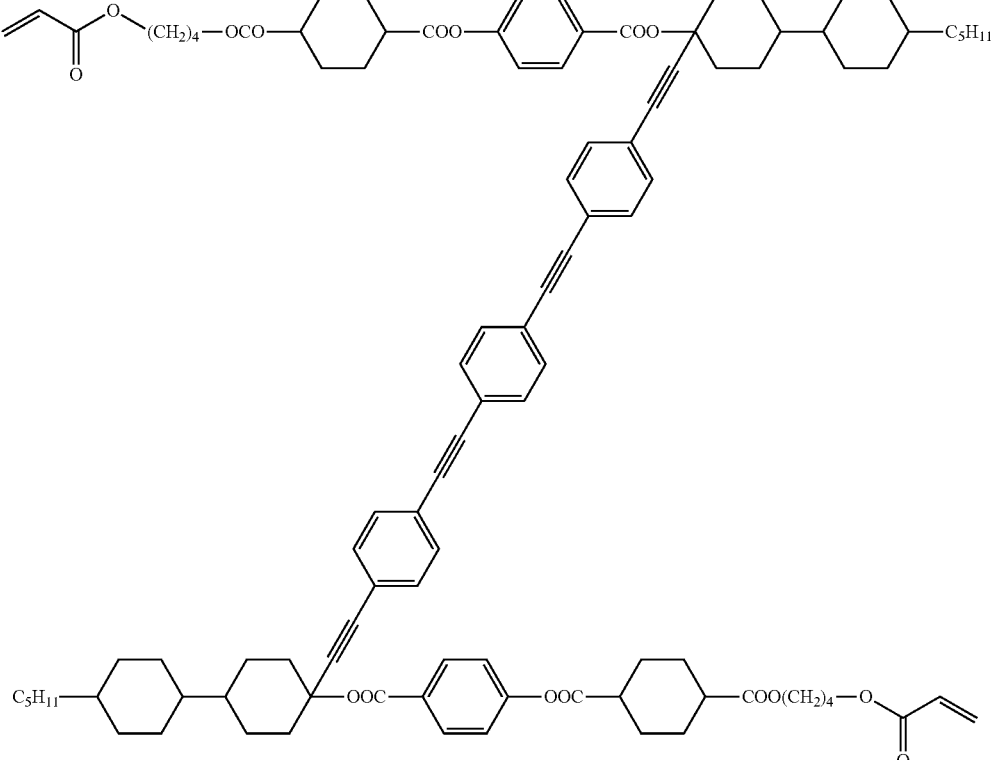 | 37.00 |

The difference between reference mixture CM-3 and example mixture M-2 is that comparison material O2 is replaced by RM-2 in accordance with the present invention. The utilization of RM-2 instead of O2 leads to a significant lower dispersion after polymerization.

Mixture M-3: Dispersion (R450/R550)=0.777

| Compound | %-w/w |
|---|---|
| FluorN 561 | 0.42 |
| Irganox 1076 | 0.12 |
| Darocure ®TPO | 1.00 |
| RM-2 | 13.33 |
| $CH_2{=}CHCOO(CH_2)_6O{-}\phantom{x}{-}COO{-}\phantom{x}{-}C_3H_7$ | 2.67 |
| $CH_2{=}CHCO_2(CH_2)_4OOCO{-}\phantom{x}{-}COO{-}\phantom{x}(CH_3){-}OOC{-}\phantom{x}{-}OCOO(CH_2)_4O_2CCH{=}CH_2$ | 29.38 |
| $CH_2{=}CHCO_2(CH_2)_6O{-}\phantom{x}{-}OOC{-}\phantom{x}{-}COO{-}\phantom{x}{-}O(CH_2)_6O_2CCH{=}CH_2$ | 16.08 |

| Compound | %-w/w |
|---|---|
| 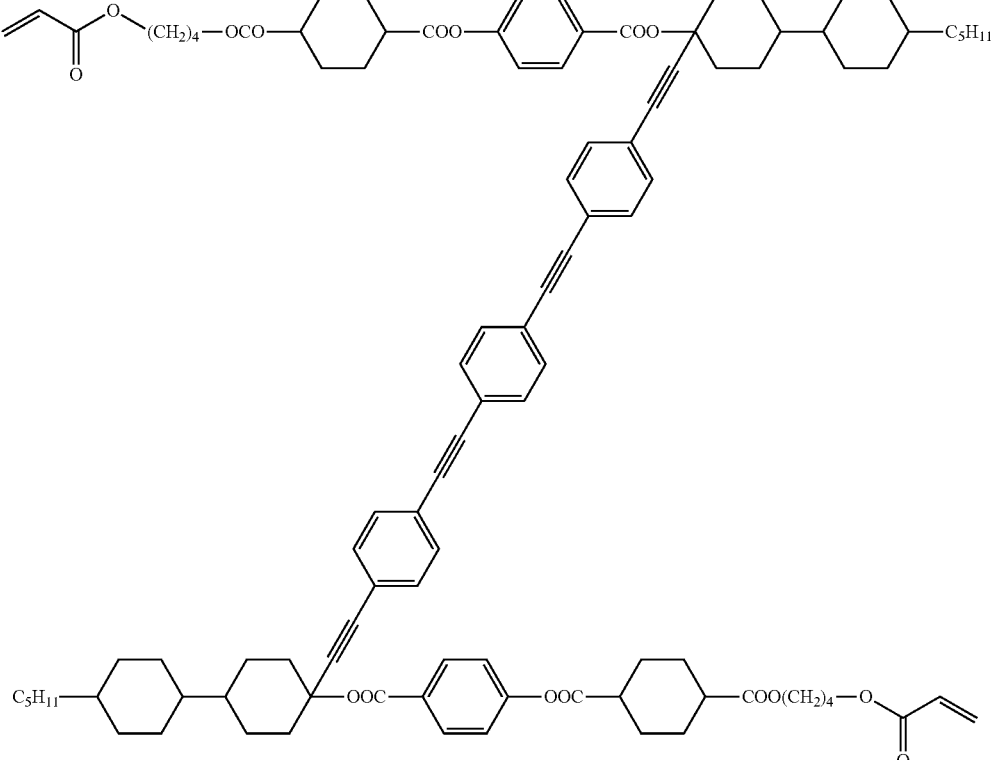 | 37.00 |
The difference between reference mixture CM-3 and example mixture M-3 is that comparison material $C_2$ is mainly replaced by RM-2 in accordance with the present invention. The utilization of RM-2 beside C2 leads to a significant lower dispersion after polymerization.
Mixture M-4: Dispersion (R450/R550)=0.762
| Compound | %-w/w |
|---|---|
| FluorN 561 | 0.42 |
| Irganox 1076 | 0.12 |
| Darocure ®TPO | 1.00 |
| RM-1 | 16.00 |
| 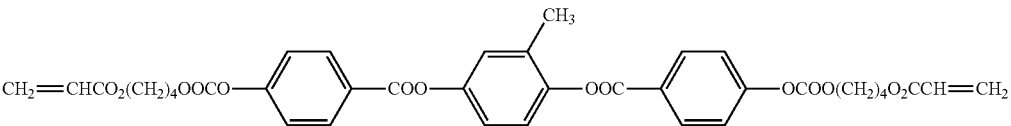 | 29.38 |
|  | 16.08 |

| Compound | %-w/w |
|---|---|
| [structure: acrylate-(CH₂)₄-OCO-cyclohexyl-COO-phenyl-COO-cyclohexyl(–C≡C–phenyl–C≡C–phenyl–C≡C–phenyl–C≡C–phenyl–C≡C–cyclohexyl(C₅H₁₁)-)-cyclohexyl-cyclohexyl-C₅H₁₁; other end: C₅H₁₁-cyclohexyl-cyclohexyl-OOC-phenyl-OOC-cyclohexyl-COO(CH₂)₄-O-acrylate] | 37.00 |

The difference between reference mixture CM-3 and example mixture M-4 is that comparison material C2 is mainly replaced by RM-1 in accordance with the present invention. The utilization of RM-1 instead of C2 leads to a significant lower dispersion after polymerization.

Mixture M-5:

| Compound | %-w/w |
|---|---|
| FluorN 561 | 0.42 |
| Irganox 1076 | 0.12 |
| Adeka NCI-930 | 1.50 |
| RM-2 | 16.68 |
| CH₂=CHCO₂(CH₂)₄OOCO-phenyl-COO-(CH₃-phenyl)-OOC-phenyl-OCOO(CH₂)₄O₂CCH=CH₂ | 28.96 |
| 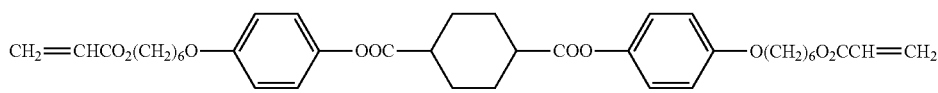 | 20.32 |

CH₂=CHCO₂(CH₂)₆O-phenyl-OOC-cyclohexyl-COO-phenyl-O(CH₂)₆O₂CCH=CH₂

| Compound | %-w/w |
|---|---|
| [structure: acrylate-(CH2)4-OCO-cyclohexyl-COO-phenyl-COO-cyclohexyl(with alkyne chain through 4 phenyl-alkyne units)-cyclohexyl-cyclohexyl-C5H11, and lower half: C5H11-cyclohexyl-cyclohexyl-OOC-phenyl-OOC-cyclohexyl-COO(CH2)4-O-acrylate] | 32.00 |

35

Mixture M-6:

| Compound | %-w/w |
|---|---|
| FluorN 561 | 0.42 |
| Irganox 1076 | 0.12 |
| Adeka NCI-930 | 1.50 |
| Adeka LA-F70 | 1.50 |
| Tinuvin 970 | 0.50 |
| RM-2 | 16.00 |
| CH$_2$=CHCO$_2$(CH$_2$)$_4$OOCO-[phenyl]-COO-[methylphenyl]-OOC-[phenyl]-OCOO(CH$_2$)$_4$O$_2$CCH=CH$_2$ | 28.66 |
| | 19.30 |

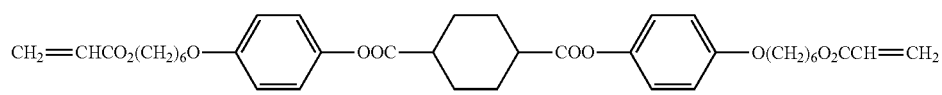

| Compound | %-w/w |
|---|---|
| 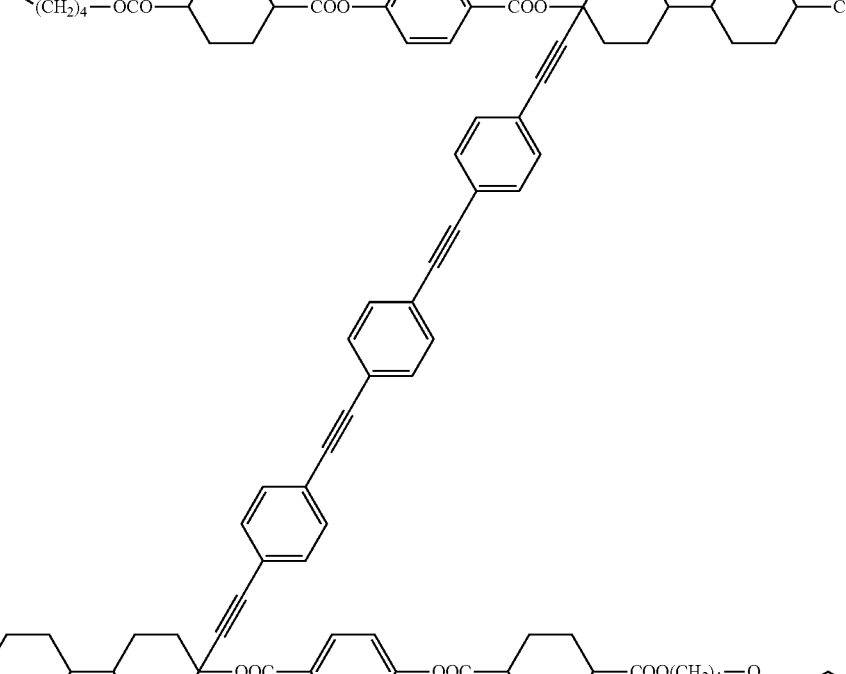 | 32.00 |
Mixture M-7:
| Compound | %-w/w |
|---|---|
| FluorN 561 | 0.42 |
| Irganox 1076 | 0.12 |
| Adeka NCI-930 | 1.50 |
| Adeka LA-F70 | 1.00 |
| Tinuvin 970 | 0.50 |
| Uvinul-3049 | 0.50 |
| RM-2 | 16.00 |
| 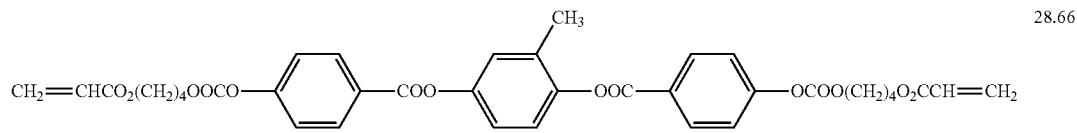 | 28.66 |
| 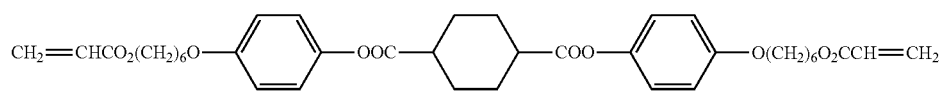 | 19.30 |

-continued

| Compound | %-w/w |
|---|---|
| [structure: acrylate-(CH$_2$)$_4$-OCO-cyclohexyl-COO-phenyl-COO-cyclohexyl(C≡C-phenyl-C≡C-phenyl-C≡C-phenyl-C≡C-cyclohexyl-cyclohexyl-C$_5$H$_{11}$)-cyclohexyl-cyclohexyl-C$_5$H$_{11}$ ... OOC-phenyl-OOC-cyclohexyl-COO(CH$_2$)$_4$-O-acrylate] | 32.00 |
| | 35 |

Mixture M-8:

| Compound | %-w/w |
|---|---|
| BYK 310 | 0.85 |
| Irganox 1076 | 0.12 |
| Adeka NCI-930 | 1.00 |
| SPI-03 | 0.50 |
| Adeka LA-F70 | 1.00 |
| Tinuvin 970 | 2.00 |
| Tinuvin 770 | 0.09 |
| RM-2 | 16.00 |
| CH$_2$=CHCO$_2$(CH$_2$)$_4$OOCO-phenyl-COO-(methylphenyl)-OOC-phenyl-OCOO(CH$_2$)$_4$O$_2$CCH=CH$_2$ | 29.07 |
| CH$_2$=CHCO$_2$(CH$_2$)$_6$O-phenyl-OOC-cyclohexyl-COO-phenyl-O(CH$_2$)$_6$O$_2$CCH=CH$_2$ 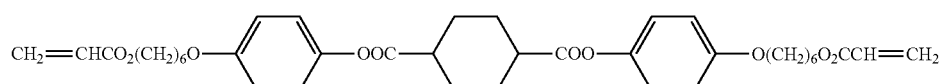 | 19.87 |

-continued
| Compound | %-w/w |
|---|---|
| [structure] | 29.50 |
| | 35 |
Mixture M-9:
| Compound | %-w/w |
|---|---|
| BYK 310 | 0.85 |
| Irganox 1076 | 0.12 |
| Adeka NCI-930 | 1.00 |
| SPI-03 | 0.50 |
| Adeka LA-F70 | 2.00 |
| Tinuvin 770 | 0.09 |
| Uvinul 3049 | 0.50 |
| RM-2 | 16.00 |
| [structure] | 28.34 |
| 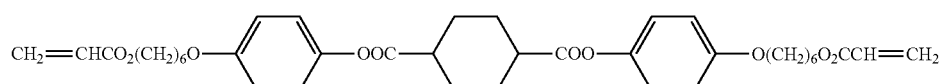 | 19.35 |

| Compound | %-w/w |
|---|---|
|  | 31.25 |
Mixture Examples—ND+C
The following mixtures for ND+0 are prepared in accordance with the following tables, polymerised and the resulting optical characteristics, such as dispersions of the resulting film are measured:
Comparison Mixture CM-4:
| Compound | %-w/w |
|---|---|
| FluorN 562 | 1.00 |
| Irganox 1076 | 0.12 |
| Adeka N1919-T | 3.00 |
|  | 26.00 |
|  | 28.00 |
| | 12.88 |

| Compound | %-w/w |
|---|---|
| [structure: acrylate-(CH₂)₄-OCO-cyclohexyl-COO-phenyl-COO-cyclohexyl(-C≡C-phenyl-C≡C-phenyl-C≡C-phenyl-C≡C-cyclohexyl-cyclohexyl-C₅H₁₁)-cyclohexyl-C₅H₁₁; lower arm: C₅H₁₁-cyclohexyl-cyclohexyl-OOC-phenyl-OOC-cyclohexyl-COO(CH₂)₄-O-acrylate] | 29.00 |

35

Dispersion (R450/R550) at 40° C.=0.878
Δn ($R_{th/d}$)=0.046
Comparison Mixture CM-5:

| Compound | %-w/w |
|---|---|
| FluorN 562 | 1.00 |
| Irganox 1076 | 0.12 |
| Adeka N1919-T | 3.00 |
| CH₂=CHCOO(CH₂)₆O-phenyl-COO-phenyl-cyclohexyl-C₃H₇ | 26.00 |
| | 31.43 |
| CH₂=CHCO₂(CH₂)₆O-phenyl-OOC-cyclohexyl-COO-phenyl-O(CH₂)₆O₂CCH=CH₂ | |
| | 14.46 |
| CH₂=CHCO₂(CH₂)₄OOCO-phenyl-COO-(methylphenyl)-OOC-phenyl-OCOO(CH₂)₄O₂CCH=CH₂ | |

| Compound | %-w/w |
|---|---|
| [structure] | 24.00 |
Dispersion (R450/R550) at 40° C. = 0.924
Δn ($R_{th/d}$) = 0.054
By reducing the amount of compounds of formula ND (CM-4 vs. CM-5), the dispersion as well as the birefringence increases significantly.
Mixture M-10:
| Compound | %-w/w |
|---|---|
| FluorN 562 | 1.00 |
| Irganox 1076 | 0.12 |
| Adeka N1919-T | 3.00 |
| RM-2 | 14.46 |
| [structure] CH₂=CHCOO(CH₂)₆O-...-C₃H₇ | 26.00 |
| 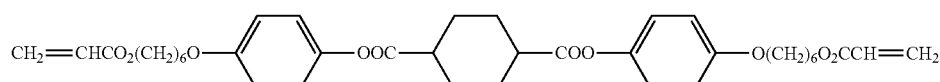 | 31.42 |

| Compound | %-w/w |
|---|---|
| 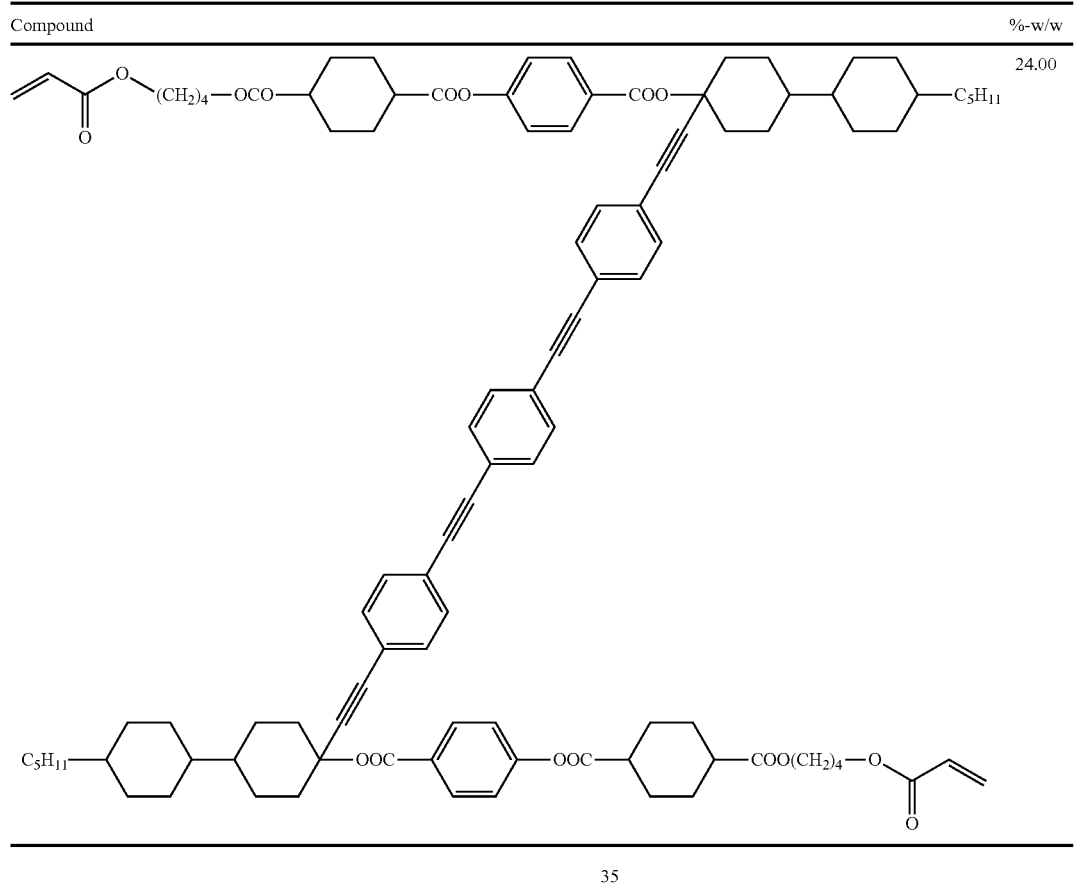 | 24.00 |

Dispersion (R450/R550) at 40° C.=0.924
Δn (R$_{th/d}$)=0.051

By utilizing RM-2 and reducing the amount of compounds of formula ND, the dispersion decreases significantly (CM-4 vs. M5).

The invention claimed is:

1. One or more compounds selected from the group consisting of:

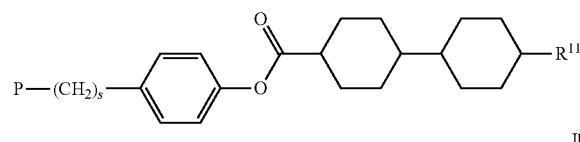

Ia

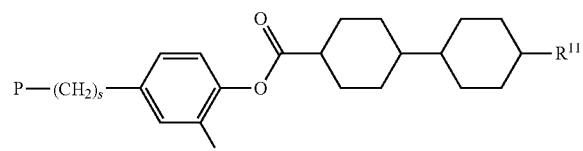

Ib

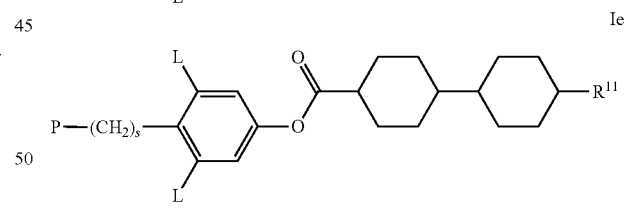

Ic

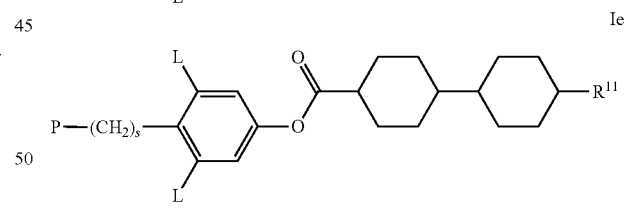

Id

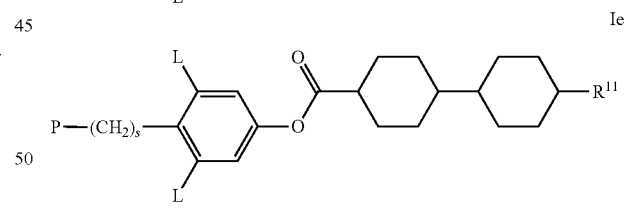

Ie wherein
P is a polymerisable group,
s denotes an integer from 1 to 7,
$R^{11}$ is alkyl, alkoxy, thioalkyl, alkylcarbonyl, alkoxycarbonyl, alkylcarbonyloxy or alkoxycarbonyloxy which is optionally fluorinated, and
L on each occurrence, identically or differently, denotes —OH, —F, —Cl, or straight-chain alkyl, alkoxy, alkylcarbonyl, alkoxycarbonyl, alkylcarbonyloxy or alkoxycarbonyloxy having 1 to 12 C atoms or branched or cyclic alkyl, alkoxy, alkylcarbonyl, alkoxycarbonyl, alkylcarbonyloxy or alkoxycarbonyloxy having 3 to 12 C atoms, in which, in addition, one or more H atoms may be replaced by F or Cl.

2. The compound according to claim 1, selected from the group consisting of the following compounds:

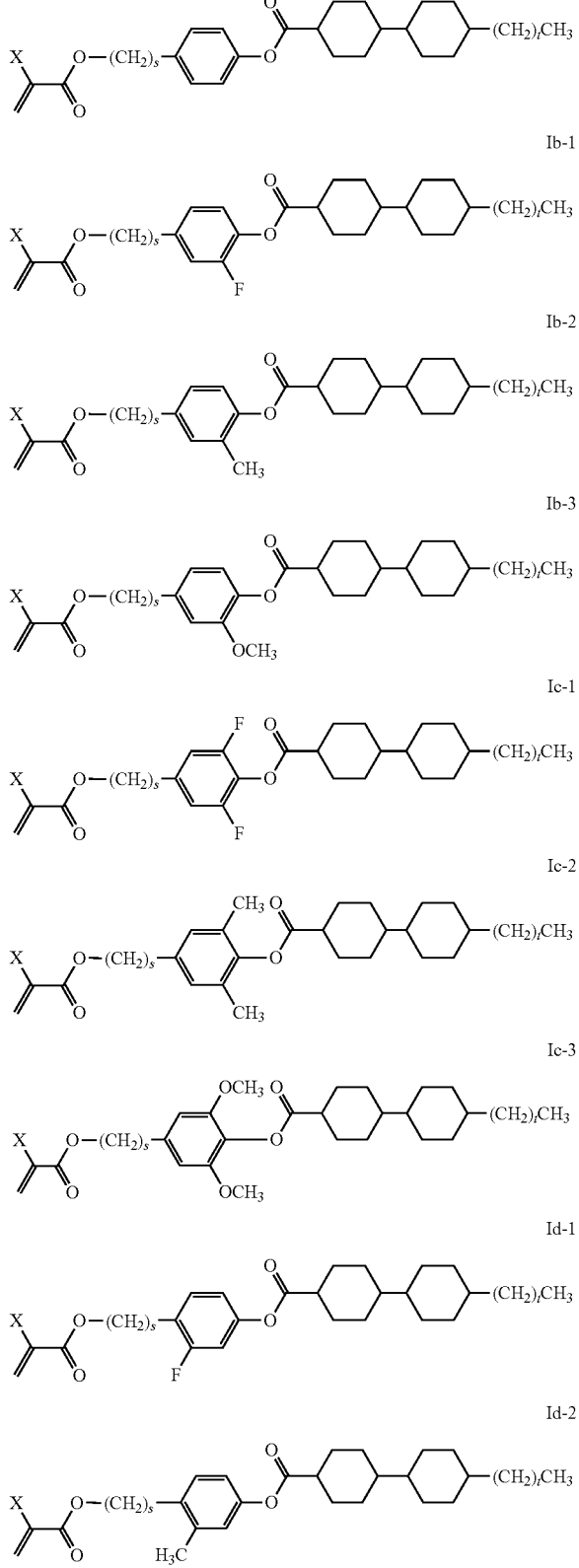

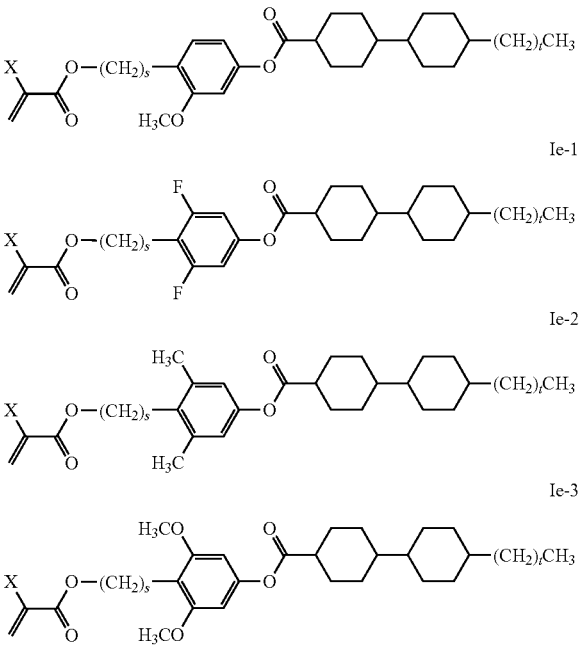

wherein
X denotes H or —CH$_3$,
s denotes 0, 1, 2, 3, 4, 5, 6 or 7, and
t denotes 0, 1, 2, 3, 4, or 5.

3. A reactive mesogenic mixture comprising at least one compound of formulae Ia to Ie according to claim 1.

4. The mixture according to claim 3, comprising one or more reactive mesogens of formula DRM:

$$P^1\text{-Sp}^1\text{-MG-Sp}^2\text{-}P^2 \qquad \text{DRM}$$

wherein
P$^1$ and P$^2$ independently of each other denote a polymerizable group,
Sp$^1$ and Sp$^2$ independently of each other are a spacer group or a single bond, and
MG is a rod-shaped mesogenic group of formula MG:

$$\text{-}(A^1\text{-}Z^1)_n\text{-}A^2\text{-} \qquad \text{MG}$$

wherein
A$^1$ and A$^2$ denote, in case of multiple occurrence independently of one another, an aromatic or alicyclic group, which optionally contains one or more heteroatoms selected from N, O and S, and is optionally mono- or polysubstituted by L$^1$,
L$^1$ is P-Sp-, F, Cl, Br, I, —CN, —NO$_2$, —NCO, —NCS, —OCN, —SCN, —C(=O)NR$^{00}$R$^{000}$, —C(=O)OR$^{00}$, —C(=O)R$^{00}$, —NR$^{00}$R$^{000}$, —OH, —SF$_5$, optionally substituted silyl, aryl or heteroaryl with 1 to 12 C atoms, straight chain alkyl, alkoxy, alkylcarbonyl, alkoxycarbonyl, alkylcarbonyloxy or alkoxycarbonyloxy with 1 to 12 C atoms or branched alkyl, alkoxy, alkylcarbonyl, alkoxycarbonyl, alkylcarbonyloxy or alkoxycarbonyloxy with 3 to 12 C atoms, wherein one or more H atoms are optionally replaced by F or Cl,
R$^{00}$ and R$^{000}$ independently of each other denote H or alkyl with 1 to 12 C-atoms,
Z$^1$ denotes, in case of multiple occurrence independently of one another, —O—, —S—, —CO—, —COO—, —OCO—, —S—CO—, —CO—S—, —O—COO—, —CO—NR$^{00}$—, —NR$^{00}$—CO—, —NR$^{00}$—CO—NR$^{000}$—, —NR$^{00}$—CO—O—, —O—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_{n1}$, —CF$_2$CH$_2$—, —CH$_2$CF$_2$—, —CF$_2$CF$_2$—, —CH=N—, —N=CH—, —N=N—, —CH=CR$^{00}$—, —CY$^1$=CY$^2$—, —C≡C—, —CH=CH—COO—, —OCO—CH=CH— or a single bond, Y$^1$ and Y$^2$ independently of each other denote H, F, Cl or CN, n is 1, 2, 3 or 4, and n1 is an integer from 1 to 10.

5. The mixture according to claim 4, comprising one or more reactive mesogens selected from the following formulae:

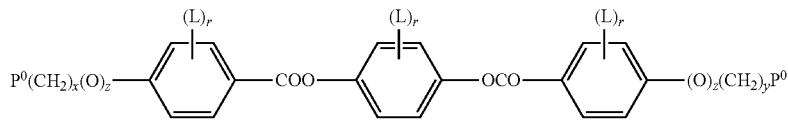
DRMa1

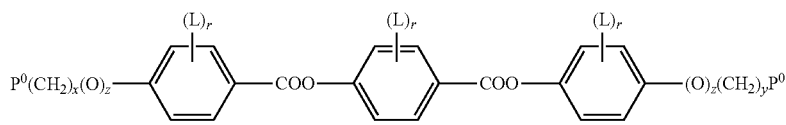
DRMa2

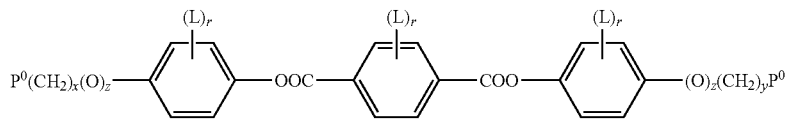
DRMa3

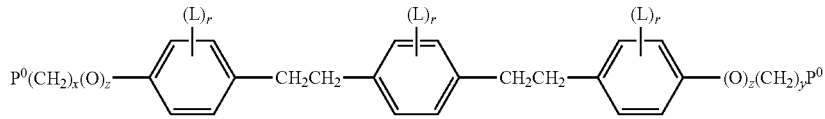
DRMa4

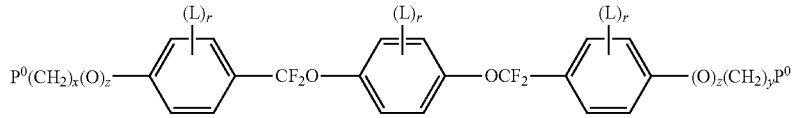
DRMa5

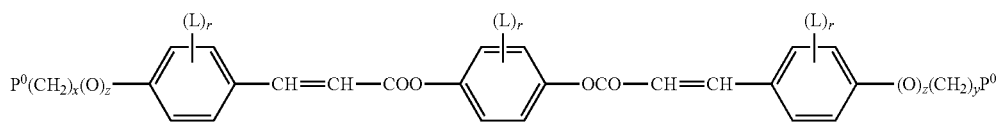
DRMa6

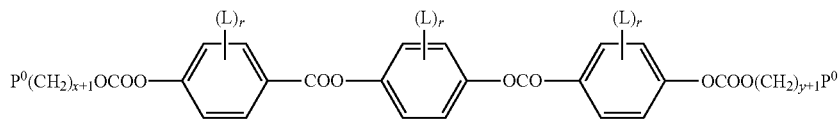
DRMa7

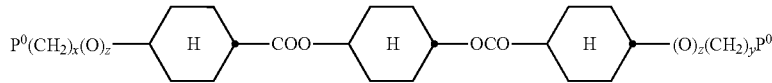
DRMb

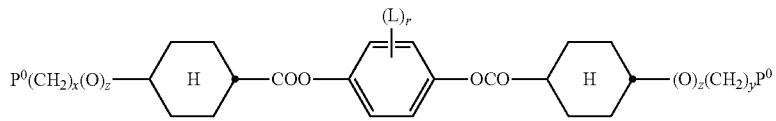
DRMc

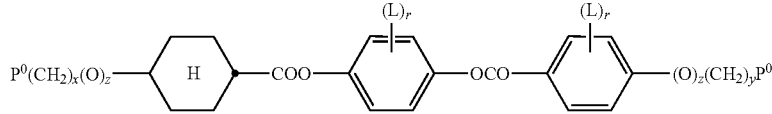
DRMd

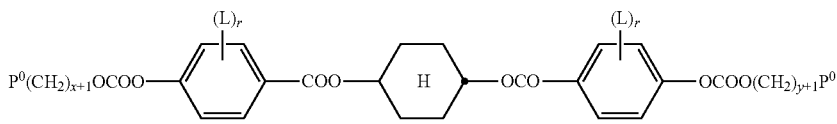

DRMe wherein
P⁰ is, in case of multiple occurrence independently of one another, an acryl, methacryl, oxetane, epoxy, vinyl, heptadiene, vinyloxy, propenyl ether or styrene group,
L has on each occurrence identically or differently one of the meanings given for $L^1$ in formula DRM,
r is 0, 1, 2, 3 or 4,
x and y are independently of each other 0 or identical or different integers from 1 to 12, and
z is each and independently, 0 or 1, with z being 0 if the adjacent x or y is 0.

6. The mixture according to claim 3, comprising one or more reactive mesogens of the formula:

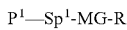

$P^1$—$Sp^1$-MG-R  MRM wherein
$P^1$ denotes a polymerizable group,
$Sp^1$ is a spacer group or a single bond, and
MG is a rod-shaped mesogenic group of formula MG:

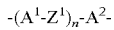

-($A^1$-$Z^1$)$_n$-$A^2$-  MG wherein
$A^1$ and $A^2$ denote, in case of multiple occurrence independently of one another, an aromatic or alicyclic group, which optionally contains one or more heteroatoms selected
from N, O and S, and is optionally mono- or polysubstituted by $L^1$,
$L^1$ is P-Sp-, F, Cl, Br, I, —CN, —NO$_2$, —NCO, —NCS, —OCN, —SCN, —C(=O)NR$^{00}$R$^{000}$, —C(=O)OR$^{00}$, —C(=O)R$^{00}$, —NR$^{00}$R$^{000}$, —OH, —SF$_5$, optionally substituted silyl, aryl or heteroaryl with 1 to 12 C atoms, straight chain alkyl, alkoxy, alkylcarbonyl, alkoxycarbonyl, alkylcarbonyloxy or alkoxycarbonyloxy with 1 to 12 C atoms or branched alkyl, alkoxy, alkylcarbonyl, alkoxycarbonyl, alkylcarbonyloxy or alkoxycarbonyloxy with 3 to 12 C atoms, wherein one or more H atoms are optionally replaced by F or Cl,
R$^{00}$ and R$^{000}$ independently of each other denote H or alkyl with 1 to 12 C-atoms,
$Z^1$ denotes, in case of multiple occurrence independently of one another, —O—, —S—, —CO—, —COO—, —OCO—, —S—CO—, —CO—S—, —O—COO—, —CO—NR$^{00}$—, —NR$^{00}$—CO—, —NR$^{00}$—CO—NR$^{000}$, —NR$^{00}$—CO—O—, —O—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_{n1}$, —CF$_2$CH$_2$—, —CH$_2$CF$_2$—, —CF$_2$CF$_2$—, —CH=N—, —N=CH—, —N=N—, —CH=CR$^{00}$—, —CY$^1$=CY$^2$—, —C≡C—, —CH=CH—COO—, —OCO—CH=CH— or a single bond,
$Y^1$ and $Y^2$ independently of each other denote H, F, Cl or CN,
n is 1, 2, 3 or 4,
$n^1$ is an integer from 1 to 10
R is F, Cl, Br, I, —CN, —NO$_2$, —NCO, —NCS, —OCN, —SCN, —C(=O)NR$^x$R$^y$, —C(=O)X, —C(=O)OR$^x$, —C(=O)R$^y$, —NR$^x$R$^y$, —OH, —SF$_5$, optionally substituted silyl, straight chain alkyl, alkoxy, alkylcarbonyl, alkoxycarbonyl, alkylcarbonyloxy or alkoxycarbonyloxy with 1 to 12 C atoms or branched alkyl, alkoxy, alkylcarbonyl, alkoxycarbonyl, alkylcarbonyloxy or alkoxycarbonyloxy with 3 to 12 C atoms, wherein one or more H atoms are optionally replaced by F or Cl,
X is halogen, and
R$^x$ and R$^y$ are independently of each other H or alkyl with 1 to 12 C-atoms.

7. The mixture according to claim 6, comprising one or more reactive mesogens selected from the following formulae:

MRM1
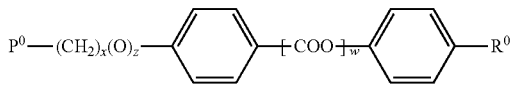

MRM2
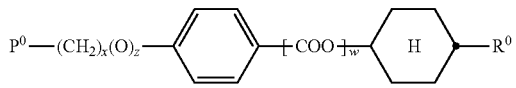

MRM3
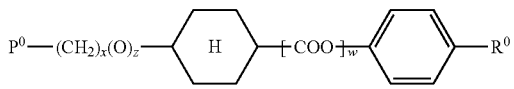

MRM4
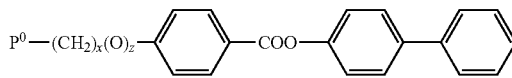

MRM5
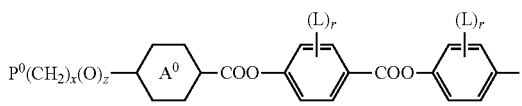

MRM6
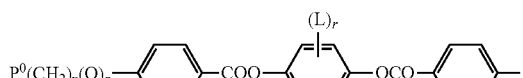

MRM7
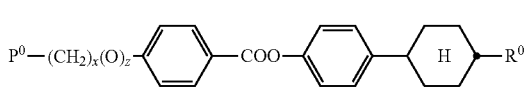

MRM8

MRM9
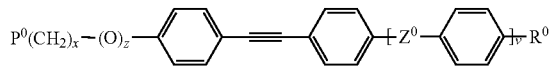
MRM11
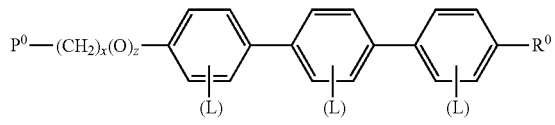
MRM10
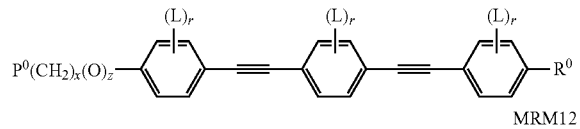
MRM12
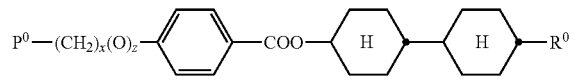
MRM13
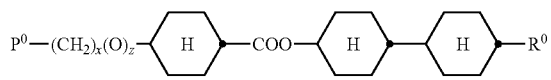
MRM14
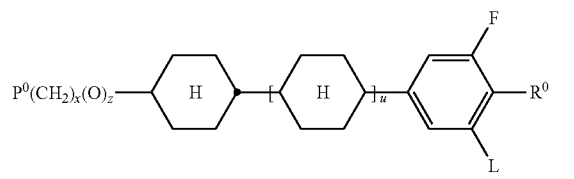
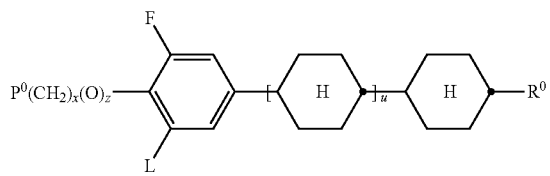
MRM15
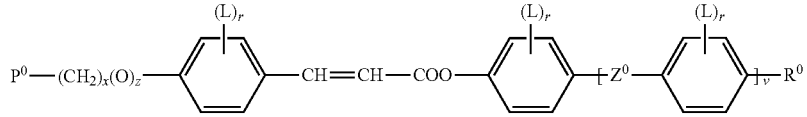
MRM16
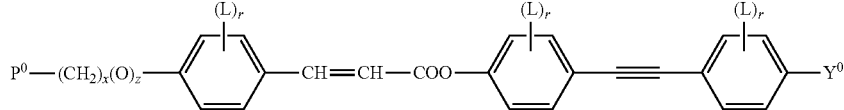
MRM17
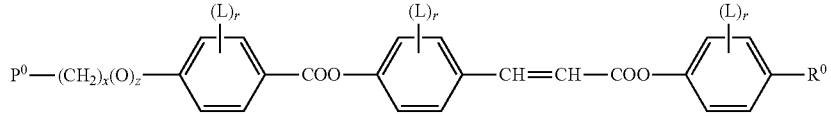
MRM18
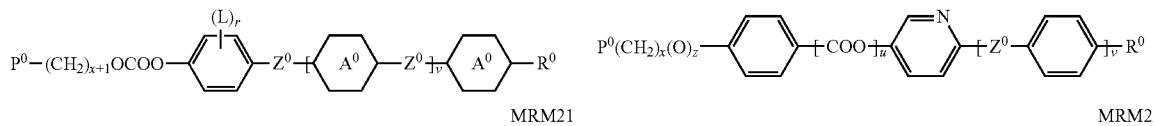
MRM19
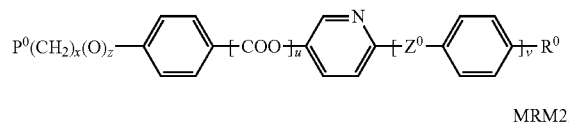
MRM20
MRM21
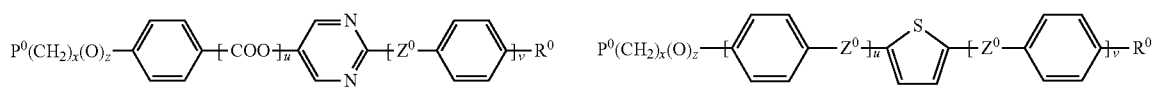
MRM22
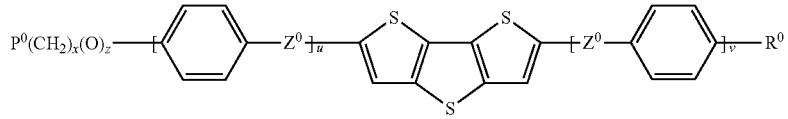
MRM23
MRM24
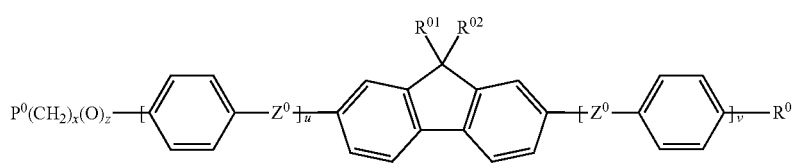

MRM25

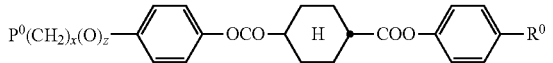

MRM26

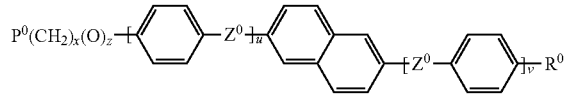

MRM27

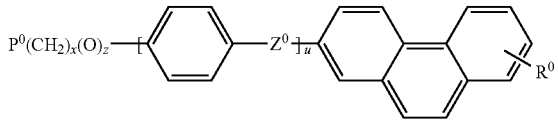

wherein
- $P^0$ is, in case of multiple occurrence independently of one another, an acryl, methacryl, oxetane, epoxy, vinyl, heptadiene, vinyloxy, propenyl ether or styrene group,
- L has on each occurrence identically or differently one of the meanings given for $L^1$ in formula DRM,
- r is 0, 1, 2, 3 or 4,
- x and y are independently of each other 0 or identical or different integers from 1 to 12,
- z is each and independently, 0 or 1, with z being 0 if the adjacent x or y is 0,
- $R^0$ is alkyl, alkoxy, thioalkyl, alkylcarbonyl, alkoxycarbonyl, alkylcarbonyloxy or alkoxycarbonyloxy with 1 or more C atoms or denotes $Y^0$,
- $Y^0$ is F, Cl, CN, $NO_2$, $OCH_3$, OCN, SCN, $SF_5$, or mono- oligo- or polyfluorinated alkyl or alkoxy with 1 to 4 C atoms,
- $Z^0$ is —COO—, —OCO—, —$CH_2CH_2$—, —$CF_2O$—, —$OCF_2$—, —CH=CH—, —OCO—CH=CH—, —CH=CH—COO—, or a single bond,
- $A^0$ is, in case of multiple occurrence independently of one another, 1,4-phenylene that is unsubstituted or substituted with 1, 2, 3 or 4 groups L, or trans-1,4-cyclohexylene,
- u and v are independently of each other 0, 1 or 2,
- W is 0 or 1, and wherein the benzene and naphthalene rings can additionally be substituted with one or more identical or different groups L, and Z in formula MRM15 denotes 1.

8. The mixture according to claim 3, comprising one or more reactive mesogens of formula ND:

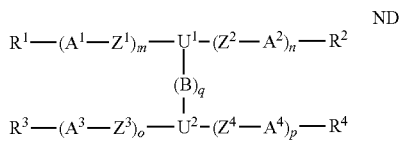

wherein
$U^{1,2}$ are independently of each other selected from

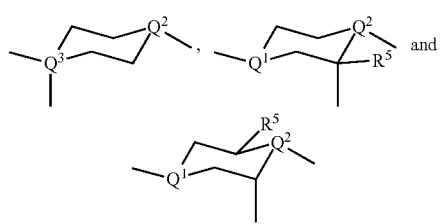

including their mirror images, wherein the rings $U^1$ and $U^2$ are each bonded to the group —$(B)_q$— via the axial bond, and one or two non-adjacent $CH_2$ groups in these rings are optionally replaced by O and/or S,
- $Q^{1,2}$ are independently of each other CH or SiH,
- $Q^3$ is C or Si,
- B is in each occurrence independently of one another —C≡C—, —$CY^1$=$CY^2$—or an optionally substituted aromatic or heteroaromatic group,
- $Y^{1,2}$ are independently of each other H, F, Cl, CN or $R^0$,
- q is an integer from 1 to 10,
- $A^{1-4}$ are independently of each other selected from non-aromatic, aromatic or heteroaromatic carbocyclic or heterocyclic groups, which are optionally substituted by one or more groups $R^5$, and wherein each of -$(A^1$-$Z^1)_m$—$U^1$—$(Z^2$-$A^2)_n$- and -$(A^3$-$Z^3)_o$—$U^2$—$(Z^4$-$A^4)_p$-does not contain more aromatic groups than non-aromatic groups,
- $Z^{1-4}$ are independently of each other —O—, —S—, —CO—, —COO—, —OCO—, —O—COO—, —CO—$NR^0$—, —$NR^0$—CO—, —$NR^0$—CO—$NR^0$—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$(CH_2)_3$—, —$(CH_2)_4$—, —$CF_2CH_2$—, —$CH_2CF_2$—, —$CF_2CF_2$—, —CH=CH—, —$CY^1$=$CY^2$—, —CH=N—, —N=CH—, —N=N—, —CH=$CR^0$—, —C≡C—, —CH=CH—COO—, —OCO—CH=CH—, $CR^0R^{00}$ or a single bond,
- $R^0$ and $R^{00}$ are independently of each other H or alkyl with 1 to 12 C-atoms,
- m and n are independently of each other 0, 1, 2, 3 or 4, and p are independently of each other 0, 1, 2, 3 or 4,
- $R^{1-5}$ are independently of each other identical or different groups selected from H, halogen, —CN, —NC, —NCO, —NCS, —OCN, —SCN, —C(=O)$NR^0R^{00}$, —C(=O)$X^0$, —C(=O)$R^0$, —$NH_2$, —$NR^0R^{00}$, —SH, —$SR^0$, —$SO_3H$, —$SO_2R^0$, —OH, —$NO_2$, —$CF_3$, —$SF_5$, P-Sp-, optionally substituted silyl, or carbyl or hydrocarbyl with 1 to 40 C atoms that is optionally substituted and optionally comprises one or more hetero atoms, or denote P or P-Sp-, or are substituted by P or P-Sp-, wherein at least one group $R^{1-5}$ denotes or is substituted by P or P-Sp-,
- P is a polymerisable group, and
- Sp is a spacer group or a single bond.

9. A formulation comprising one or more compounds of formulae Ia to Ie according to claim 1 and one or more photoinitiators.

10. A formulation according to claim 9 further comprising one or more stabilizers.

11. A formulation according to claim 10 further comprising one or more lubricants.

12. A polymer obtainable by polymerizing a compound of formulae Ia to Ie according to claim 1.

13. An optical, electrooptical or electronic device or component, comprising a compound according to claim 1.

14. A formulation comprising the mixture of claim 3 and one or more photoinitiators.

15. The formulation of claim 14, further comprising one or more stabilizers.

16. The formulation of claim 15, further comprising one or more lubricants.

17. An optical, electrooptical or electronic device or component, comprising the mixture of claim 3.

* * * * *

UNITED STATES PATENT AND TRADEMARK OFFICE
CERTIFICATE OF CORRECTION

PATENT NO. : 12,162,834 B2
APPLICATION NO. : 17/607770
DATED : December 10, 2024
INVENTOR(S) : Jack Bradford et al.

It is certified that error appears in the above-identified patent and that said Letters Patent is hereby corrected as shown below:

In the Claims

In Column 118, Line 29 in Claim 6, delete "$n^1$" and insert -- n1 --.

In Column 121, Line 39 in Claim 7, delete "W" and insert -- w --.

In Column 121, Line 43 in Claim 7, delete "Z" and insert -- z --.

In Column 122, Line 36 in Claim 8, delete "$NR^0$-," and insert -- $NR^{00}$-, --.

In Column 122, Line 47 in Claim 8, before "and" insert -- o --.

Signed and Sealed this
Twenty-seventh Day of May, 2025

Coke Morgan Stewart
*Acting Director of the United States Patent and Trademark Office*